US008143037B2

(12) United States Patent
Zahn et al.

(10) Patent No.: US 8,143,037 B2
(45) Date of Patent: Mar. 27, 2012

(54) **ETHANOLOGENIC *CLOSTRIDIUM* SPECIES, *CLOSTRIDIUM COSKATII***

(75) Inventors: James A. Zahn, Campton Hills, IL (US); Jyotisna Saxena, Naperville, IL (US)

(73) Assignee: Coskata, Inc., Warrenville, IL (US)

( * ) Notice: Subject to any disclaimer, the term of this patent is extended or adjusted under 35 U.S.C. 154(b) by 0 days.

(21) Appl. No.: 12/727,320

(22) Filed: Mar. 19, 2010

(65) Prior Publication Data

US 2011/0229947 A1 Sep. 22, 2011

(51) Int. Cl.
*C12P 7/06* (2006.01)
*C12N 1/20* (2006.01)

(52) U.S. Cl. .................................. 435/161; 435/252.7
(58) Field of Classification Search .................. None
See application file for complete search history.

(56) References Cited

U.S. PATENT DOCUMENTS

| | | | |
|---|---|---|---|
| 5,173,429 | A | 12/1992 | Gaddy et al. |
| 5,192,673 | A | 3/1993 | Jain et al. |
| 5,593,886 | A | 1/1997 | Gaddy |
| 5,807,722 | A | 9/1998 | Gaddy |
| 6,136,577 | A | 10/2000 | Gaddy |
| 6,753,170 | B2 | 6/2004 | Gaddy et al. |
| 7,285,402 | B2 | 10/2007 | Gaddy et al. |
| 2007/0275447 | A1 | 11/2007 | Lewis et al. |
| 2008/0057554 | A1 | 3/2008 | Huhnke et al. |
| 2008/0305539 | A1 | 12/2008 | Hickey et al. |
| 2009/0017512 | A1 | 1/2009 | May et al. |

FOREIGN PATENT DOCUMENTS

WO 2008/028055 A2 3/2008

OTHER PUBLICATIONS

Abrini, et al., "*Clostridium autoethanogenum*, sp. nov., an anaerobic bacterium that produces ethanol from carbon monoxide", Arch. Microbiol., vol. 161: pp. 345-351, 1994.
Arora et al., "Production of Ethanol From Refinery Waste Gases", Phase II—Technology Development Annual Report, Jul. 1995.
Balch, et al., "Methanogens: reevaluation of a unique biological group", Microbiol. Rev., vol. 43(2): pp. 260-296, Jun. 1979.
Balch, et al., "New approach to the cultivation of methanogenic bacteria: 2-mercaptoethanesulfonic acid (HS-CoM)-dependent growth of Methanobacterium ruminantium in a pressureized atmosphere", Appl. Environ. Microbiol.; vol. 32(6): pp. 781-791, Dec. 1976.
Barik, et al., "Biological Production of Alcohols from Coal Through Indirect Liquefaction", Appl. Biochem. Biotechnol. vol. 18: pp. 363-378, 1988.
Barik et al., Wise, D.L. (editor), "Bioprocessing and Biotreatment of Coal", New York: Marcel Dekker, Inc.; pp. 131-154, 1990.
Bryant, et al., "Commentary on the Hungate technique for culture of anaerobic bacteria", Am Journal Clinical Nutrition vol. 25: pp. 1324-1328, Dec. 1972.
Cashion, et al., "A rapid method for base ratio determination of bacterial DNA", Analytical Biochemistry vol. 1: pp. 461-466, 1977.
Collins, "The phylogeny of the genus *Clostridium*: Proposal of Five New Genera and Eleven New Species Combinations", International Journal of Systematic Bacteriology, vol. 44 (4): pp. 812-826, 1994.
De Ley, et al., "The Quantitative Measurement of DNA Hybridization from Renaturation Rates", Eur. J. Biochem. vol. 12: pp. 133-142, 1970.
Drake, et al., "Acetogenic Prokaryotes", Prokaryotes, Chapter 1.13, vol. 2: pp. 354-420, 2006.
Grethlein et al., "Continuous Production of Miexed Alcohols and Acids from Carbon Monoxide", Applied biochemistry & Biotechnology, vol. 24/25, pp. 875-884, 1990.
Huss, V. A. R., Festl, H. & Schleifer, K. H. 1983. Studies on the Spectrophotometric determination of DNA hybridization from renaturation rates. Syst Appl Microbiol. 4, 184-192.
Inokuma, et al., "Characterization of enzymes involved in the ethanol production of *Moorella* sp. HUC22-1", Archives of Microbiol. vol. 188(1): pp. 37-45, 2007.
Johnson, "Taxonomy of the Clostridia: Ribosomal Ribonucleic Acid Homologies among the Species", J Gen Microbiol, vol. 88: pp. 229-244, 1975.
Liou et al., 2005, Int. J. Syst. Envol. Microbiol. 55: 2085-2091.
Skerman, V. B. D., McGowan, V. & Sneath, P. H. A. (editors), "Approved Lists of Bacterial Names"—(amended edition). Washington, DC: American Society for Microbiology; pp. 40-59, 1989.
Tanner, et al., "*Clostridium ijungdahlii* sp. nov., an acetogenic species in clostridial rRNA homology group I", Int J Syst Bacteriol; Apr. 1993; 43(2), pp. 232-236.
International Search Report of International Application No. PCT/US2011/028711, dated Nov. 28, 2011.

*Primary Examiner* — Tekchand Saidha
*Assistant Examiner* — MD. Younus Meah
(74) *Attorney, Agent, or Firm* — McDonnell Boehnen Hulbert & Berghoff LLP

(57) ABSTRACT

An isolated clostridia bacterial species (*Clostridium coskatii* ATCC No. PTA-10522, "PS02") is provided. Under anaerobic conditions *C. coskatii* can convert CO and/or $H_2$ and/or $CO_2$ to ethanol or acetate. Thus, this bacterium is capable of transforming waste gases (e.g. syngas and refinery wastes) into useful products.

10 Claims, 26 Drawing Sheets

Fig. 8a.

```
              10         20         30         40
        ....|....|....|....|....|....|....|....|
  1     --------TGGAGAGTTTGATCCTGGCTCAGGACGAACGCT 50         60         70         80
        ....|....|....|....|....|....|....|....|
 34     GGCGGCGTGCTTAACACATGCAAGTCGAGCGATGAA----

90        100        110        120
        ....|....|....|....|....|....|....|....|
 69     -----G-CTCCTTCGG---GAG-------TGGATTAGCGGC 130        140        150        160
        ....|....|....|....|....|....|....|....|
 95     GGACGGGTGAGTAACACGTGGGTAACCTACCTCAAAGAGG 170        180        190        200
        ....|....|....|....|....|....|....|....|
135     GGATAGCCTCCCGAAAGGAGATTAATACCGCATAATAA 210        220        230        240
        ....|....|....|....|....|....|....|....|
175     TCAGTTTTCACATGGARACTGRTTAAAGGAG---TAAT- 250        260        270        280
        ....|....|....|....|....|....|....|....|
210     --CCGCTTTGAGATGGACCCGCGGCGCATTAGCTAGTTGG 290        300        310        320
        ....|....|....|....|....|....|....|....|
249     TAGGGTAACGGCCTACCAAGGCGACGATGCGTAGCCGACC 330        340        350        360
        ....|....|....|....|....|....|....|....|
289     TGAGAGGGTGATCGGCCACATTGGAACTGAGAGACGGTCC 370        380        390        400
        ....|....|....|....|....|....|....|....|
329     AGACTCCTACGGGAGGCAGCAGTGGGAATATTGCACAAT 410        420        430        440
        ....|....|....|....|....|....|....|....|
369     GGGCGAAAGCCTGATGCAGCAACGCCGCGTGAGTGAAGAA 450        460        470        480
        ....|....|....|....|....|....|....|....|
409     GGTTTTCGGATTGTAAAGCTCTGTCTTTGGGGACGA----
```

Fig. 8a. Continued

```
             970       980       990      1000
           ....|....|....|....|....|....|....|....|
893   CGGGGGCCCCGCACAAGCAGCGGAGCATGTGGTTTAATTCG 1010      1020      1030      1040
           ....|....|....|....|....|....|....|....|
933   AAGCAACGCGAAGAACCTTACCTGGACTTGACATACCCTG 1050      1060      1070      1080
           ....|....|....|....|....|....|....|....|
973   AATATCTTAGAGATAAGAAG----CCCTTCGGG---C 1090      1100      1110      1120
           ....|....|....|....|....|....|....|....|
1006  AGGGATACAGGTGGTGCATGGTTGTCGTCAGCTCGTGTCG 1130      1140      1150      1160
           ....|....|....|....|....|....|....|....|
1046  TGAGATGTTAGGTT-AAGTCCTGCAACGAGCGCAACCCCT 1170      1180      1190      1200
           ....|....|....|....|....|....|....|....|
1085  GTTGTTAGTTGCTAACA--TTTAGTTGAGCACTCTAGCAA 1210      1220      1230      1240
           ....|....|....|....|....|....|....|....|
1123  GACTGCCGCGGTTAACGCGG-AGGAAGGTGGGAT-GACG 1250      1260      1270      1280
           ....|....|....|....|....|....|....|....|
1161  TCAAATCATCAT-GCCCTTATG-TCCAGGGCAACACACG 1290      1300      1310      1320
           ....|....|....|....|....|....|....|....|
1199  TGCTACAATGGGCAG-TACA-GAGAGAAGCAAGAYC-GCA 1330      1340      1350      1360
           ....|....|....|....|....|....|....|....|
1235  -AGGTGGAGCAAACCTCA-AAAACT-GCCCCAGTTCGG- 1370      1380      1390      1400
           ....|....|....|....|....|....|....|....|
1271  -------------------------ATTGCAGGCTGAAACTC 1410      1420      1430      1440
           ....|....|....|....|....|....|....|....|
1289  GCCTACATGAAGTTGGAGTTGCTAGTAATCGCGAATCAGA
```

Fig. 8a. Continued

```
              1450        1460        1470        1480
         ....|....|....|....|....|....|....|....|
1329     ATGTCGCGGTGAATACGTTCCCGGGCCTTG-TACACACCG 1490        1500        1510        1520
         ....|....|....|....|....|....|....|....|
1368     CCCGTCACACCATGAGAGCTGGCAACA-CCCGAAGTCCGT 1530        1540        1550        1560
         ....|....|....|....|....|....|....|....|
1407     AGTCTAAC---GAAGAGGAC-GCGGCCGAAGGTGGGTT 1570        1580        1590        1600
         ....|....|....|....|....|....|....|....|
1443     AGTAATTGGGGTGAA-GTCGTAACAAGGTA----------

1610        1620
         ....|....|....|....|
1471     --------------------     [SEQ ID NO: 3]
```

FIG. 9

| | PS02 | C. ljungdahlii ERI-2 GU139551 | C. ljungdahlii C-01 GU139550 | C. ragsdalei AY170378 | C. ljungdahlii PETC GU139552 | C. autoethanogenum Y18178 |
|---|---|---|---|---|---|---|
| PS02 | ID | | | | | |
| C. ljungdahlii ERI-2 | 99.86 | ID | | | | |
| C. ljungdahlii C-01 | 99.31 | 99.79 | ID | | | |
| C. ragsdalei AY170378 | 99.57 | 99.48 | 99.28 | ID | | |
| C. ljungdahlii PETC | 99.79 | 99.58 | 99.45 | 99.79 | ID | |
| C. autoethanogenum | 99.79 | 99.57 | 99.45 | 99.79 | 100.0 | ID |

SEQUENCE LISTING

<160> NUMBER OF SEQ ID NOS: 15

<210> SEQ ID NO 1
<211> LENGTH: 11
<212> TYPE: DNA
<213> ORGANISM: Artificial Sequence
<220> FEATURE:
<223> OTHER INFORMATION: Synthetic

<400> SEQUENCE: 1
garactgrtt t                                                         11

<210> SEQ ID NO 2
<211> LENGTH: 22
<212> TYPE: DNA

```
<213> ORGANISM: Artificial Sequence
<220> FEATURE:
<223> OTHER INFORMATION: Synthetic

<400> SEQUENCE: 2
aacgaaagag gacgcgcccg aa                                              22

<210> SEQ ID NO 3
<211> LENGTH: 1471
<212> TYPE: DNA
<213> ORGANISM: Artificial Sequence
<220> FEATURE:
<223> OTHER INFORMATION: Synthetic

<400> SEQUENCE: 3
tggagagttt gatcctggct caggacgaac gctggcggcg tgcttaacac atgcaagtcg      60
agcgatgaag ctccttcggg agtggattag cggcggacgg gtgagtaaca cgtgggtaac     120
ctacctcaaa gaggggggata gcctcccgaa agggagatta ataccgcata ataatcagtt    180
ttcacatgga ractgrttta aaggagtaat ccgctttgag atggacccgc ggcgcattag     240
ctagttggta gggtaacggc ctaccaaggc gacgatgcgt agccgacctg agagggtgat     300
cggccacatt ggaactgaga cacggtccag actcctacgg gaggcagcag tgggaatat     360 tgcacaatgg gcgaaagcct gatgcagcaa cgccgcgtga gtgaagaagg ttttcggatt     420
gtaaagctct gtctttgggg acgataatga cggtacccaa ggaggaagcc acggctaact     480
acgtgccagc agccgcggta atacgtaggt ggcgagcgtt gtccggaatt actgggcgta     540
aagagtgcgt aggcggatat ttaagtgaga tgtgaaatac ccgggcttaa cccgggcact     600
gcatttcaaa ctggatatct agagtgcggg agaggagaat ggaattccta gtgtagcggt     660
gaaatgcgta gagattagga agaacaccag tggcgaaggc gattctctgg accgtaactg     720
acgctgaggc acgaaagcgt gggtagcaaa caggattaga taccctggta gtccacgccg     780
taaacgatga gtactaggtg taggaggtat cgacccctttc tgtgccgcag taaacacaat     840
aagtactccg cctgggaagt acgatcgcaa gattaaaaact caaaggaatt gacggggcc     900 cgcacaagca gcggagcatg tggtttaatt cgaagcaacg cgaagaacct tacctggact    960
tgacataccc tgaatatctt agagataaga gaagcccttc ggggcaggga tacaggtggt    1020
gcatggttgt cgtcagctcg tgtcgtgaga tgttaggtta gtcctgcaa cgagcgcaac    1080 ccctgttgtt agttgctaac atttagttga gcactctagc aagactgccg cggttaacgc    1140
ggaggaaggt ggggatgacg tcaaatcatc atgcccctta tgtccagggc aacacacgtg    1200
ctacaatggg cagtacagag agaagcaaga ycgcaaggtg gagcaaacct caaaaactgc    1260
ccccagttcg gattgcaggc tgaaactcgc ctacatgaag ttggagttgc tagtaatcgc    1320
gaatcagaat gtcgcggtga atacgttccc gggccttgta cacaccgccc gtcacaccat    1380
gagagctggc aacacccgaa gtccgtagtc taacgaaaga gacgcggcc gaaggtgggg    1440 ttagtaattg gggtgaagtc gtaacaaggt a                                  1471

<210> SEQ ID NO 4
<211> LENGTH: 36
<212> TYPE: DNA
<213> ORGANISM: Artificial Sequence
<220> FEATURE:
<223> OTHER INFORMATION: Synthetic

<400> SEQUENCE: 4
tcagttttca catggaract grtttaaagg agtaat                               36
```

<210> SEQ ID NO 5
<211> LENGTH: 36
<212> TYPE: DNA
<213> ORGANISM: Artificial Sequence
<220> FEATURE:
<223> OTHER INFORMATION: Synthetic

<400> SEQUENCE: 5
tcagttttca catggagact gatttaaagg agtaat         36

<210> SEQ ID NO 6
<211> LENGTH: 36
<212> TYPE: DNA
<213> ORGANISM: Artificial Sequence
<220> FEATURE:
<223> OTHER INFORMATION: Synthetic

<400> SEQUENCE: 6
tcagttttca catggraatt gatttaaagg agtaat         36

<210> SEQ ID NO 7
<211> LENGTH: 36
<212> TYPE: DNA
<213> ORGANISM: Artificial Sequence
<220> FEATURE:
<223> OTHER INFORMATION: Synthetic

<400> SEQUENCE: 7
tcagttttca catggarayt gatttaaagg agtaat         36

<210> SEQ ID NO 8
<211> LENGTH: 36
<212> TYPE: DNA
<213> ORGANISM: Artificial Sequence
<220> FEATURE:
<223> OTHER INFORMATION: Synthetic

<400> SEQUENCE: 8
tcagttttca catggagatt gatttaaagg agtaat         36

<210> SEQ ID NO 9
<211> LENGTH: 36
<212> TYPE: DNA
<213> ORGANISM: Artificial Sequence
<220> FEATURE:
<223> OTHER INFORMATION: Synthetic

<400> SEQUENCE: 9
tcagttttca catggagact gatttaaagg agtaat         36

<210> SEQ ID NO 10
<211> LENGTH: 36
<212> TYPE: DNA
<213> ORGANISM: Artificial Sequence
<220> FEATURE:
<223> OTHER INFORMATION: Synthetic

<400> SEQUENCE: 10
gtctaacgaa agaggacgcg gccgaaggtg gggtta         36

<210> SEQ ID NO 11
<211> LENGTH: 36
<212> TYPE: DNA
<213> ORGANISM: Artificial Sequence
<220> FEATURE:
<223> OTHER INFORMATION: Synthetic -continued

```
<400> SEQUENCE: 11
gtctaactta ggaggacgcg gccgaaggtg gggtta                              36

<210> SEQ ID NO 12
<211> LENGTH: 19
<212> TYPE: DNA
<213> ORGANISM: Artificial Sequence
<220> FEATURE:
<223> OTHER INFORMATION: Synthetic

<400> SEQUENCE: 12
gtctaccgaa agaggacgc                                                 19

<210> SEQ ID NO 13
<211> LENGTH: 36
<212> TYPE: DNA
<213> ORGANISM: Artificial Sequence
<220> FEATURE:
<223> OTHER INFORMATION: Synthetic

<400> SEQUENCE: 13
gtctacctga ggaggacgcc gcccsawgtt gkkawa                              36

<210> SEQ ID NO 14
<211> LENGTH: 36
<212> TYPE: DNA
<213> ORGANISM: Artificial Sequence
<220> FEATURE:
<223> OTHER INFORMATION: Synthetic

<400> SEQUENCE: 14
gtctaactta ggaggacgcg gccgaaggtg gggtta                              36

<210> SEQ ID NO 15
<211> LENGTH: 36
<212> TYPE: DNA
<213> ORGANISM: Artificial Sequence
<220> FEATURE:
<223> OTHER INFORMATION: Synthetic

<400> SEQUENCE: 15
gtctaactta ggaggacgcg gccgaaggtg gggtta                              36
```

US 8,143,037 B2

ETHANOLOGENIC *CLOSTRIDIUM* SPECIES, *CLOSTRIDIUM COSKATII*

SEQUENCE LISTING STATEMENT

The sequence listing is filed in this application in electronic format only and is incorporated by reference herein. The sequence listing text file "09-1202_SequenceListing.txt" was created on Apr. 12, 2010, and is 4,863 bytes in size.

FIELD OF THE INVENTION

The field of the invention relates to a novel bacterial species that is capable of producing ethanol from gas mixtures consisting of hydrogen ($H_2$) and carbon dioxide ($CO_2$), and/or carbon monoxide (CO). In particular, the invention provides a novel *Clostridium* species, *Clostridium coskatii* (PS02), having the identifying characteristics of ATCC No. PTA-10522 and a method of synthesizing ethanol and other useful products from $H_2$ and/or $CO_2$, and/or CO gas using this novel *Clostridium* species.

BACKGROUND OF THE INVENTION

Currently, the major mode of biofuel production (production of fuel, such as ethanol, from biomass) is through direct fermentation, which accounts for 90% of the ethanol output in the U.S. (Licht, F. O. (2001) World Ethanol Markets, Analysis and Outlook, Kent, UK). Direct fermentation is the process in which a saccharolytic microorganism, such as yeast or bacteria, converts sugars to ethanol. These sugars may be simple (i.e. glucose) or complex (i.e. starch, cellulose, hemicellulose). Corn starch is the primary substrate used in ethanol producing plants today. One disadvantage of the use of corn starch in the direct fermentation production of ethanol is that corn is a component of many human and animal foods. Therefore, the use of the corn for the production of ethanol takes it out of the supply for human and animal consumption.

Other substrates, such as lignocellulosic biomass (i.e. grasses, small trees, paper waste, or saw dust), are also being researched for use in direct fermentation of biofuels. However, they also have limitations. Lignocellulose is comprised of cellulose, hemicellulose, pectin, and lignin, which require pretreatment processes to break down the biomass into its individual sugar components before microorganisms can utilize the substrate. This adds more cost in the areas of materials, plant design, and waste management. Furthermore, approximately 22-35% of the lignocellulose fraction is composed of lignin, which cannot be utilized by current direct fermentation approaches, and is discarded from the process as a recalcitrant waste material.

Another alternative method of biofuel production is indirect fermentation. Indirect fermentation is the process in which energy-rich gases which can provide an electron source, such as $H_2$ and CO, and carbon sources, such as CO and $CO_2$ are generated from carbon-containing, non-food agricultural and industrial waste material, and then are transferred to a bioreactor where anaerobic bacteria convert the gases to biofuels. The gases produced when lignocellulosic biomass is pyrolyzed (burned) would be an example of a type of waste gas that may be utilized in indirect fermentation. Synthesis gas (also referred to as "syngas") (primarily CO, $H_2$, and $CO_2$) is a product of pyrolyzed biomass or coal and has been recognized for its potential role in the indirect fermentation of biomass to fuel alcohol (Zeikus, J. G, Annu Rev. Microbiol. 34:423-464 (1980). Another source of energy-rich waste gas is the basic oxygen steelmaking (LD converter) process, which produces a significant volume of waste gas consisting of 70% CO, 1-2% $H_2$, and 10-15% $CO_2$, which is also suitable for producing biofuels using the indirect fermentation process.

Anaerobic microorganisms such as acetogenic bacteria offer a viable route to convert waste gases to useful products, such as ethanol and n-butanol, via the indirect fermentation process. Such bacteria catalyze the conversion of $H_2$ and $CO_2$ and/or CO to biofuels with higher specificity, higher yields and lower energy costs than can be attained by the Fischer-Tropsch process, or other chemical biofuel production processes that use CO and $H_2$. Several microorganisms capable of producing biofuels from waste gases and other substrates have been identified and are discussed below.

Six acetogenic bacteria have been described for use in the production of the biofuels, ethanol, n-butanol, or mixtures of these alcohols using at least one of the three main components of syngas ($H_2+CO_2$, or CO, or $H_2+CO_2$ and CO) as substrates. These include *Butyribacterium methylotrophicum* (Grethlein et al., 1990; Jain et al., 1994b), *Clostridium ragsdalei* (Huhnke et al., 2008), *Clostridium carboxidivorans* (Liou, et al., 2005), *Moorella* species HUC22-1 (Inokuma, et al., 2007), *Clostridium autoethanogenum* (Abrini et al., 1994), and *Clostridium ljungdahlii* (Arora et al, 1995; Batik et al., 1988; Batik et al. 1990; and Tanner et al., 1993). Of these representatives, only three—*Clostridium ljungdahlii*, *Clostridium ragsdalei*, and *Clostridium autoethanogenum*—are known to convert CO, or mixtures of CO and/or $H_2$ and $CO_2$ to acetic acid and ethanol. Thus, they are the only known organisms capable of forming a single alcohol (ethanol) end product, while simultaneously using all components of a synthesis gas stream. This group of bacteria, referred to in this document as the clostridial ethanologens, have significant commercial importance because the economics of the indirect fermentation process is advantaged by: (a) co-utilization of $H_2$ and CO, so that the combined conversion rate exceeds 90%, and (b) production of a single alcohol, which permits the use of a simplified and less expensive biofuel recovery system.

Six clostridial ethanologens have been described in literature for the production of biofuels from synthesis gas:

(1) *Clostridium ljungdahlii* PETC$^T$ (ATCC No. 49587 and DSMZ No. 13528): This organism is the original type strain deposit for this species (Tanner et al., 1993). See U.S. Pat. No. 5,173,429.

(2) *Clostridium ljungdahlii* ERI-2 (ATCC No. 55380): The phylogenetic status of this organism remains unclear since it is apparently not identical to the PETC type strain, but is not included on the list of Approved Lists of Bacterial Names (Skerman et al., 1989). See U.S. Pat. No. 5,593,886.

(3) *Clostridium ljungdahlii* C-01; (ATCC No. 55988): The phylogenetic status of this organism remains unclear since it is apparently not identical to the PETC type strain, but is not included on the list of Approved Lists of Bacterial Names (Skerman et al., 1989). See U.S. Pat. No. 6,136,577.

(4) *Clostridium ljungdahlii* O-52; (ATCC No. 55989): The phylogenetic status of this organism remains unclear since it is apparently not identical to the PETC type strain, but is not included on the list of Approved Lists of Bacterial Names (Skerman et al., 1989). See U.S. Pat. No. 6,136,577.

(5) *Clostridium ragsdalei*; (ATCC No. BAA-622): See U.S. Pat. No. US20080057554 (EP2061872A2).

(6) *Clostridium autoethanogenum*; (DSMZ No. 10061) This isolate was described by Abrini et al., 1994 as producing ethanol and acetate from mixtures of CO, $H_2$, and $CO_2$.

In addition to patents describing the use of specific ethanologenic clostridia for biofuel production, as defined above, the following process patents exist for producing biofuels from waste gases such as synthesis gas. Certain patents also cover microorganisms known to produce multiple alcohols (primarily ethanol and n-butanol) from waste gases (e.g., *Clostridium carboxidivorans*):

(1) U.S. Pat. No. US20070275447A1 to Lewis et al. discloses *Clostridium carboxidivorans* ATCC No. BAA-624, a novel anaerobic clostridia bacterial species that is capable of synthesizing biofuels, including ethanol and n-butanol from waste gases such as synthesis gas.

(2) U.S. Pat. No. 5,192,673 to Jain et al. discloses a mutant strain of *Clostridium acetobytylicum* and a process for making butanol with the strain.

(3) U.S. Pat. No. 5,593,886 to Gaddy et al. discloses a process using *Clostridium ljungdahlii* ATCC No. 55380 for producing acetate and ethanol using waste gas (e.g. carbon black waste gas) as a substrate.

(4) U.S. Pat. No. 5,807,722 to Gaddy et al. discloses a method and apparatus for converting waste gases into useful products such as organic acids and alcohols using anaerobic bacteria, such as *Clostridium ljungdahlii* ATCC No. 55380.

(5) U.S. Pat. No. 6,136,577 to Gaddy et al. discloses a method and apparatus for converting waste gases into useful products such as organic acids and alcohols (particularly ethanol) using anaerobic bacteria, such as *Clostridium ljungdahlii* ATCC Nos. 55988 and 55989.

(6) U.S. Pat. No. 6,136,577 to Gaddy et al. discloses a method and apparatus for converting waste gases into useful products such as organic acids and alcohols (particularly acetic acid) using anaerobic strains of *Clostridium ljungdahlii*.

(7) U.S. Pat. No. 6,753,170 to Gaddy et al. discloses an anaerobic microbial fermentation process for the production of acetic acid.

(8) U.S. Pat. No. 7,285,402 to Gaddy et al. discloses an anaerobic microbial fermentation process for the production of ethanol.

Despite the knowledge in the art regarding the use of microorganisms in the production of biofuels, there remains an ongoing need to discover and/or develop additional microorganisms that are capable of producing useful products such as biofuels using the indirect fermentation process. In particular, it would be advantageous to discover new ethanologenic clostridia that exhibit improved growth characteristics and high biofuel yields when cultivated under chemically-defined or low organic carbon growth conditions. Specifically, elimination of complex organic carbon sources such as yeast extract, beef extract, corn steep liquor, or soy tryptones from the bacterial growth medium could be considered desirable for production of biofuels via synthesis gas fermentation because (1) these components add additional expense to the biofuels production cost, and (2) complex organic carbon sources support foreign bacterial growth in the biofuels production fermentors, which negatively impacts biofuel yield and process economics.

SUMMARY OF INVENTION

The present invention is directed to a biologically pure culture of a newly discovered ethanologenic Clostridia species, *Clostridium coskatii* (PS02). This Clostridia species is a new Clostridia species with distinguishing phenotypic and genetic characteristics from other known Clostridia species.

Another embodiment of the present invention is the unique capability of this Clostridia species to produce ethanol and acetate from gaseous sources of CO and/or $H_2$ and/or $CO_2$.

In another embodiment of the present invention, the *Clostridium coskatii* is uniquely capable of ethanol production in the absence of complex organic carbon sources, such as yeast extract.

BRIEF DESCRIPTION OF DRAWINGS

FIG. 7b provides a matrix of correlation coefficients summarizing the strength of the linear relationships in fatty acid methyl ester profiles of FIG. 7a.

FIG. 7c illustrates a scatterplot matrix showing the strength of the linear relationships in fatty acid methyl ester profiles of FIG. 7b; α=0.99.

FIG. 8a illustrates SEQ ID NO. 3, which is the 16S rDNA sequence for *Clostridium coskatii*. Gaps in the contiguous sequence were generated by alignment to sequences shown in FIG. 8b.

FIG. 9 illustrates a 16S rDNA neighbor phylogenetic tree distance matrix scores showing similarity of the 16S rDNA sequence for ethanologenic clostridia.

ATCC 55988; (7) *C. ljungdahlii* ERI-2 ATCC 55380; (8) 100 bp ladder; (9) pUC19/Sau3A marker.

Figure 12:
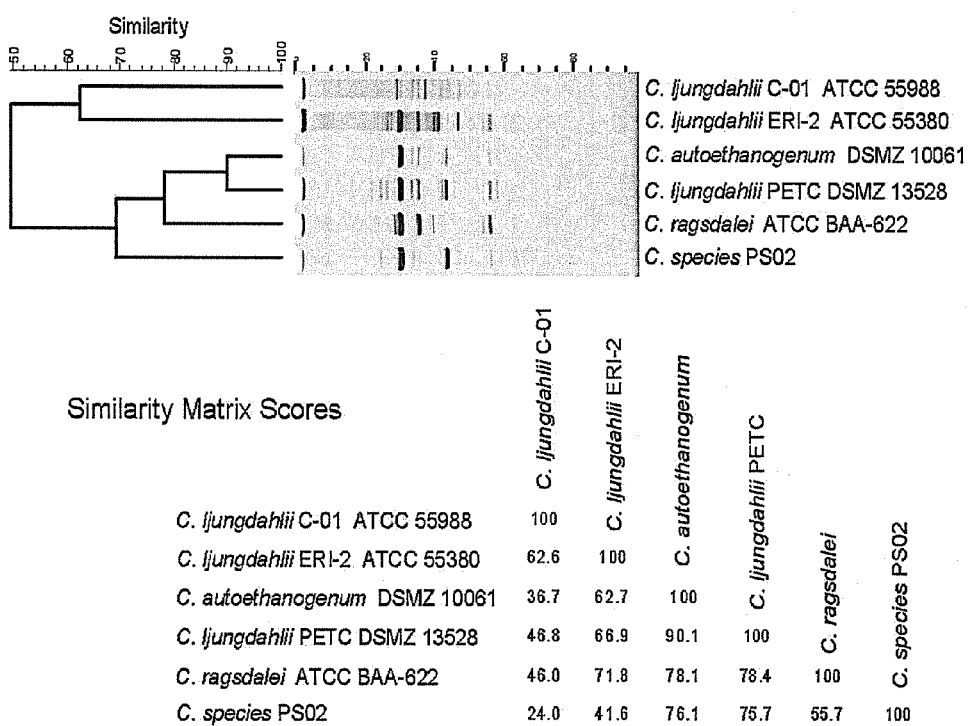

FIG. 12 illustrates a Parsimony tree and Pearson UPGMA similarity matrix scores for the analysis of amplicons generated by BOX-PCR for ethanologenic clostridial species.

Figure 13:
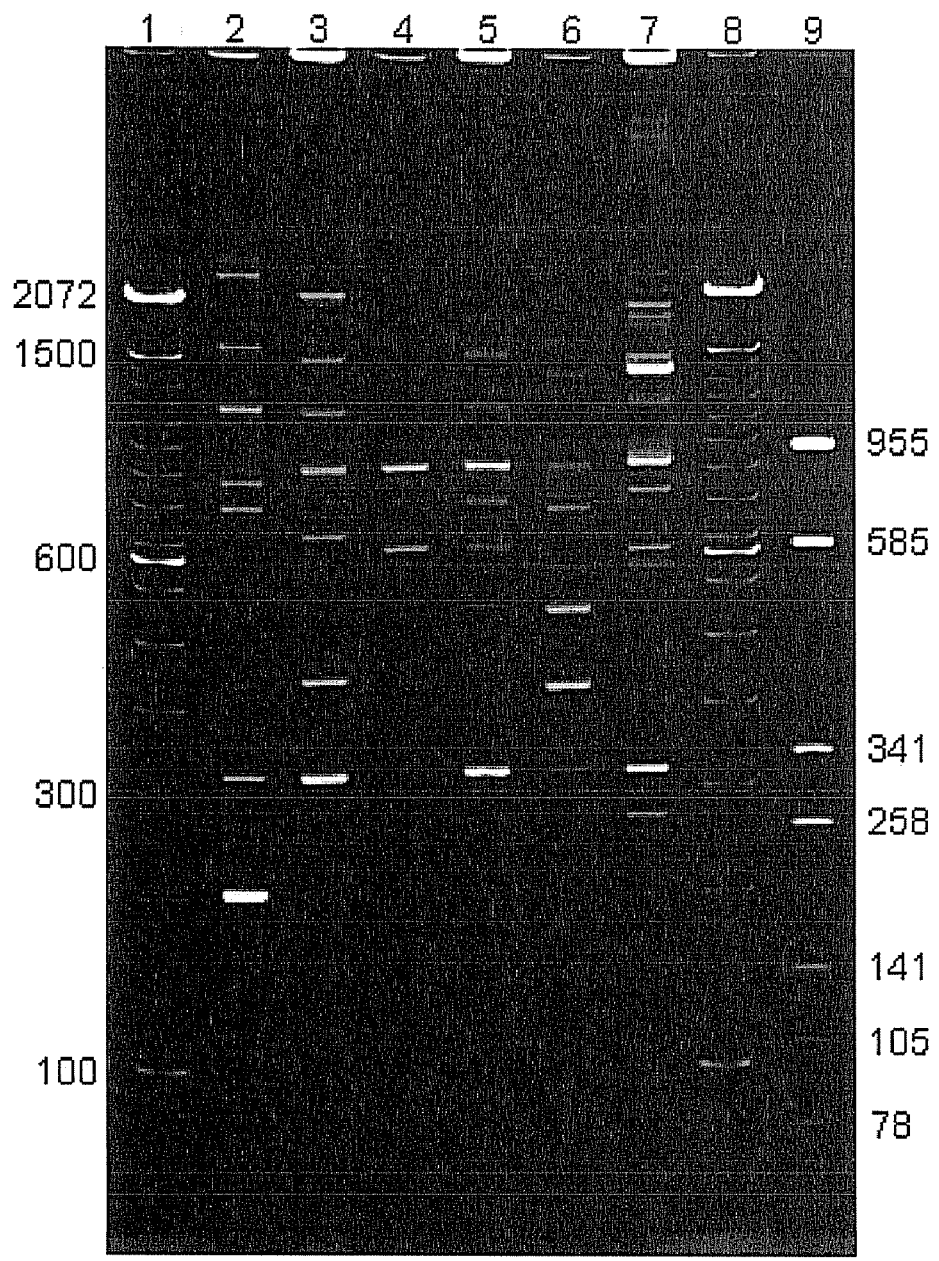

FIG. 13 illustrates a REP-PCR comparison of ethanologenic clostridial species. Lane assignments are: (1) 100 bp ladder; (2) *C. coskatii* (PS02); (3) *C. ragsdalei* ATCC BAA-622; (4) *C. autoethanogenum* DSMZ 10061; (5) *C. ljungdahlii* PETC DSMZ 13528; (6) *C. ljungdahlii* C-01 ATCC 55988; (7) *C. ljungdahlii* ERI-2 ATCC 55380; (8) 100 bp ladder; (9) pUC19/Sau3A marker.

Figure 14:
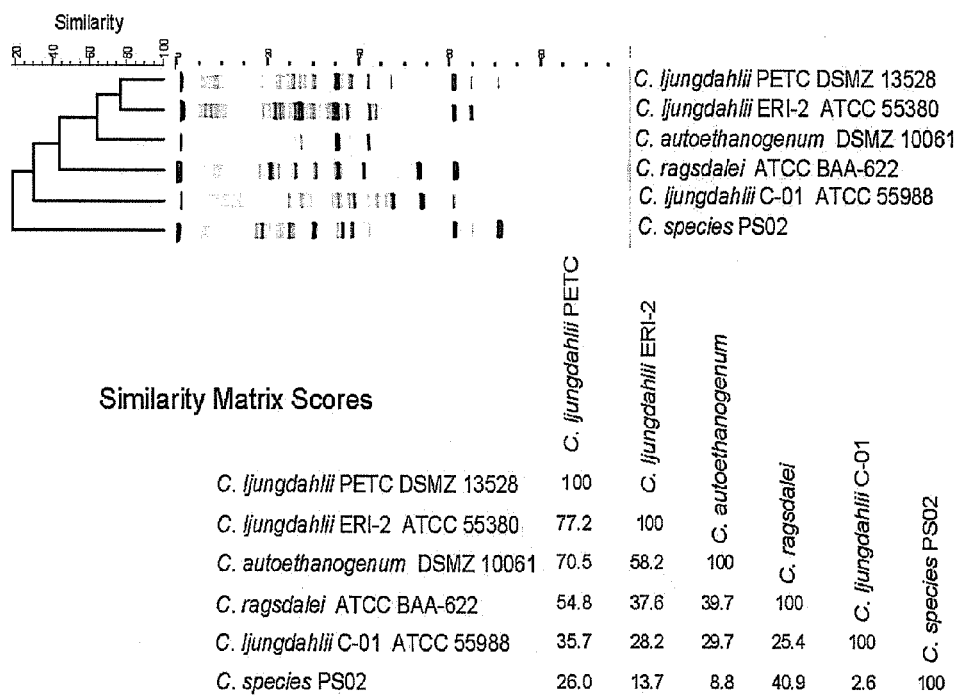

FIG. 14 illustrates a Parsimony tree and Pearson UPGMA similarity matrix scores for the analysis of amplicons generated by REP-PCR for ethanologenic clostridial species.

Figure 15:
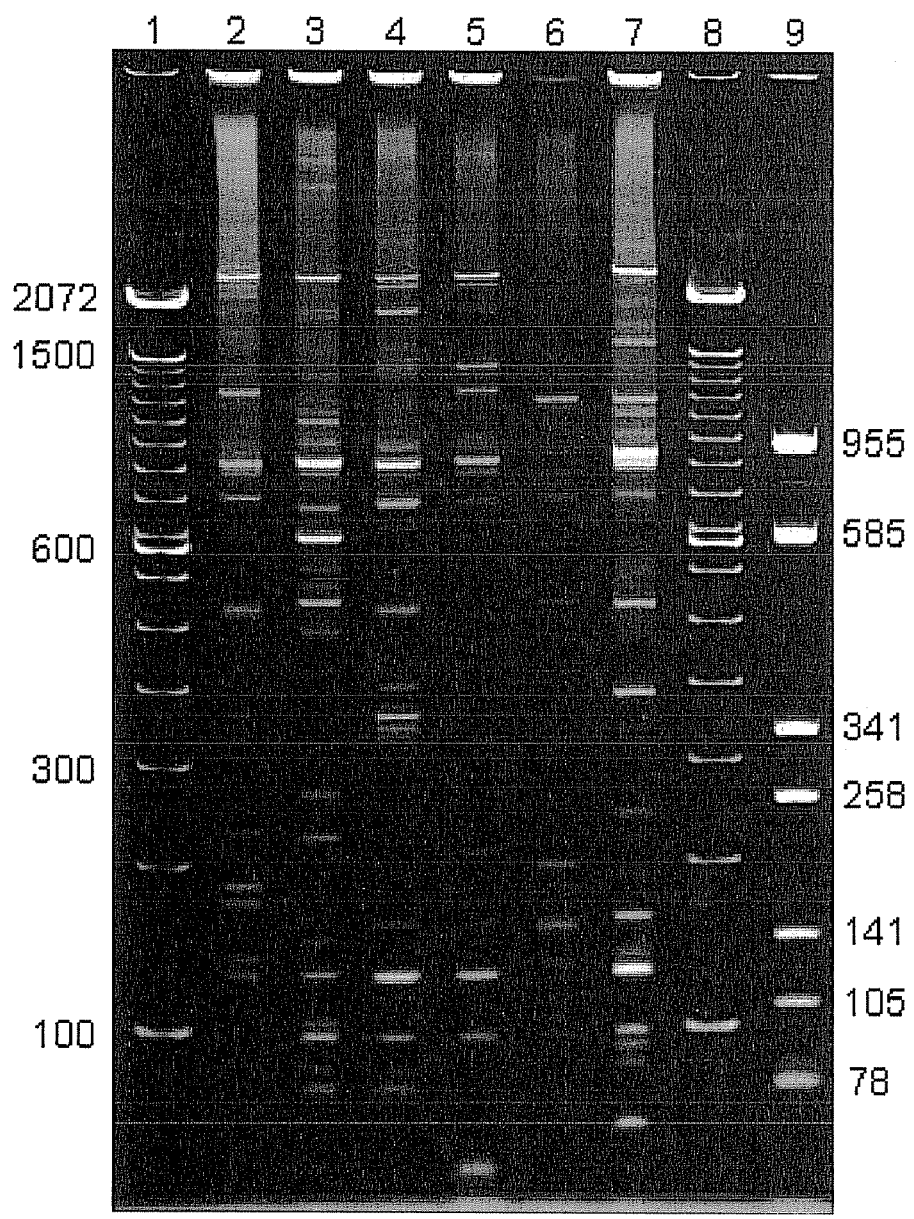

FIG. 15 illustrates an ERIC-PCR comparison of ethanologenic clostridial species. Lane assignments are: (1) 100 bp ladder; (2) *C. coskatii* (PS2); (3) *C. ragsdalei* ATCC BAA-622; (4) *C. autoethanogenum* DSMZ 10061; (5) *C. ljungdahlii* PETC DSMZ 13528; (6) *C. ljungdahlii* C-01 ATCC 55988; (7) *C. ljungdahlii* ERI-2 ATCC 55380; (8) 100 bp ladder; (9) pUC19/Sau3A marker.

Figure 16:
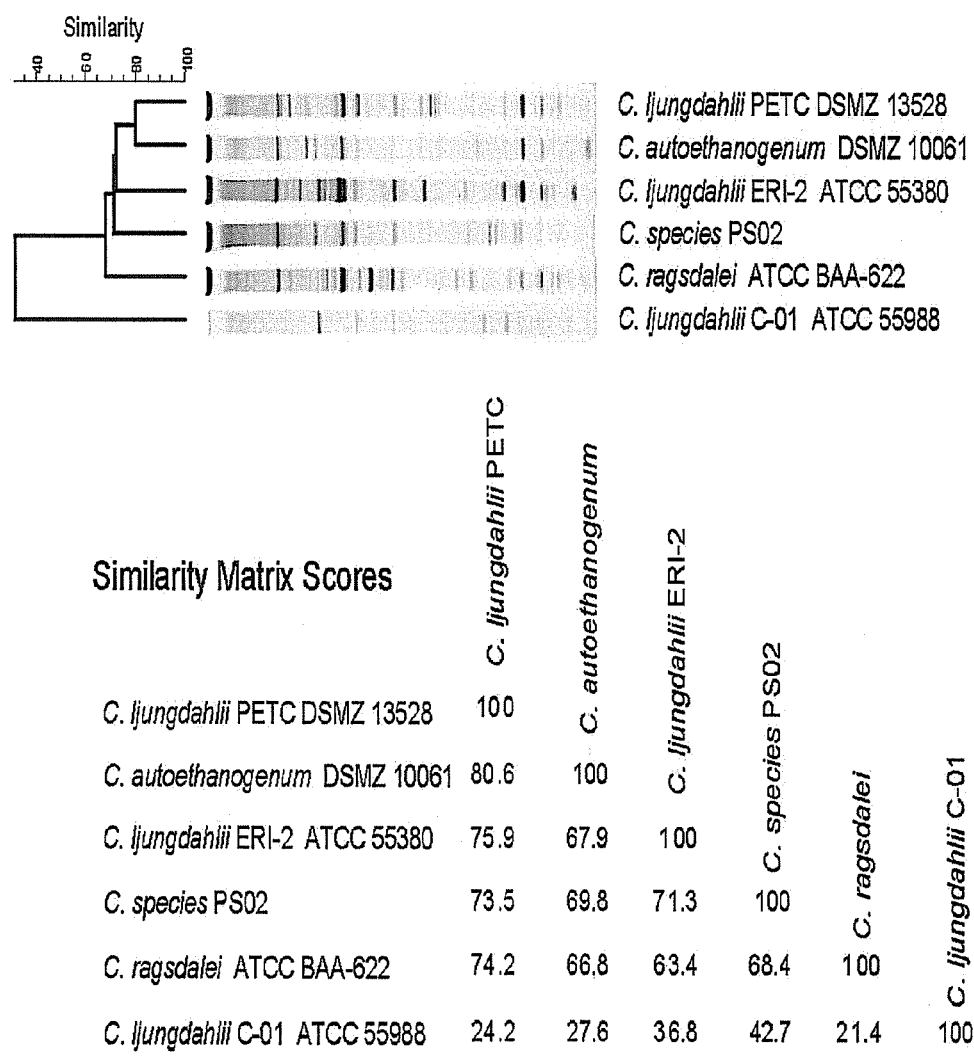

FIG. 16 illustrates a Parsimony tree and Pearson UPGMA similarity matrix scores for the analysis of amplicons generated by ERIC-PCR for ethanologenic clostridial species.

Figure 17:
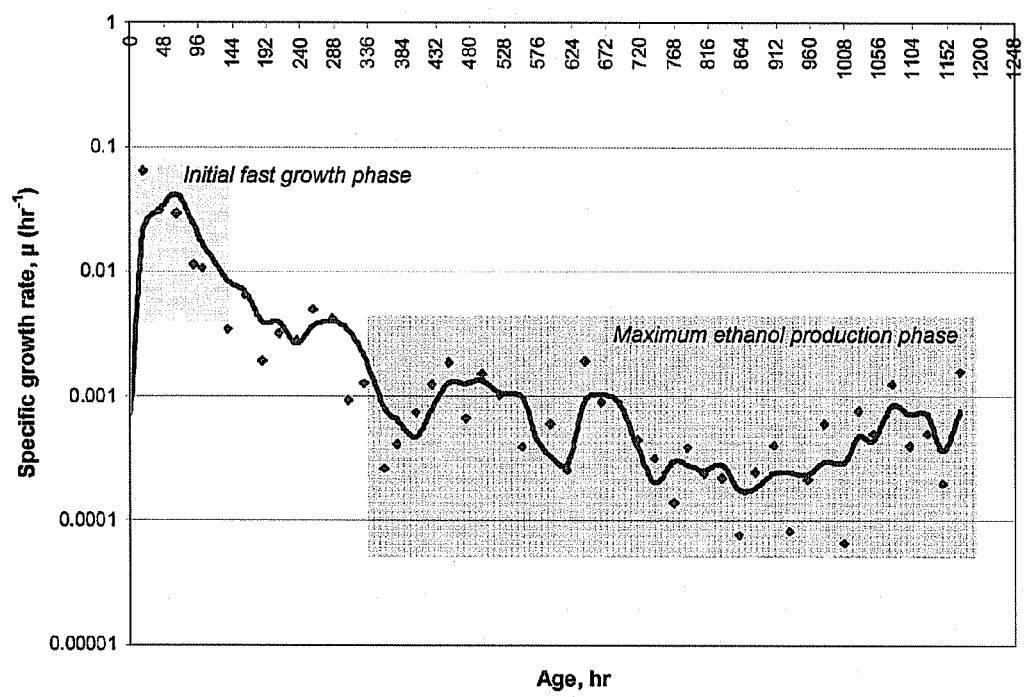

FIG. 17 illustrates specific growth rate measurements of *Clostridium coskatii* (PS02) when using Acetogen C5 media and in a synthesis gas-fed CSTR: (a) under pre-steady state conditions (exponential growth phase), and (b) under ethanol production phase (late exponential to stationary phase) using a mean cell retention time of 2.0 days. Duration=43.75 days.

Figure 18:
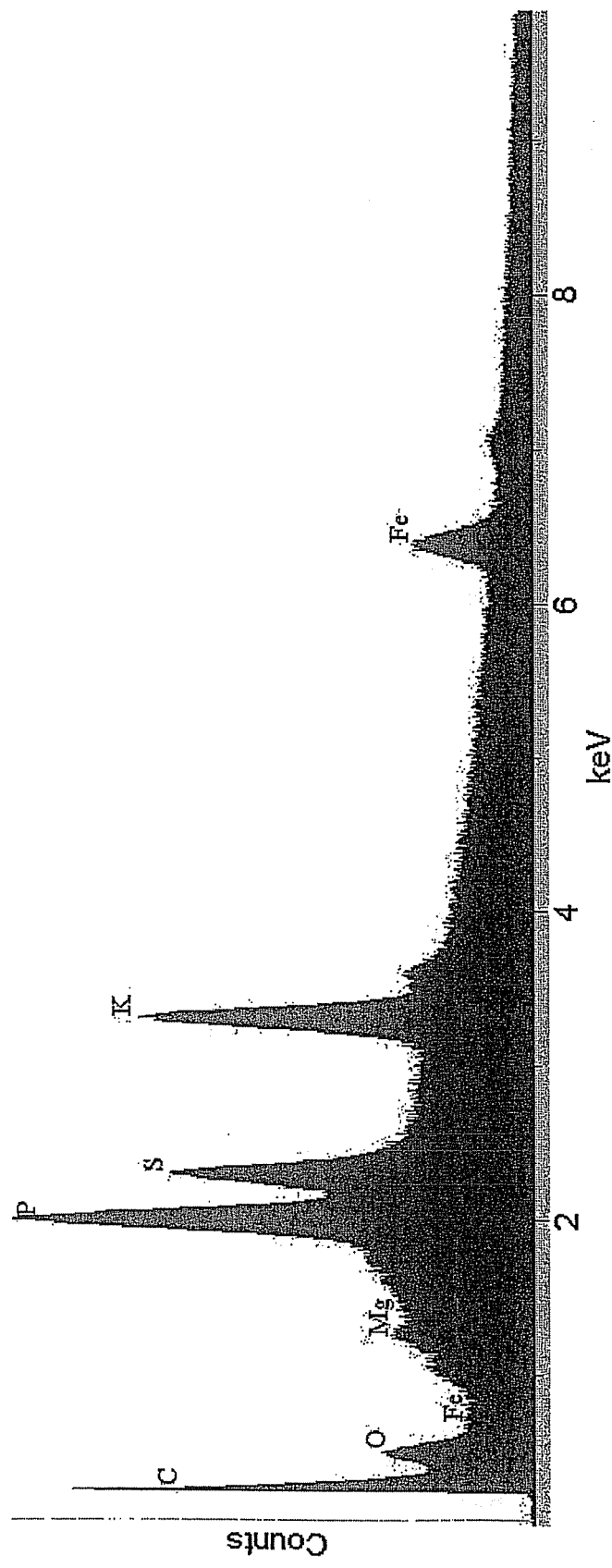

FIG. 18 is an X-ray spectrum showing the major elements present in *Clostridium coskatii* (PS02) cells.

Figure 19:
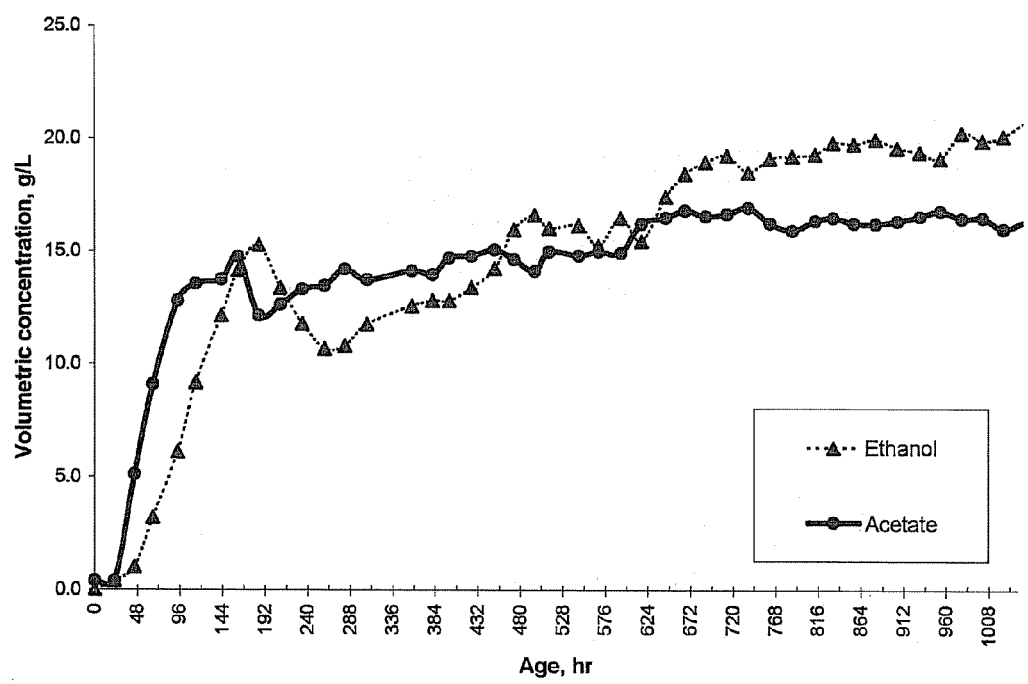

FIG. 19 illustrates the volumetric concentration of ethanol and acetate produced in a synthesis gas-fed CSTR using Acetogen C5 media, using a 2.0 day mean cell retention time, and containing *Clostridium coskatii* (PS02). Duration=43.75 days.

Figure 20:
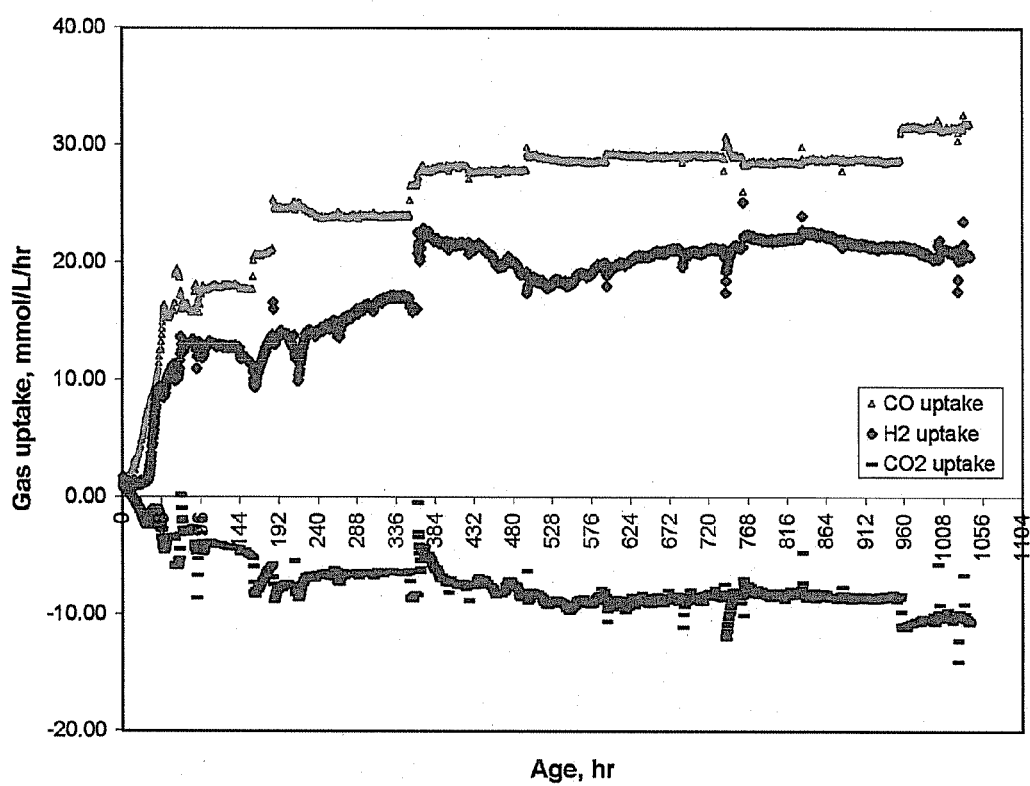

FIG. 20 illustrates the gas uptake rate for a synthesis gas-fed CSTR (products shown in FIG. 21) when using Ethanologen C5 media, a 2.0 day mean cell retention time, and containing *Clostridium coskatii* (PS02). Duration=43.75 days.

Figure 21:
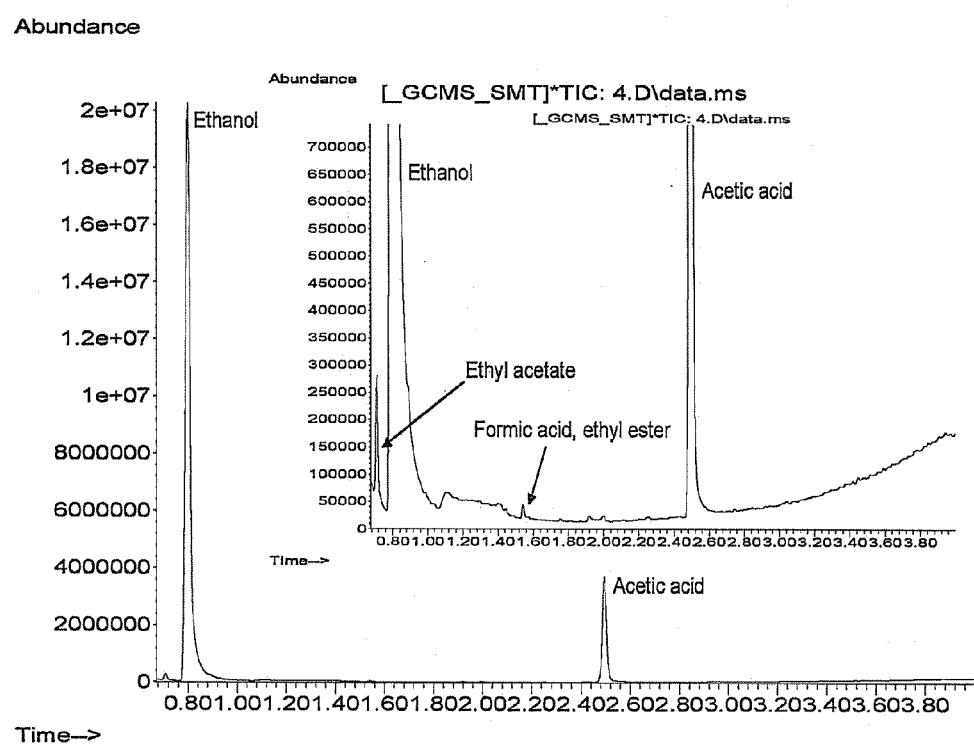

FIG. 21 illustrates the GC-MS total ion current (TIC) chromatogram of volatiles present in the broth phase of a syngas fermentation at a steady-state growth for *Clostridium coskatii* (PS02). Inset: 28-fold magnification of the chromatographic baseline showing trace impurities generated through metabolism (formic acid, ethyl ester) or acid-catalyzed chemical reaction (ethyl acetate).

Figure 22A:
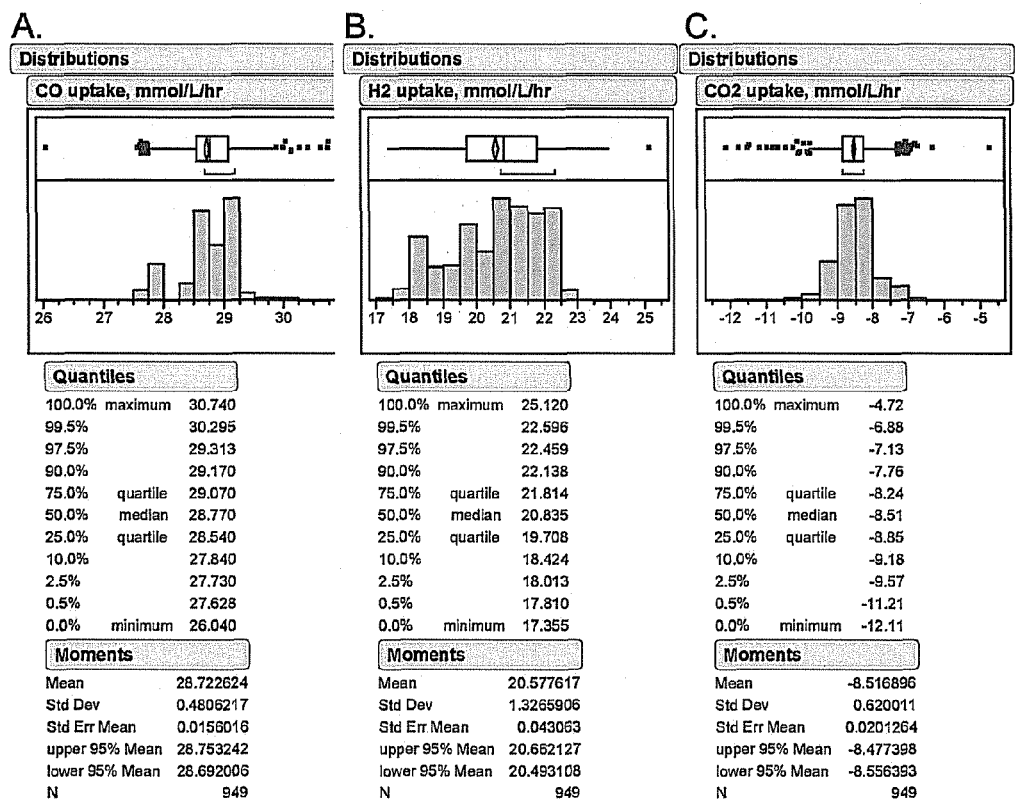

FIG. 22a: Statistical analysis for the average gas uptake rate for a 470 hour steady-state period in a synthesis gas-fed CSTR using Acetogen C5 media, a 2.0 day mean cell retention time, and containing *Clostridium coskatii* (PS02). Duration=43.75 days. A) CO uptake, B) $H_2$ uptake, and C) $CO_2$ uptake.

Figure 22B:
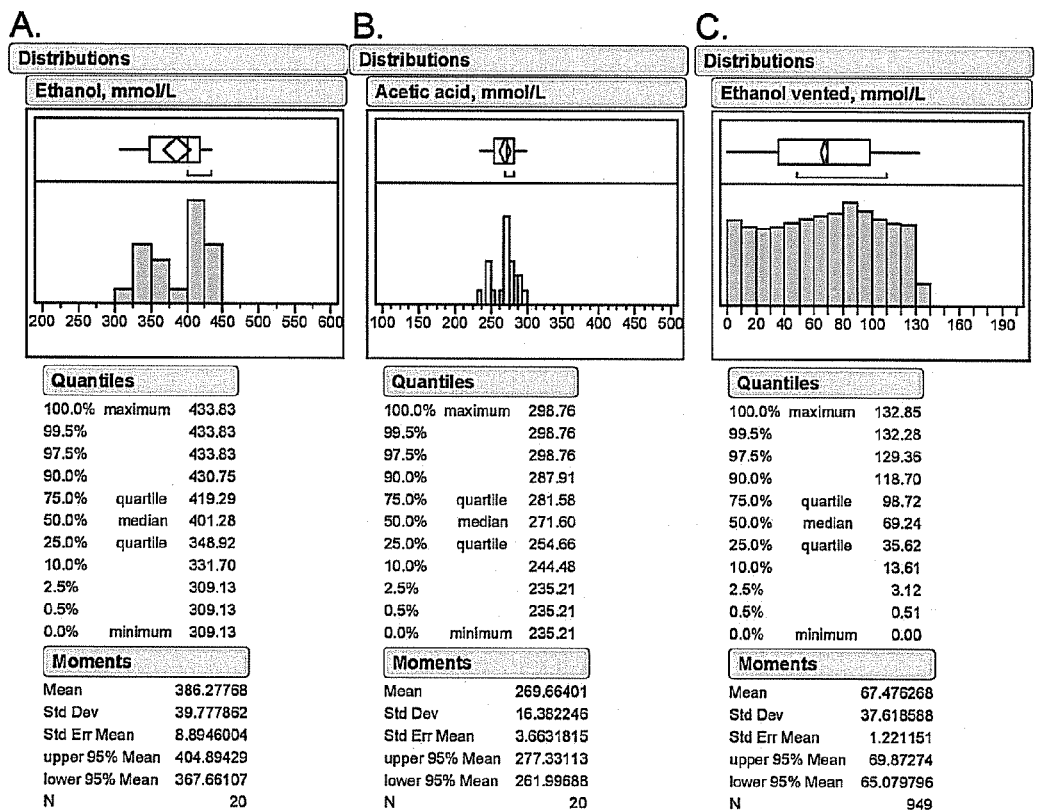

FIG. 22b illustrates a continuation of the statistical analysis for the average gas uptake rate for a 470 hour steady-state period in a synthesis gas-fed CSTR using Acetogen C5 media, a 2.0 day mean cell retention time, and containing *Clostridium coskatii* (PS02). Duration=43.75 days. A) Volumetric ethanol concentration in mmol/L, B) Volumetric ethanol concentration in mmol/L, and C) total ethanol vented from the broth in mmol/L.

Figure 23:
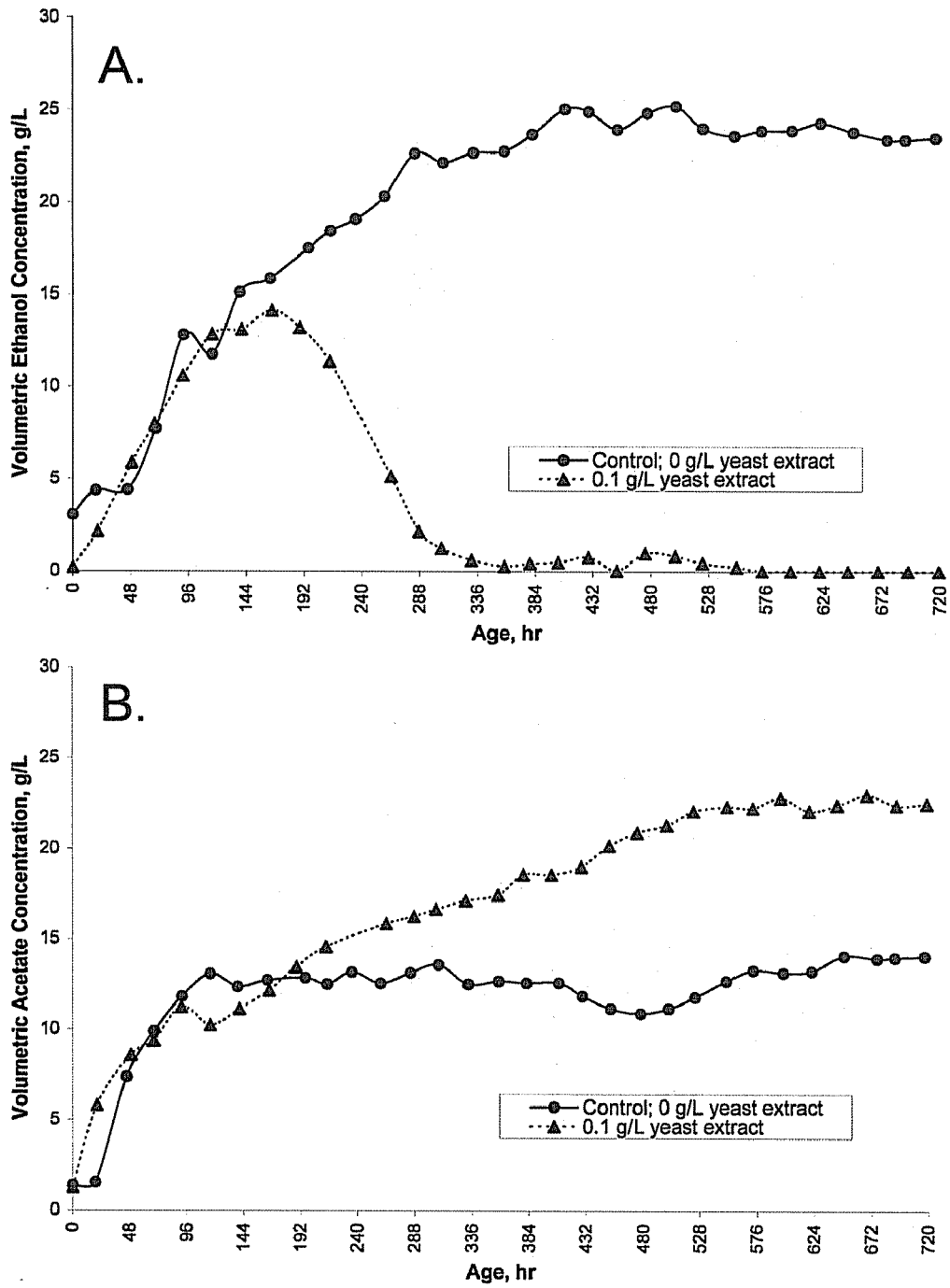
Figure 1:
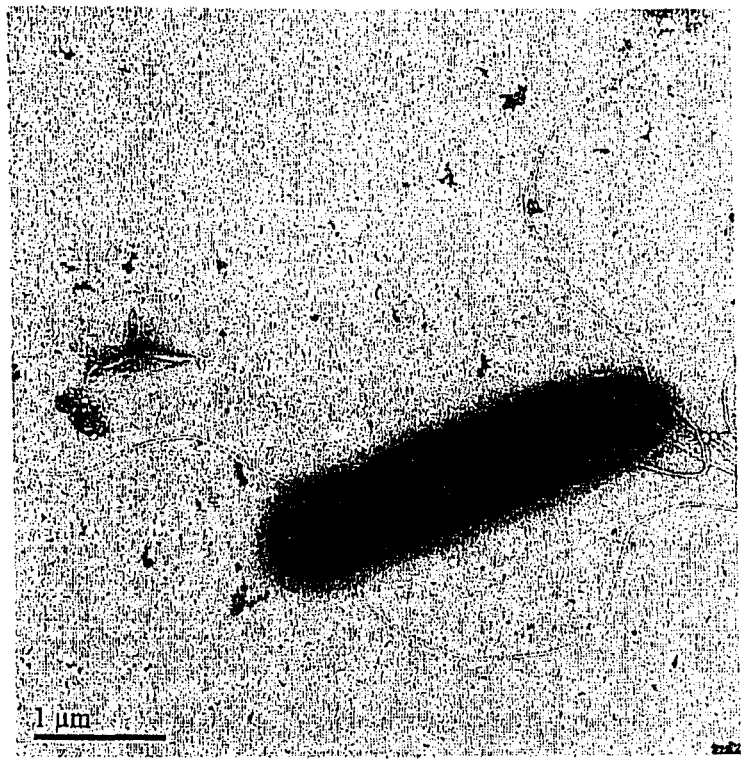
Figure 2:
Figure 3:
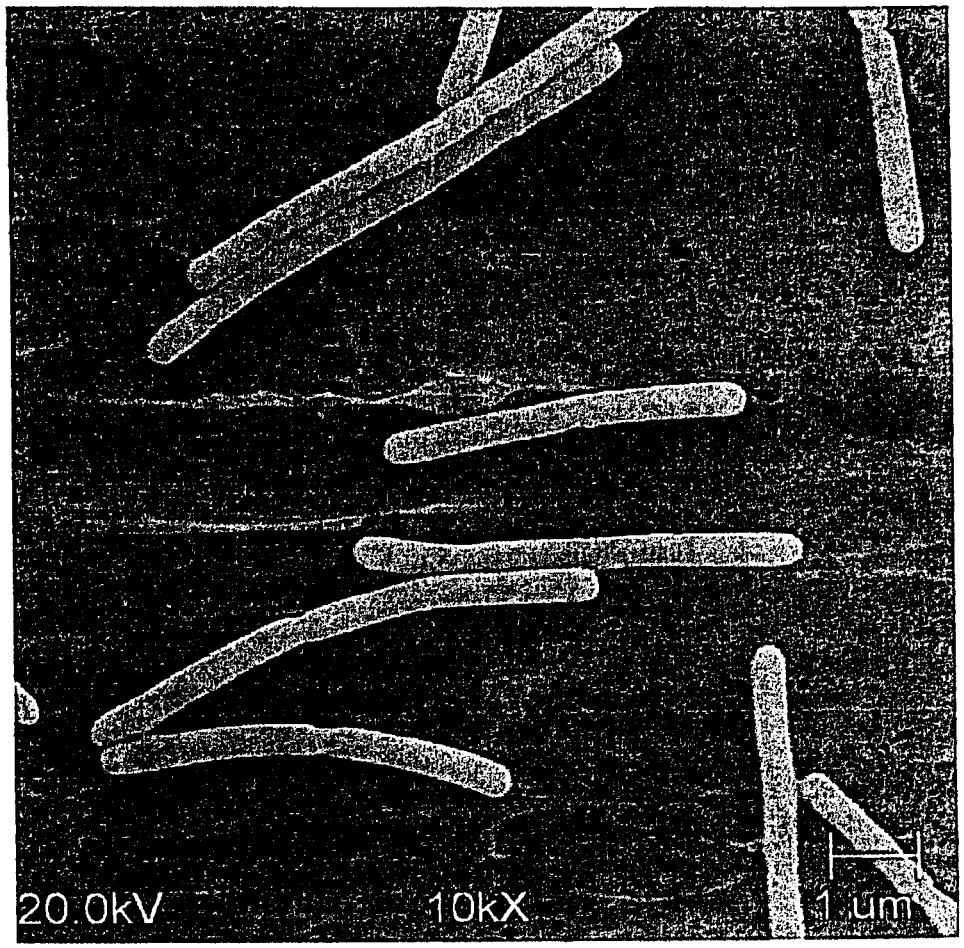
Figure 4:
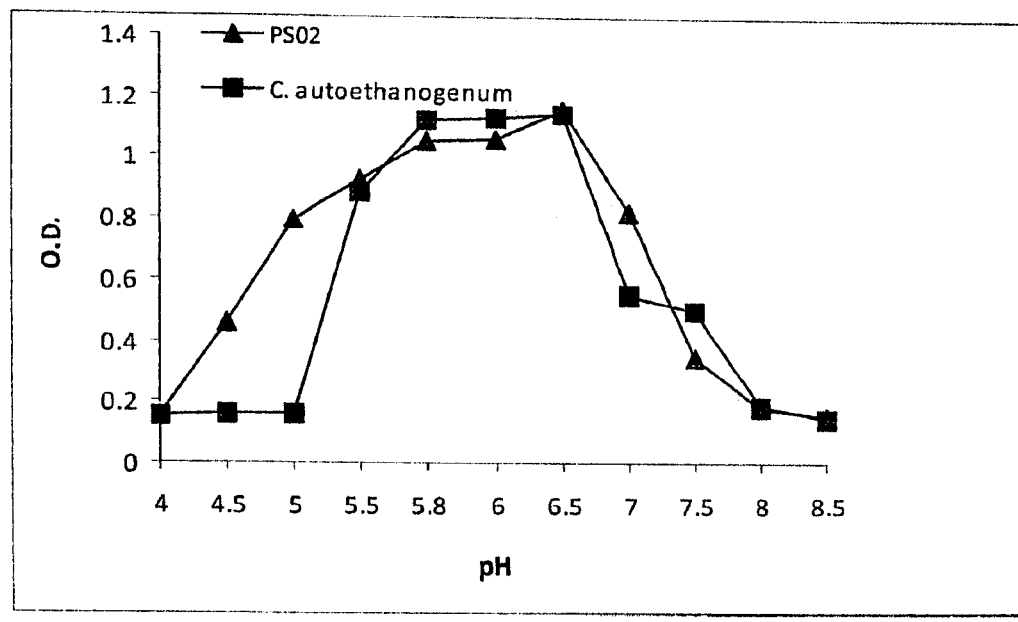
Figure 5:
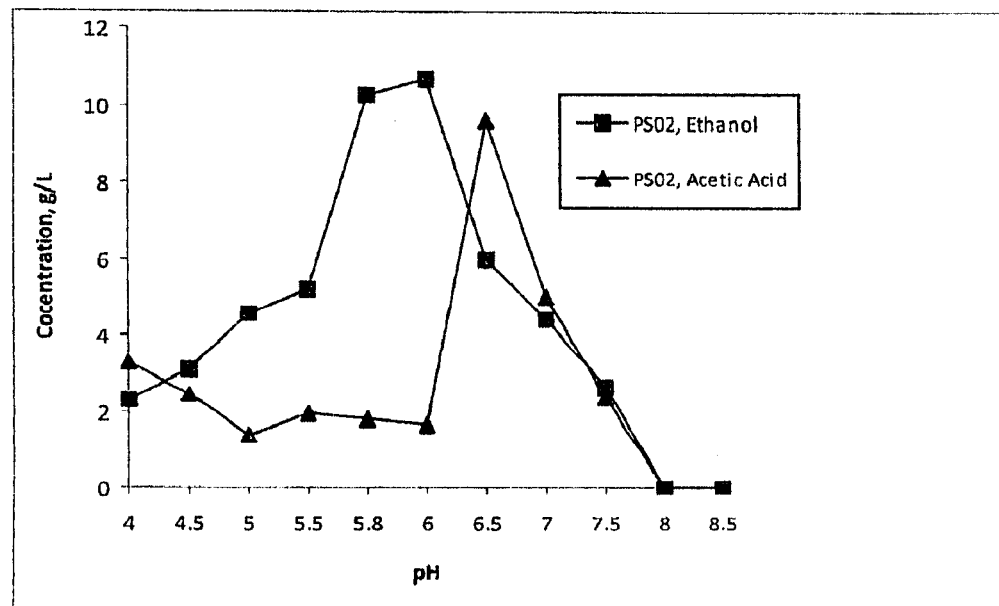
Figure 6:
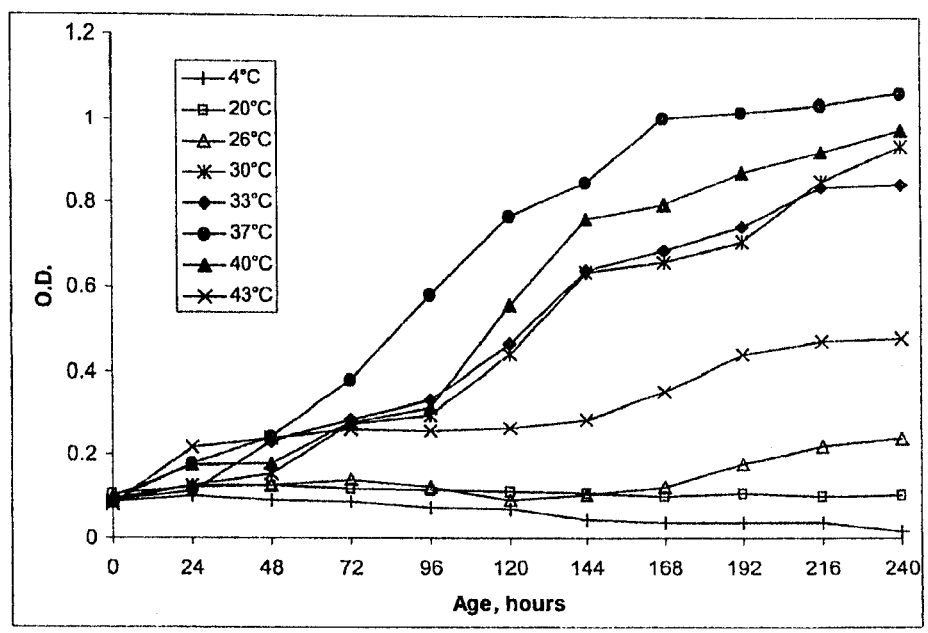
Figure 7A:
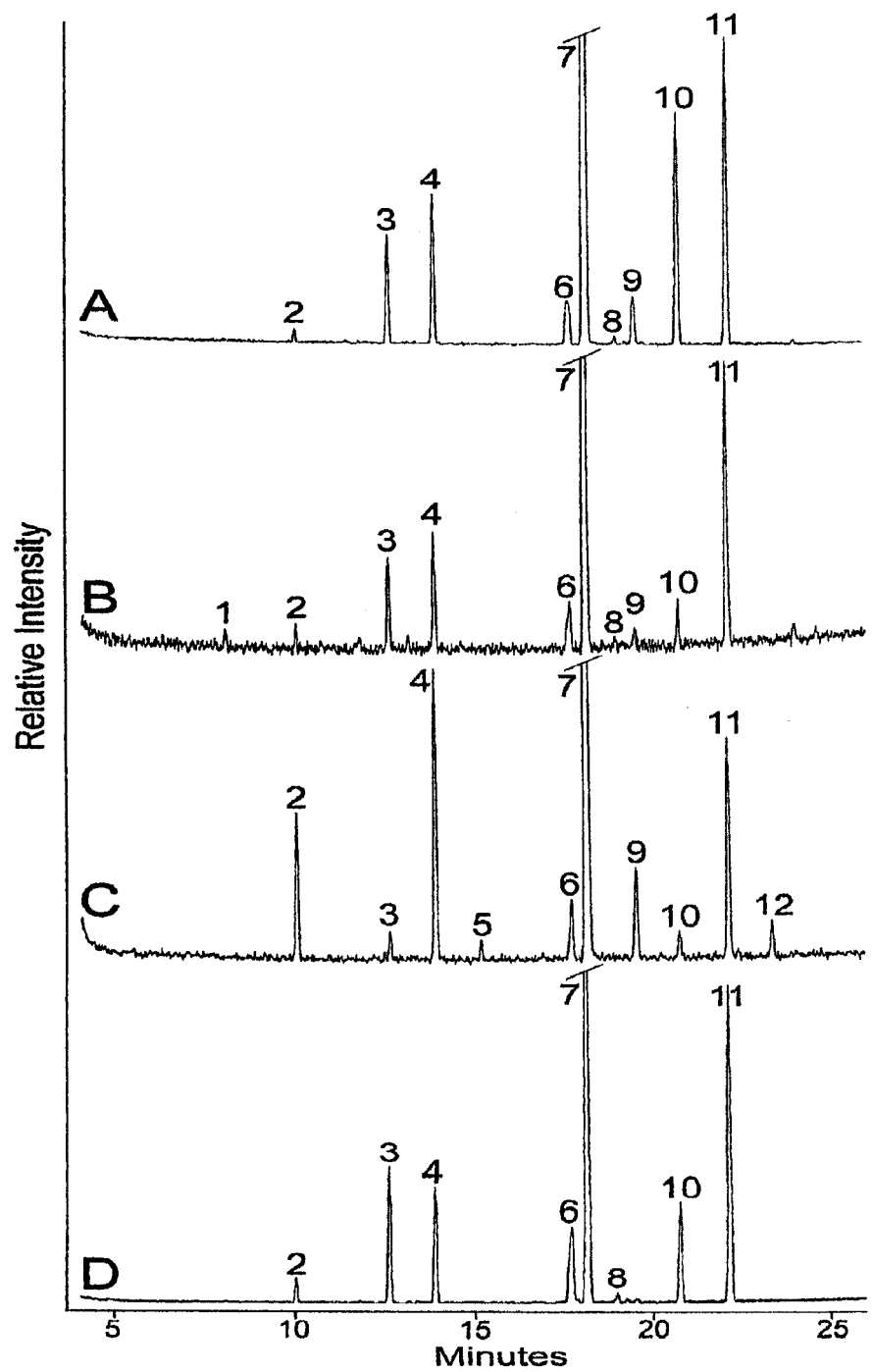
Figures 7B, 7C:
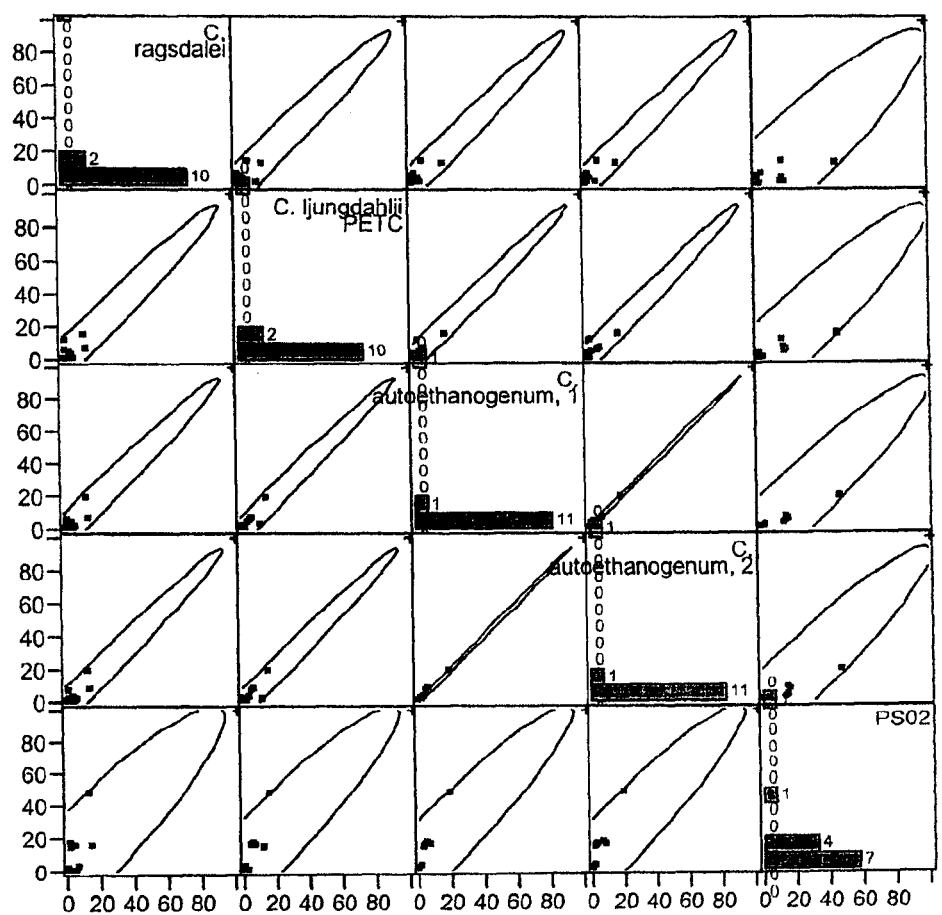
Figure 10:
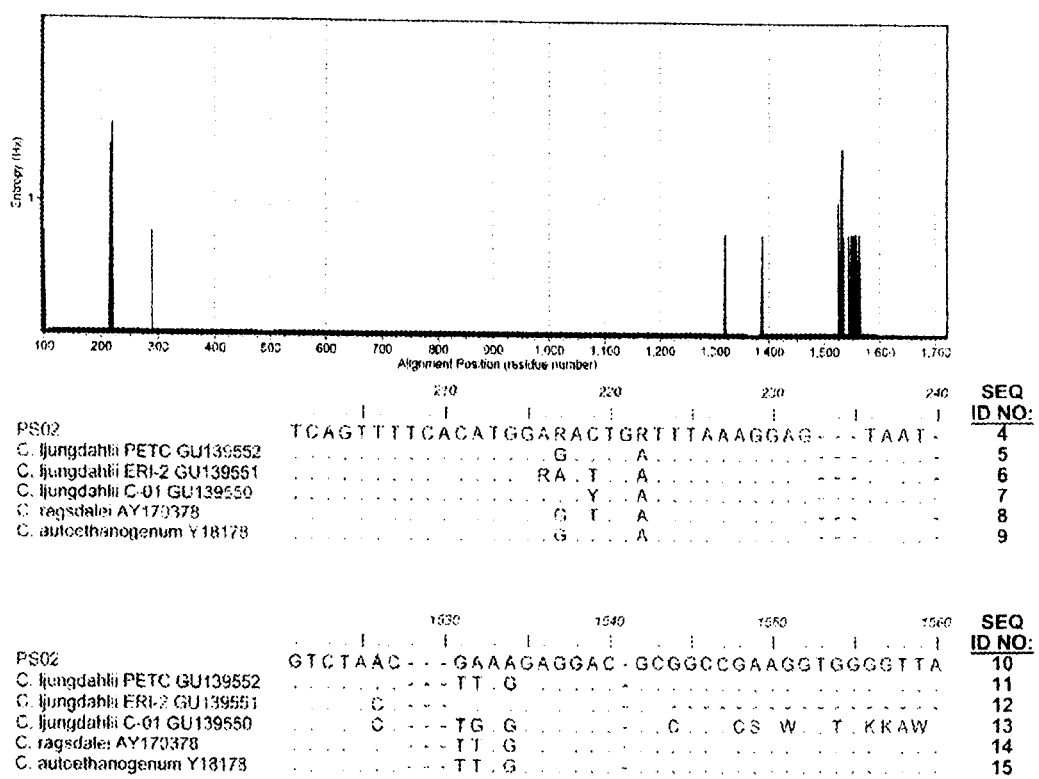
Figure 11:
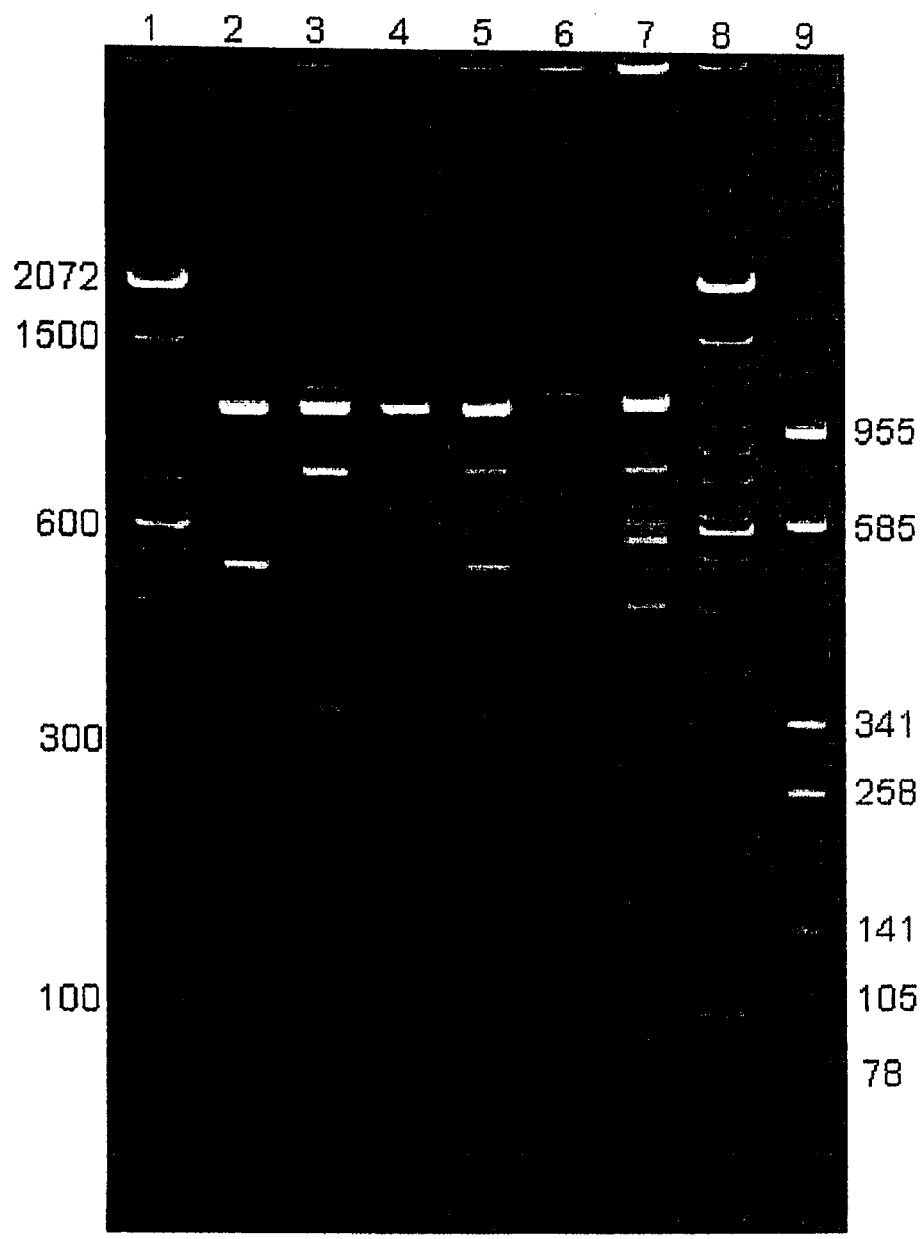
Figure 12:
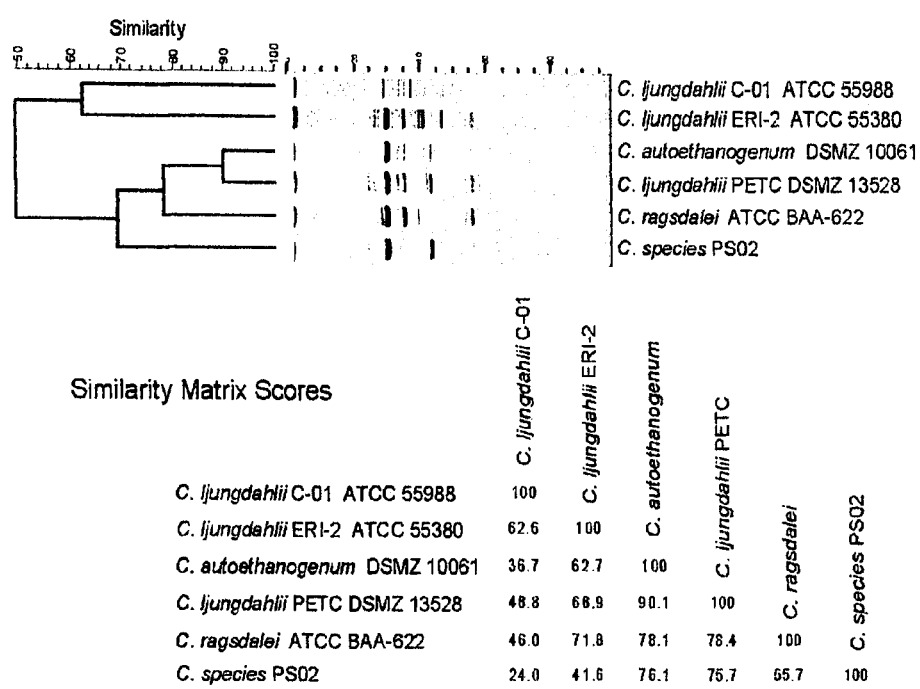
Figure 13:
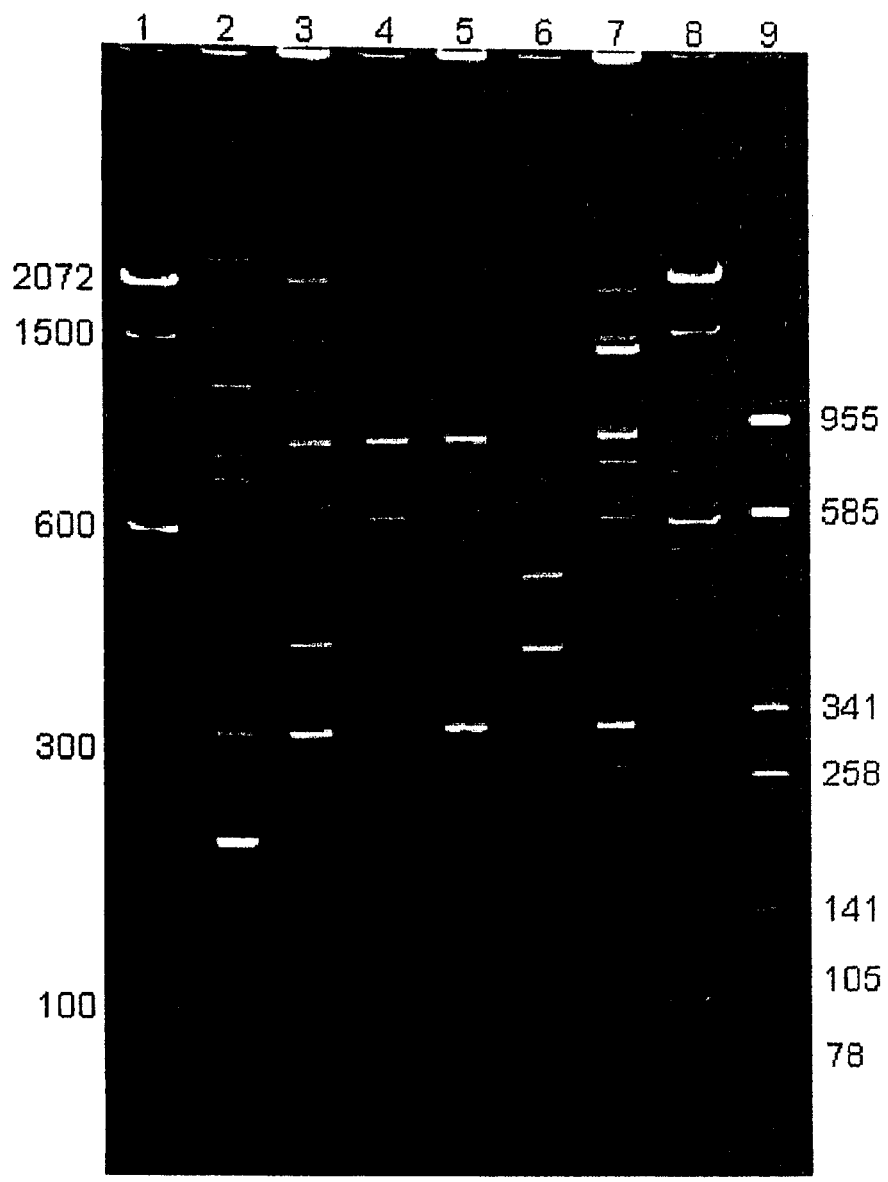
Figure 14:
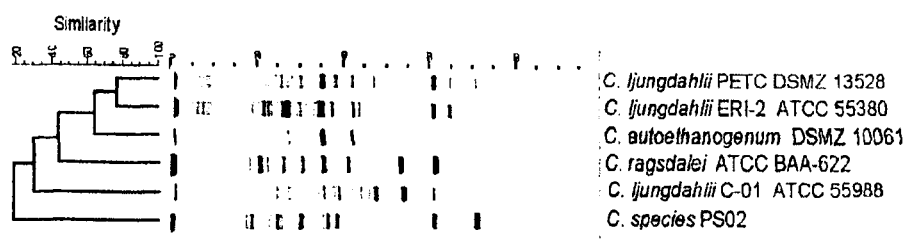
Figure 15:
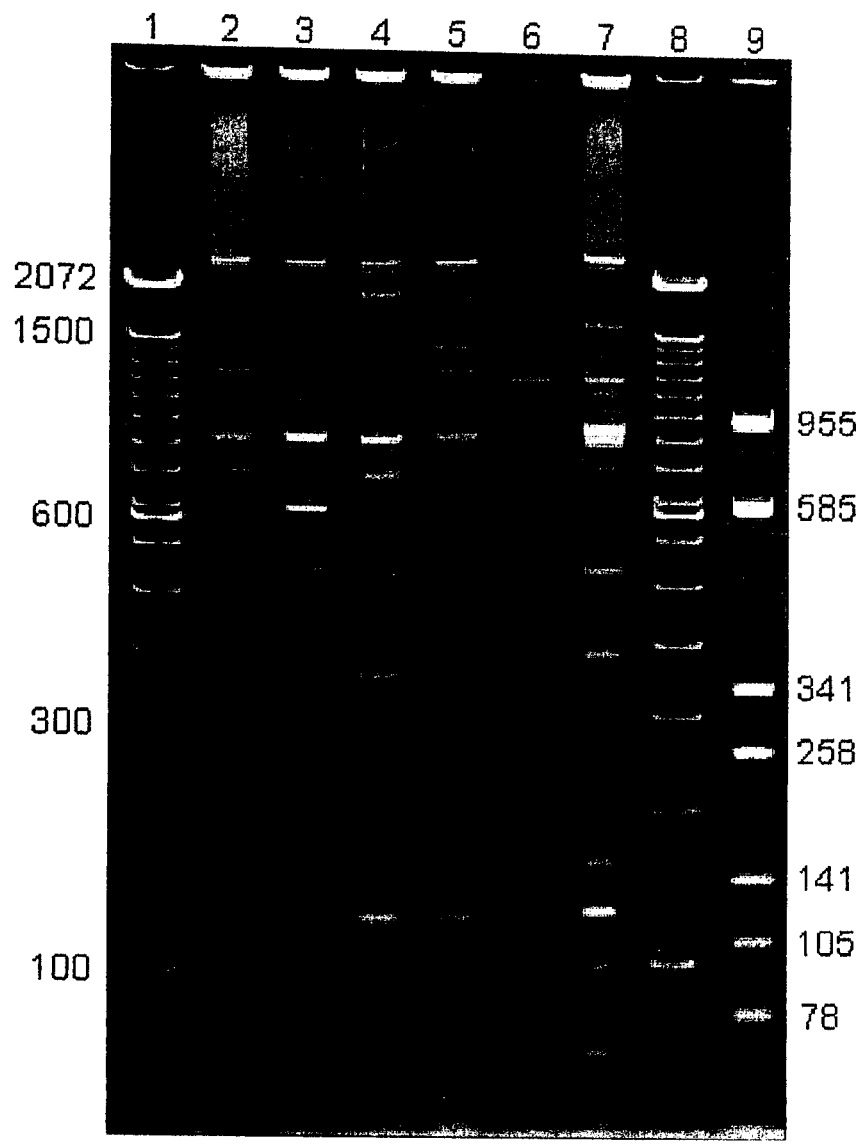
Figure 16:
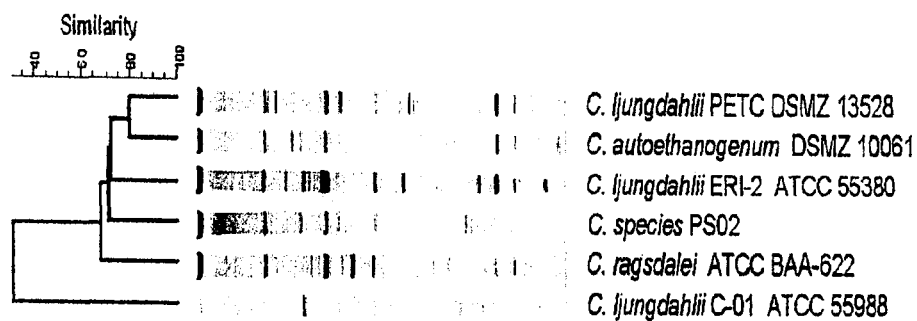
Figure 17:
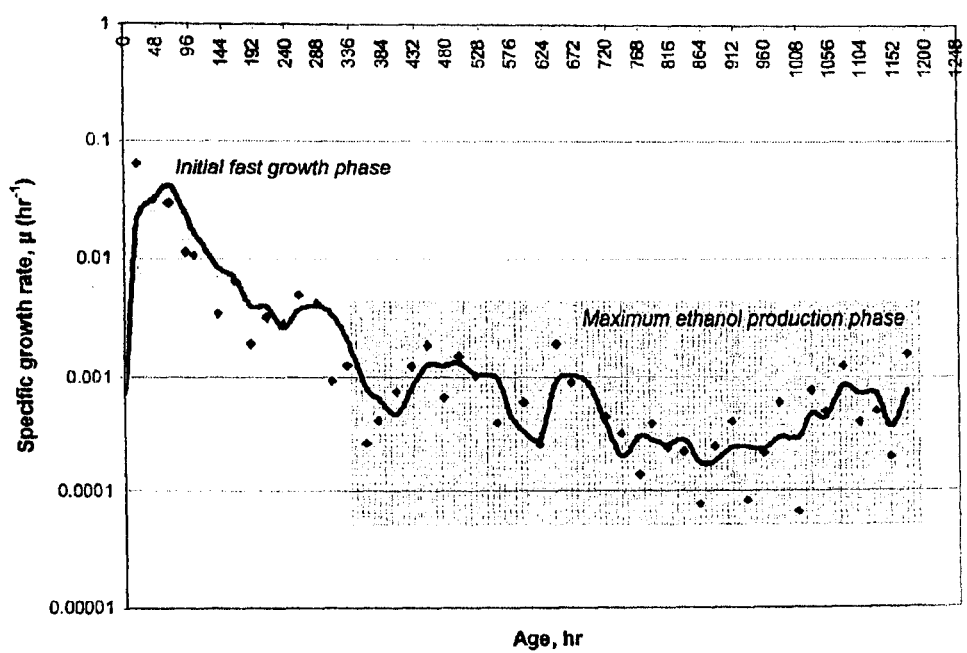
Figure 18:
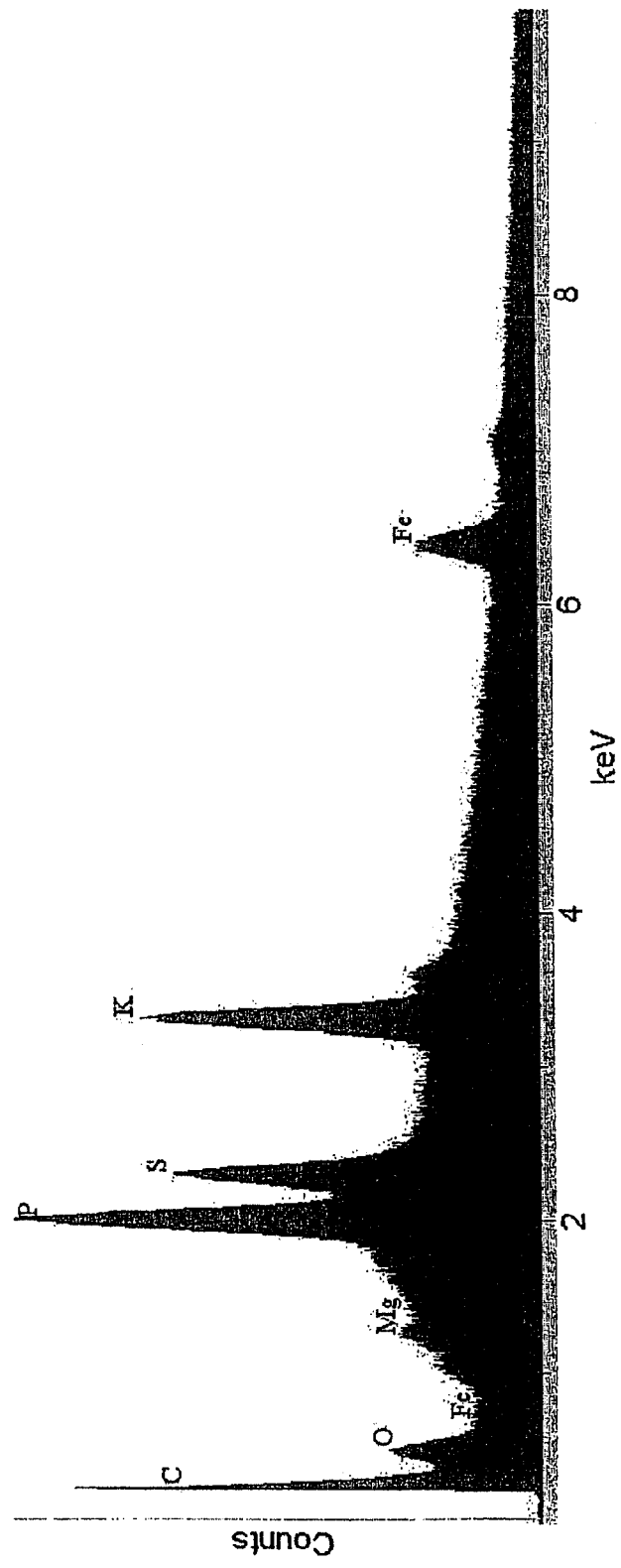
Figure 19:
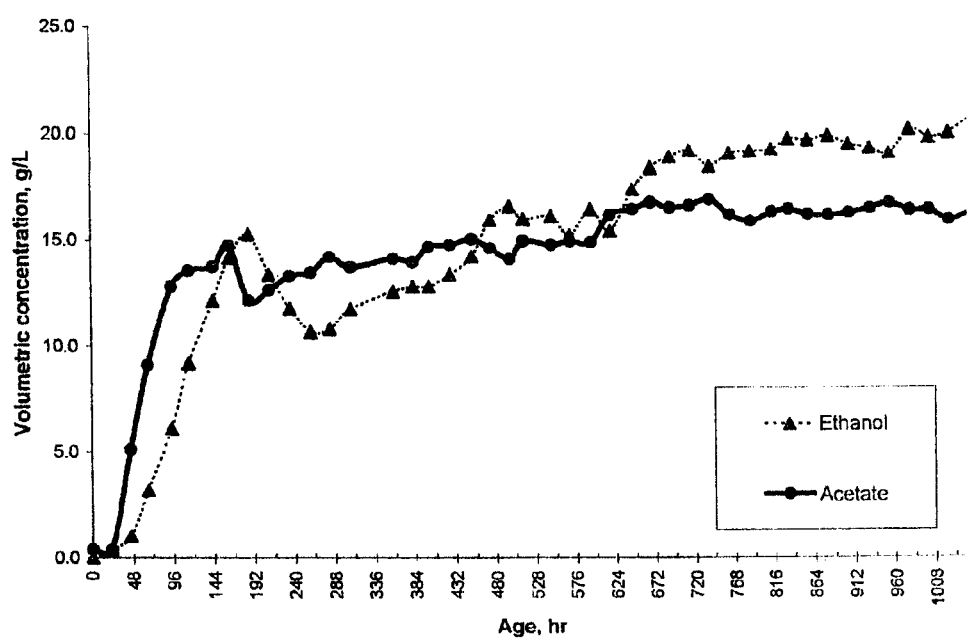
Figure 20:
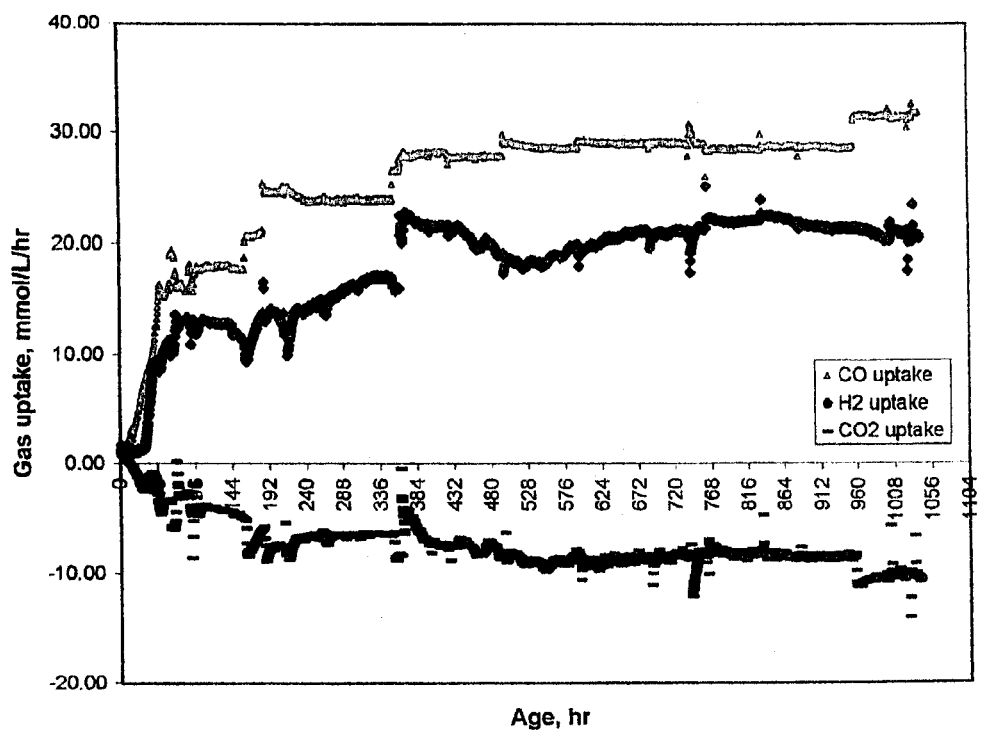
Figure 21:
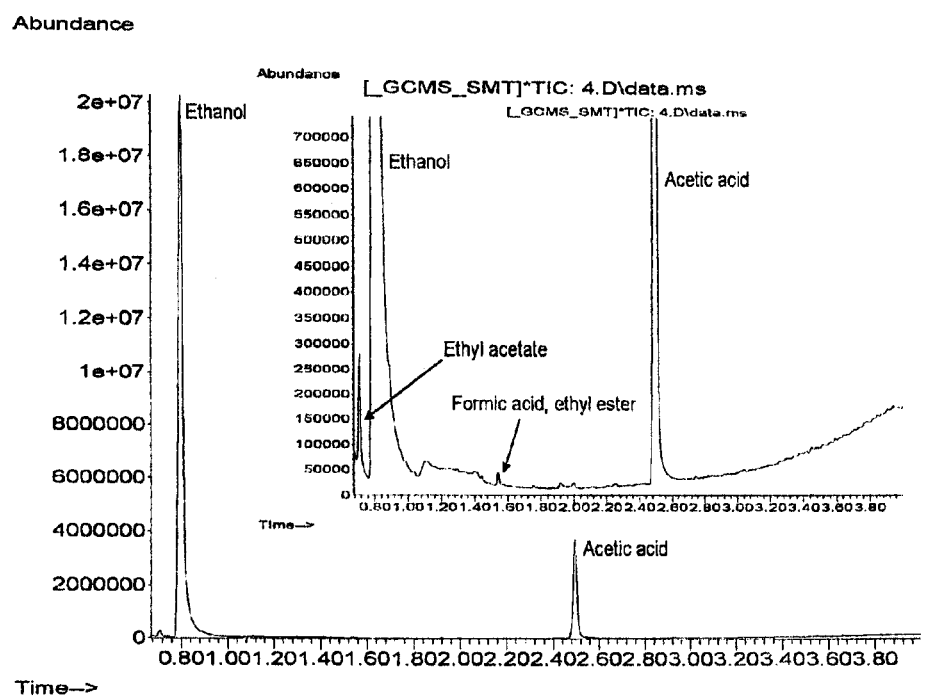
Figure 22A:
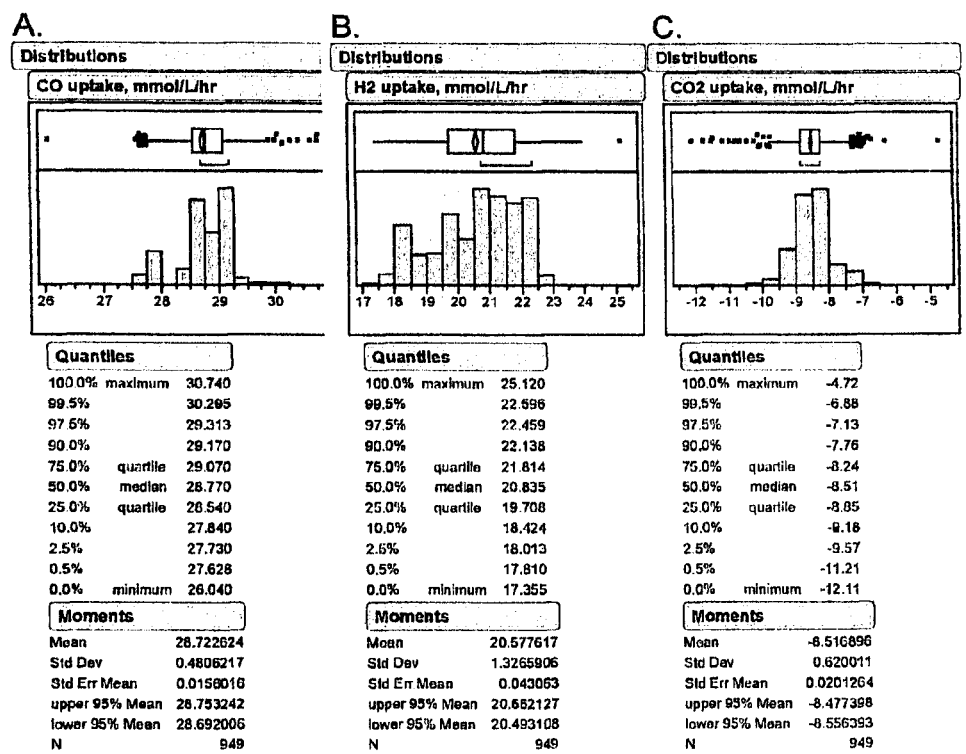
Figure 22B:
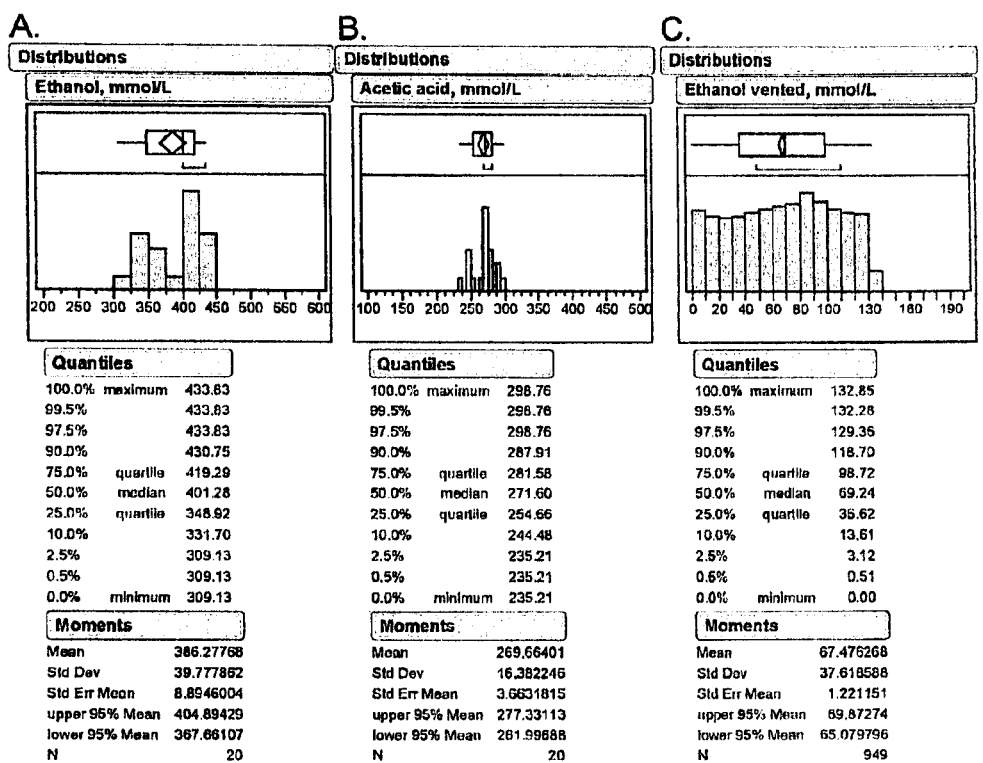
Figure 23:
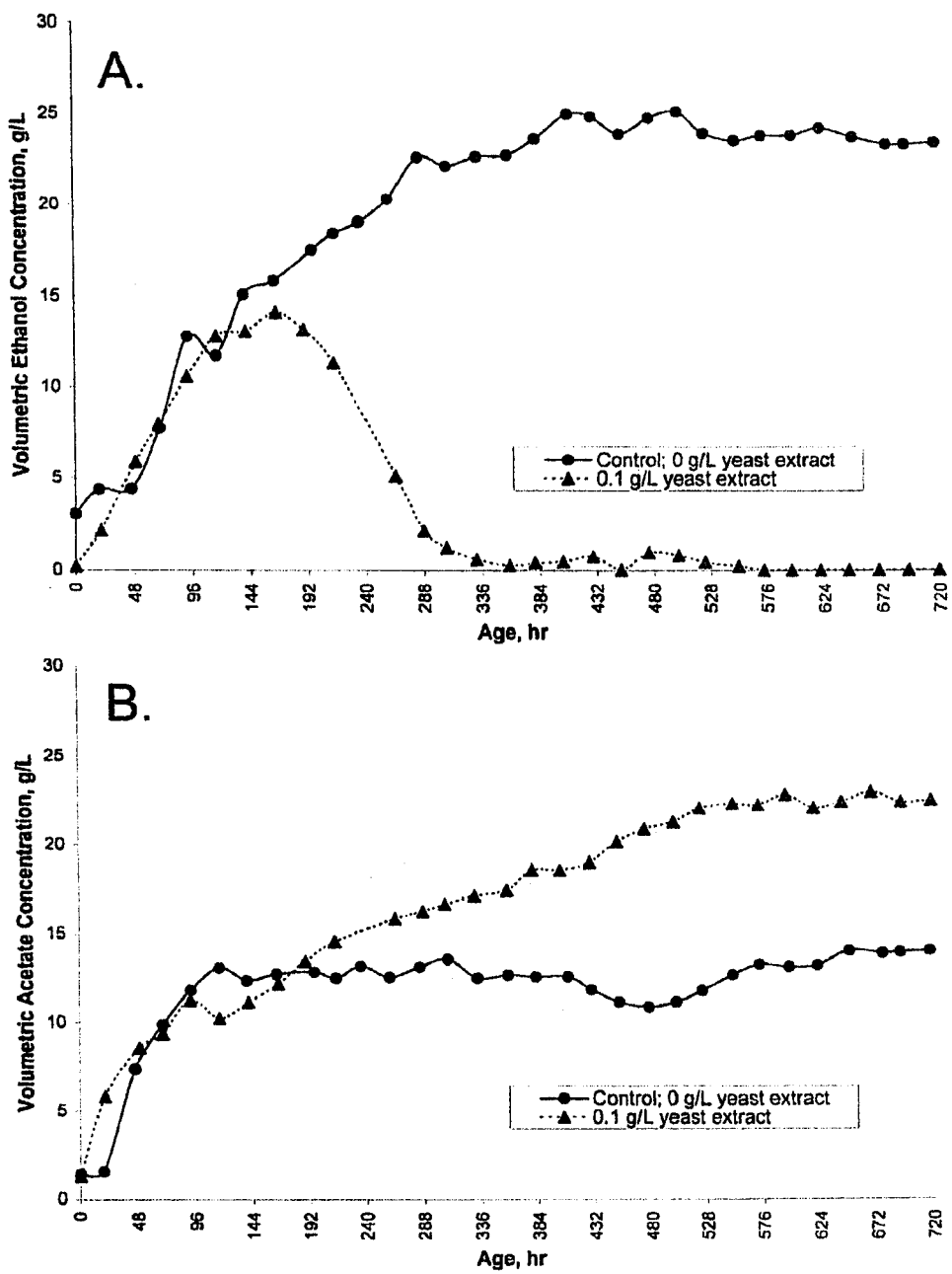

FIG. 23 illustrates the effect of organic carbon (yeast extract) addition on ethanol and acetate production by a synthesis gas-fed CSTR containing *Clostridium coskatii*. (A) Ethanol production in 2 L CSTR (D=0.5 day$^{-1}$) receiving a chemically-defined minimal media (Acetogen C5), or the same media supplemented with 0.1 g/L yeast extract. (B) Acetate production in 2 L CSTR (D=0.5 day$^{-1}$) receiving a chemically-defined minimal media, or the same media supplemented with 0.1 g/L yeast extract

DETAILED DESCRIPTION OF EMBODIMENTS

The bacterium of the present invention is a novel ethanologenic Clostridia species which displays the characteristics represented by ATCC No. PTA-10522, herein referred to as "*Clostridium coskatii* (PS02)". The phylogenetic, morphological, and biochemical properties of *Clostridium coskatii* (PS02) have been analyzed and are described in the Examples section below. While certain properties of *Clostridium coskatii* (PS02) are similar to other Clostridial species, *Clostridium coskatii* (PS02) possesses unique characteristics that confirm it is a novel species of this genus. The data included in the examples shows that this bacterium is a new representative of the *Clostridium* genus.

*Clostridium coskatii* (PS02) has the ability, under anaerobic conditions, to produce acetic acid and ethanol from the substrates, $CO+H_2O$, or $H_2+CO_2$, or $CO+H_2+CO_2$. The CO or $CO_2$ provide the carbon source and the $H_2$ or CO provide the electron source for the reactions producing acetic acid and ethanol. The primary product produced by the fermentation of CO and/or $H_2$ and $CO_2$ by *Clostridium coskatii* (PS02) is ethanol, according to the following reactions:

$$6CO + 3H_2O \rightarrow C_2H_5OH + 4CO_2 \quad (1)$$

$$6H_2 + 2CO_2 \rightarrow C_2H_5OH + 3H_2O \quad (2)$$

*Clostridium coskatii* (PS02) may also produce acetate. Acetate production occurs via the following reactions:

$$4CO + 2H_2O \rightarrow CH_3COOH + 2CO_2 \quad (3)$$

$$4H_2 + 2CO_2 \rightarrow CH_3COOH + 2H_2O \quad (4)$$

Many sources of CO, $CO_2$ and $H_2$ may be utilized by the *Clostridium* of the present invention. For example, preferred sources of these substrates include "waste" gases such as syngas, oil refinery waste gases, steel manufacturing waste gases, autothermal reforming of natural gas, and coal gasification. Sources also include gases (containing some $H_2$) which are produced by yeast, clostridial fermentations, and gasified cellulosic materials. Alternatively, such gaseous substrates are not necessarily produced as byproducts of other processes, but may be produced specifically for use in the fermentation reactions of the invention, which utilize *Clostridium coskatii* (PS02). Those of skill in the art will recognize that any source of substrate gas may be used in the practice of the present invention, so long as it is possible to provide the *Clostridium coskatii* with sufficient quantities of the substrate gases under conditions suitable for the bacterium to carry out the fermentation reactions.

In one preferred embodiment of the invention, the source of CO, $CO_2$ and $H_2$ is syngas. Syngas for use as a substrate may be obtained, for example, as a gaseous byproduct of coal gasification. Alternatively, syngas can be produced by gasification of readily available low-cost agricultural raw materials expressly for the purpose of bacterial fermentation, thereby providing a route for indirect fermentation of biomass to fuel alcohol. There are numerous examples of raw materials which can be converted to syngas, as most types of vegetation could be used for this purpose. Preferred raw materials include but are not limited to perennial grasses such as switchgrass, crop residues such as corn stover, processing wastes such as sawdust, etc. Those of skill in the art are familiar with the generation of syngas from such starting materials. In general, syngas is generated in a gasifier from dried biomass primarily by pyrolysis, partial oxidation, and steam reforming, the primary products being CO, $H_2$ and $CO_2$. The terms "gasification" and "pyrolysis" refer to similar processes; both processes limit the amount of oxygen to which the biomass is exposed. The term "gasification" is sometimes used to include both gasification and pyrolysis.

Combinations of sources for substrate gases fed into the indirect fermentation process may also be utilized to alter the concentration of components in the vent stream from the bioreactor. For example, the primary source of CO, $CO_2$ and $H_2$ may be syngas, which typically exhibits a concentration ratio of 37% CO, 35% $H_2$, and 18% $CO_2$, but the syngas may be supplemented with gas from other sources to enrich the level of CO (i.e., steel mill waste gas is enriched in CO) or $H_2$.

The *Clostridium coskatii* of the present invention must be cultured under anaerobic conditions. "Anaerobic conditions" means the level of oxygen ($O_2$) is below 0.5 parts per million in the gas phase.

The source of $H_2O$ for the reaction represented by Equations (1) or (3) is typically the aqueous media in which the organism is cultured.

In general, the optimized ethanol production media for culturing the acetogen of this invention is a liquid medium that is chemically-defined. However, those of skill in the art will recognize that alternative media can be utilized, for example, ATCC medium 1045 under a $H_2:CO_2$ or $CO:CO_2$ atmosphere at an initial pH of 6. Further, various media supplements may be added for any of several purposes, e.g. buffering agents, metals, vitamins, and salts. In particular, those of skill in the art are familiar with such techniques as nutrient manipulation and physiological adaptation, which result in increased or optimized yields of a bioproduct. For example, culturing solvent-producing microbes under "limited-growth" conditions (i.e. conditions which slow the rate of bacterial growth and reproduction) result in enhanced production of highly reduced fermentation products such as ethanol. This is likely because under limited-growth conditions, the ratio of available reducing equivalents (reduced ferridoxin, NADH, or NADPH) to available carbon increases, and the increased reducing power is diverted into chemical reduction of acetyl Co-A or organic acids to form alcohols. Examples of limited-growth conditions include, for example, maintaining the culture at non-optimal temperature or pH, and the limitation of nutrients and carbon sources. Generally, non-growth conditions would be implemented after a desired density of bacteria is reached in the culture. Those of skill in the art are familiar with procedures for optimizing the production of desired products, and all such optimized procedures using *Clostridium coskatii*(PS02) are intended to be encompassed by the present invention.

In particular, *Clostridium coskatii* (PS02) may be cultured using the Balch technique (Balch and Wolfe, 1976, Appl. Environ. Microbiol. 32:781-791; Balch et al., 1979, Microbiol. Rev. 43:260-296). This entails the aid of an anaerobic chamber for preparing culture materials and a gas exchange manifold to establish whatever gas phase is desired for culture in sealed tubes or vessels. More specific details on culturing solvent-producing acetogens, such as the use of an acidic pH, appear in Tanner et al., 1993, Int. J. Syst. Bacteriol. 43:232-236 and Liou et al., 2005, Int. J. Syst. Evol. Microbiol. 55:2085-2091. Methods to enhance ethanol production include optimization of key medium components (such as iron, phosphate and vitamins), control of culture pH, random mutagenesis of the bacterium followed by clonal screening, or genetic engineering of the bacterium.

The metabolism of gases (CO and/or $H_2$ and $CO_2$) supplied to the fermentation by *Clostridium coskatii* (PS02) can be carried out in any of several types of apparatuses that are known to those of skill in the art, with or without additional modifications, or in other styles of fermentation equipment that are currently under development. Examples include but are not limited to bubble column reactors, two stage bioreactors, trickle bed reactors, membrane reactors, packed bed reactors containing immobilized cells, etc. The chief requirements of such an apparatus include:

(1) Axenicity;
(2) Anaerobic conditions;
(3) Suitable conditions for maintenance of temperature, pressure, and pH;
(4) Sufficient quantities of substrates are supplied to the culture;
(5) The end products of the fermentation can be readily recovered from the bacterial broth.

The reactor may be, for example, a traditional stirred tank reactor, a column fermentor with immobilized or suspended cells, a continuous flow type reactor, a high pressure reactor, a suspended cell reactor with cell recycle, and other examples previously listed. Furthermore, reactors may be arranged in a series and/or parallel reactor system which contains any of the above-mentioned reactors. For example, multiple reactors can be useful for growing cells under one set of conditions and generating ethanol (or other products) with minimal growth under another set of conditions.

In general, fermentation will be allowed to proceed until a desired level of product such as ethanol is produced in the culture media. Typically, this level of ethanol is in the range of at least 15 grams/liter of culture medium to 50 grams/liter, with a level of at least 30 grams/liter being preferable. *Clostridium coskatii* (PS02) remains viable and will grow in ethanol concentrations of at least 60 grams/liter. Alternatively, production may be halted when a certain rate of production is achieved, e.g. when the rate of production of a desired product has declined due to, for example, build-up of bacterial waste products, reduction in substrate availability, feedback inhibition by products, reduction in the number of viable bacteria, or for any of several other reasons known to those of skill in the art. In addition, continuous culture techniques exist which allow the continual replenishment of fresh culture medium with concurrent removal of used medium, including any liquid products therein (i.e. the chemostat mode).

The products that are produced by the bacterium of this invention can be removed from the culture and purified by any of several methods that are known to those of skill in the art. For example, ethanol can be removed and further processed, e.g. by solvent extraction; distillation to the azeotrope followed by azeotropic distillation; molecular sieve dehydration; pervaporation; or flow-through zeolite tubes. Those of skill in the art will recognize that the two main techniques in industry for ethanol dehydration following distillation are azeotropic distillation and molecular sieve dehydration. In addition, depending on the number of products, several separation techniques may need to be employed to obtain several pure products. Likewise, acetate may be removed and further processed by similar processes.

*Clostridium coskatii* (PS02) was obtained from an anaerobic enrichment inoculated with estuary sediment collected from Coskata-Coatue Wildlife Refuge in Nantucket, Mass. by a procedure described previously (Bryant, 1972) in 125 mL serum vials under an atmosphere of $CO:H_2:N_2:CO_2$ (7:37:33:23 mole %) and an initial pH of 6.0, using Acetogen C3 medium, such as described below. A master cell bank was prepared from biomass acquired from single colony isolates picked from agar-containing (15% w:v) petri plates, using the Acetogen C3 medium and an atmosphere of $H_2$ (5%), $CO_2$ (10%), and $N_2$ (85%). This bacterium was deposited with the American Type Culture Collection as strain ATCC No. PTA-10522 on Dec. 10, 2009 under the terms of the Budapest Treaty.

Several phylogenetically diverse groups of anaerobic bacteria have the ability to convert CO, $CO_2$ and $H_2$ to a variety of commercially-important products including acetate, ethanol, butyrate, butanol, and hydrogen. A select subgroup, the ethanologenic Clostridia, exhibit the unique ability to simultaneously utilize hydrogen and carbon monoxide to form ethanol, along with small amounts of acetate while using carbon dioxide as a carbon source. The phylogenetic, morphological, and biochemical properties of *Clostridium coskatii* (PS02) have been analyzed and compared against other similar Clostridial species.

Other Clostridial species utilized in these comparison studies included: *Clostridium ljundahlii* PETC (ATCC No. 49587 or DSMZ No. 13528); *C. ragsdalei* (ATCC BAA-622); *C. autoethanogenum* (DSMZ No. 10061); *C. ljundgahlii* ERI-2 (ATCC No. 55380); and *C. ljungdahlii* C-01 (ATCC No. 55988). ATCC samples were obtained from the American Type Culture Collection (ATCC; Manassas, Va.). DSMZ samples were obtained from Deutsche Sammlung von Mikroorganismen and Zellkulturen (DSMZ) GmbH (Braunschweig, Germany). However, as of Feb. 1, 2010, *Clostridium ljungdahlii* O-52 is no longer publically available because the depositor has terminated supply activities with the American Type Culture Collection.

EXAMPLE 1

Cellular Morphology

Figure 1:
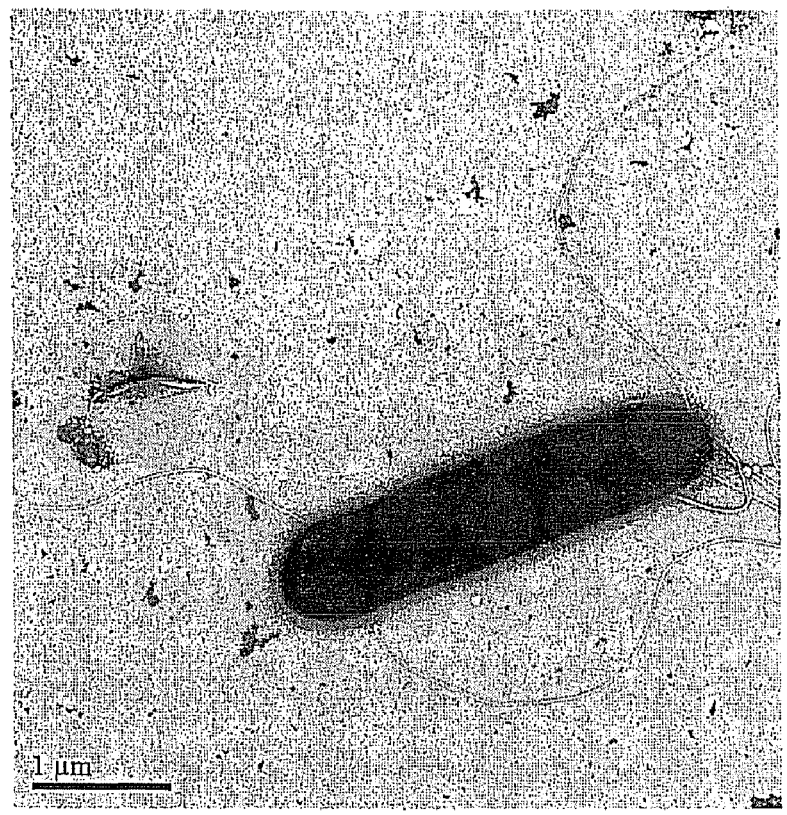
FIG. 1 is a transmission electron micrograph of a negative stained [phase, 25,000× magnification. Bar=1.0 μm.
Figure 2:
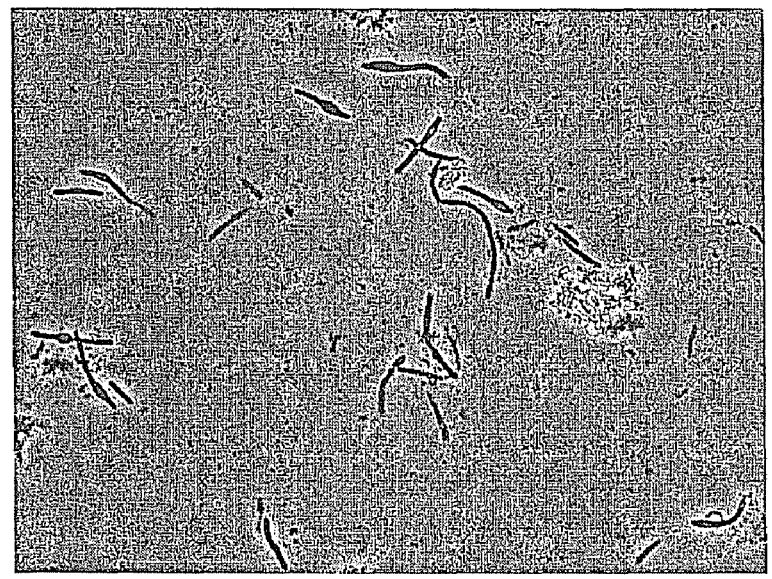
FIG. 2 is a phase-contrast light micrograph of *Clostridium coskatii* (PS02) cells during stationary phase, 1,000× magnification. Bar=14.63 μm.
Figure 3:
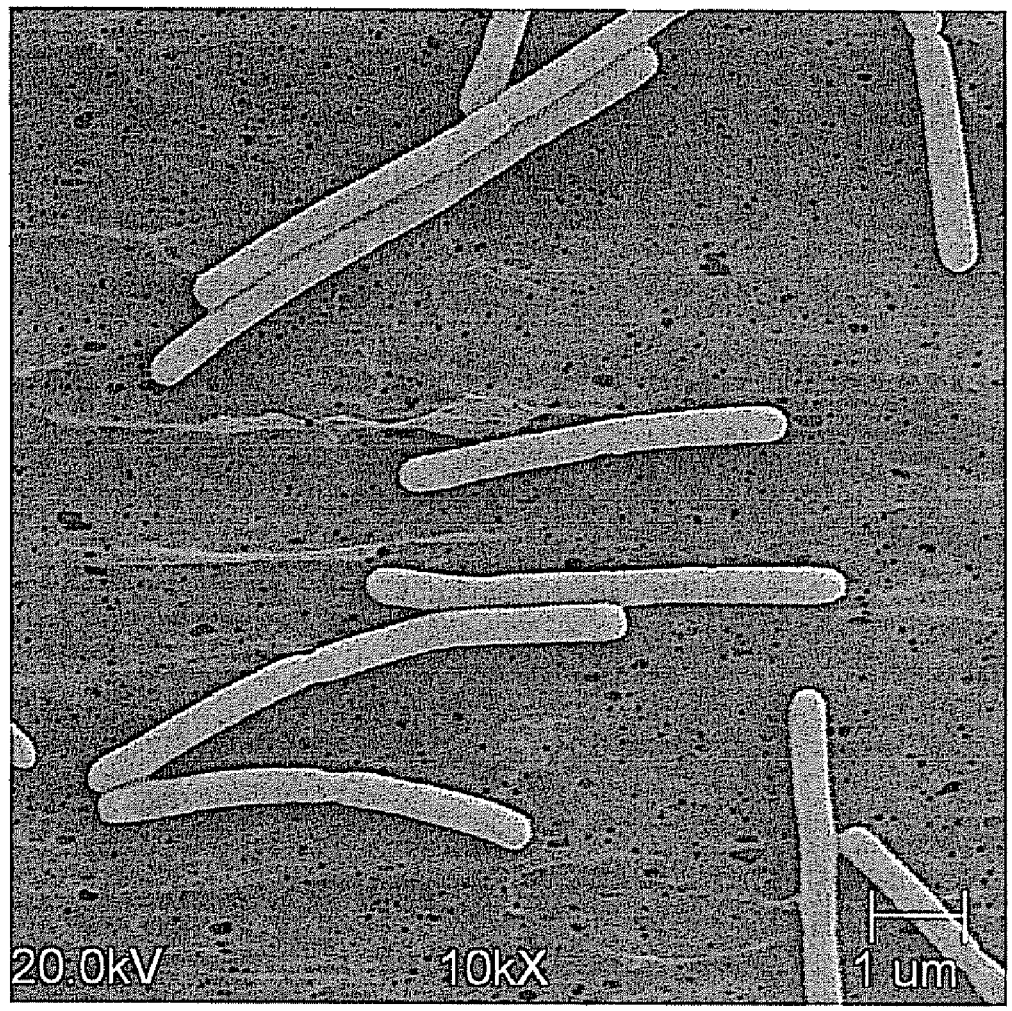
FIG. 3 is a scanning electron micrograph of *Clostridium coskatii* (PS02) cells harvested during late log phase growth, 10,000× magnification. Bar=1.0 μm.

Colonies of *Clostridium coskatii* (PS02) appeared circular, were white to translucent in color, and slightly raised at the center on Acetogen C3 agar plates. The color darkened to tan or light brown when the colony age exceed 6-7 days. Cells of *Clostridium coskatii* (PS02) were rarely motile, rod-shaped, stained gram-positive, and occurred singly or in chains. An outer cellular structure consistent with a 40 to 45 nm cell wall was seen in electron micrographs of thin sections of *C. coskatii* cells, which supports the gram-positive assignment. In early exponential growth, cells were 0.75 μm by 3-4 μm and were peritrichously flagellated (FIG. 1). Spores occurred infrequently, but when present appeared as mid-terminal to terminal swelling, and were most often club-like in appearance (FIG. 2). This property of spore morphology was similar to *Moorella thermoacetica* (Drake et al., 2006), but significantly different than the non-swelling spore morphology observed for *Clostridium autoethanogenum* (Abrini et al., 1994) or *Clostridium ragsdalei* (Huhnke et al., 2008). Comparison of electron micrographs for cells in early and late exponential growth showed that cells increased in their length during later phases of growth (FIG. 3). Elongation of the cells up to 20-30 μm was observed for aged batch cultures exhibiting high volumetric ethanol concentrations, and appeared to be related to physiological stress, since these cells were not easily recovered when transferred to a fresh medium. Sporulation was not observed in elongated cells, which likely contributed to the inability to recover these cells.

Acetogen C3 medium was used to initiate preserved cultures taken from a lyophilized or frozen master cell bank (1 mL equivalent volume). Cultures used in this example were grown at a temperature of 37° C. on an orbital shaker at 100 rpm (5 cm shaking amplitude). The culture medium was prepared using the strict anaerobic technique described by Balch and Wolfe (1976), as detailed in Tables A, B, D, and E below. After sterilization, an anaerobic vitamin solution (Table C) was aseptically added to the bottles, and the headspace of each bottle was exchanged with a gas mixture consisting of $CO:H_2:N_2:CO_2$ (7:37:33:23 mole %), using a final pressure of 104 kPa (15 psig). Standard inoculum size was 10% (v/v), which was transferred from a stock culture that was growing in mid to late exponential phase.

The pH of batch fermentations was controlled using 2-(N-morpholino)ethanesulfonic acid (MES; $pK_a$=5.97 at 37° C.) at a concentration of 20 g/L (pH 6.0). As a replacement to MES, the following buffers were used at a concentration of 20 g/L to conduct pH growth optimum studies: MES (pH 4-6.5), piperazine-N,N'-bis(2-ethanesulfonic acid (PIPES; pH 6.6 to 7.5; $pK_a$=6.66 at 37° C.), and Tris(hydroxymethyl)aminomethane (TRIS; pH 7.5 to 8.5; $pK_a$=7.72 at 37° C.).

TABLE A

Mineral stock solution

| Item | Component | Amount, g/L |
|---|---|---|
| 1 | NaCl | 80 |
| 2 | $NH_4Cl$ | 100 |
| 3 | KCl | 10 |
| 4 | $KH_2PO_4$ | 10 |
| 5 | $MgSO_4 \cdot 7H_2O$ | 20 |
| 6 | $CaCl_2 \cdot 2H_2O$ | 4 |

TABLE B

Trace metals stock solution.

| Item | Component | Amount, g/L |
|---|---|---|
| 1 | Hydrochloric acid, 12.1N | 2.360 |
| 2 | $MnSO_4 \cdot H_2O$ | 1.0 |
| 3 | $FeSO_4 \cdot 7H_2O$ | 2.2 |
| 4 | $CoCl_2 \cdot 6H_2O$ | 0.2 |
| 5 | $ZnSO_4 \cdot 7H_2O$ | 1.0 |
| 6 | $NiCl_2 \cdot 6H_2O$ | 0.2 |
| 7 | $Na_2MoO_4 \cdot 2H_2O$ | 0.02 |
| 8 | $Na_2SeO_4$ | 0.1 |
| 9 | $Na_2WO_4$ | 0.2 |

TABLE C

Vitamin stock solution.

| Item | Component | Amount, mg/L |
|---|---|---|
| 1 | Pyridoxine, HCl | 10 |
| 2 | Thiamine, HCl | 5 |
| 3 | Calcium pantothenate | 5 |
| 4 | Nicotinic acid | 5 |
| 5 | Biotin | 2 |

TABLE D

Reducing agent stock solution.

| Item | Component | Amount, g/L |
|---|---|---|
| 1 | Cysteine (free base) | 40 |
| 2 | $Na_2S \cdot 2H_2O$ | 40 |

TABLE E

Final formulation of Acetogen C3 medium.

| Item | Component | Amount |
|---|---|---|
| 1 | Minerals stock solution | 25 mL/L |
| 2 | Trace metals solution | 10 mL/L |
| 3 | Vitamin stock solution | 20 mL/L |
| 4 | Yeast extract | 0.5 g/L |
| 5 | 2-(N-morpholino)ethanesulfonic acid | 20 g/L |
| 6 | 5N KOH | Adjust pH to 6.0 |
| 7 | Reducing agent | 2.5 mL/L |
| 8 | 0.1% aqueous resazurin | 1 mL/L |

Exponential-phase cells grown on Acetogen C3 medium or late-exponential-phase cells growth in CSTRs on Acetogen C5 medium were used for scanning and transmission electron microscopy. Acetogen C5 medium was essentially the same as Acetogen C3 medium, except that sodium sulfide, yeast extract, and the MES buffer were omitted, and an antifoam, such as Antifoam A (Sigma Chemical, St. Louis, Mo.) was added to the medium at a final concentration of 20 mg/L. The samples were examined using a Hitachi S-570 scanning electron microscope, equipped with a Delta 4 Quantum thin-window X-ray detector for simultaneous image and elemental analysis of bacterial cells. For transmission electron microscopy, cells (approximately $1 \times 10^{20}$) were fixed in solution with 4% glutaraldehyde in PBS, spread onto carbon coated Formvar grids, and stained with 0.5% phosphotungsgate (pH 7.0). Cells were examined and photographed using a JEOL 1200 EX FX transmission electron microscope. Light microscopy was performed wet mount preparations of fermentation broth using a Nikon Eclipse 50i photomicroscope equipped with Nikon NIS-Elements image acquisition software (Nikon Instruments, Melville, N.Y.).

EXAMPLE 2

Physiology

*Clostridium coskatii* (PS02) was strictly anaerobic. Chemolithoautotrophic growth in the absence of yeast extract, occurred with $H_2+CO_2$ or CO. Chemoorganotrophic growth was observed with the following substrates: Pyruvate, succinate, citrate, malate, xylose, mannose, fructose, glucose, salacin, arginine, glutamate, histidie, glutamine, serine, alanine, alpha-ketoglutarate, oxaloacetate, phosphoenol pyruvate, shikimic acid, iso-citrate, sucrose, and malonic acid. Table F shows a substrate matrix comparison between *Clostridium coskatii* (PS02).

Six organic substrates differentiated *C. coskatii* from three ethanologenic Clostridia: *C. ljungdahlii* PETC, *C. ragsgalei*, and *C. ljungdahlii*. These differentiating substrates included D-gluconic acid, citrate, maleic acid, rhamnose, arginine, and oxaloacetic acid (Table F). These differences indicate differences in the metabolic regulation or catabolic genes required for metabolism of these substrates among these four bacteria.

(1) *Clostridium coskatii* (PS02) and *C. autoethanogenum* could be distinguished by the inability of *C. coskatii* to grow on D-gluconic acid and rhamnose, and also the inability of *C. autoethanogenum* to grow on citrate.
(2) *Clostridium coskatii* (PS02) and *C. ragsdalei* could be distinguished by the inability of *C. ragsdalei* to grow on citrate, maleic acid, histidine, oxaloacetic acid, and arginine.
(3) *Clostridium coskatii* (PS02) and *C. ljungdahlii* PETC could be distinguished by the inability of *C. coskatii* to grow on D-gluconic acid, and rhamnose, and also the inability of *C. ljungdahlii* PETC to grow on citrate.

TABLE F

Growth on various substrates of Clostridial species

| Substrate | *C. autoethangenum* | *C. ragsdalei* | *C. ljungdahlii* PETC | *C. coskatii* PS02 |
|---|---|---|---|---|
| CO | + | + | + | + |
| $H_2 + CO_2$ | + | + | + | + |
| D-Gluconic Acid | + | − | + | − |
| Na-Formate | − | − | − | − |
| Na-Acetate | − | − | − | − |
| Na-Lactate | − | − | − | − |
| Na-Pyruvate | + | + | + | + |
| Na-Propianate | − | − | − | − |
| Na-Succinate | + | + | + | + |
| Na-Citrate | − | − | − | + |
| Malic acid | + | + | + | + |
| Na-Fumerate | − | − | − | − |
| Maleic acid | + | − | + | + |
| Lactose | − | − | − | − |
| Arabinose | − | − | − | − |
| Xylose | + | + | + | + |
| Mannose | + | + | + | + |
| Fructose | + | + | + | + |
| Glucose | + | + | + | + |
| Methanol | − | − | − | − |
| Ethanol | + | + | + | + |
| Iso-Propanol | − | − | − | − |
| 1-Propanol | − | − | − | − |
| Butanol | − | − | − | − |
| Rhamnose | + | − | + | − |
| Sorbitol | − | − | − | − |
| Cellibiose | − | − | − | − |
| Salicin | + | + | + | + |
| Starch | − | − | − | − |
| Arginine | + | − | + | + |
| Glutamate | + | + | + | + |
| Histidine | + | − | + | + |
| Glutamine | + | + | + | + |
| Serine | + | + | + | + |
| Alanine | + | + | + | + |
| D-Ribose | − | − | − | − |
| Alpha-ketoglutarate | + | + | + | + |
| Oxaloacetic acid | + | − | − | + |
| Phosphoenol-pyruvate | + | + | + | + |
| Shikimic acid | + | + | + | + |
| Glycerol | − | − | − | − |
| Iso-Citrate | + | + | + | + |
| Sucrose | + | + | + | + |
| Galactose | − | − | − | − |
| Malonic acid | + | + | + | + |
| D-Maltose | − | − | − | − |

Growth was measured spectrophotometrically at 600 nm (Spectronic 20D; Milton Roy). Carbon substrate utilization was based upon growth after consecutive transfers in media containing 1 g/L of each carbon source. For carbon substrates, screening was performed under an atmosphere of $N_2$: $CO_2$ (80%:20%). A positive growth response was recorded for an OD600 exceeding 0.2 AU. For citrate, additional $^{13}$C-labeled isotope experiments were conducted to determine the nature of products by analysis of final 0.2 μm-filtered product samples by carbon NMR using a Bruker UltraShield Avance 400 MHz nuclear magnetic resonance spectrometer.

EXAMPLE 3

Antibiotic Susceptibility

The antibiotic susceptibility of *Clostridium coskatii* (PS02) was evaluated in Acetogen C3 media against 17 antibiotics at a concentration of 100 µg/mL (Table G). *Clostridium coskatii* (PS02) was resistant to erythromycin, nalidixic acid, spectinomycin, colistin, penicillin, streptomycin, and chloramphenicol. Three antibiotics differentiated *C. coskatii* from three ethanologenic Clostridia: *C. ljungdahlii* PETC, *C. ragsgalei*, and *C. autoethanogenum*. These differentiating antibiotics included, erythromycin, carbenicillin, and chloramphenicol (Table J). Resistance to erythromycin and carbenicillin was shared by *Clostridium coskatii* (PS02) and *Clostridium ljungdahlii* PETC; however, resistance to chloramphenicol was trait demonstrated only by *Clostridium coskatii* (PS02).

TABLE G

Antibiotic susceptibility patterns for various clostridial species using an antibiotic concentration of 100 µg/ml (+ indicates growth).

| Antibiotic | *C. autoethangenum* | *C. ragsdalei* | *C. ljungdahlii* PETC | *C. coskatii* PS02 |
|---|---|---|---|---|
| Ampicillin | − | − | − | − |
| Erythromycin | − | − | + | + |
| Nalidixic acid | + | + | + | + |
| Spectinomycin | + | + | + | + |
| Vancomycin | − | − | − | − |
| Colistin | + | + | + | + |
| Carbenicillin | − | − | + | + |
| Gentamicin | − | − | − | − |
| Penicillin | + | + | + | + |
| Streptomycin | + | + | + | + |
| Chloramphenicol | − | − | − | + |
| Kanamycin | − | − | − | − |
| Paromomycin | − | − | − | − |
| Tetracylcine | − | − | − | − |
| Lincomycin | − | − | − | − |
| Rifampicin | − | − | − | − |
| Tylosin | − | − | − | − |

Antibiotic susceptibility was based upon growth in media containing 100 µg/mL of each antibiotic. The atmosphere was 37% CO, 35% $H_2$, 22% $CO_2$ with a balance gas of $N_2$. A positive growth response was recorded for an OD600 exceeding 0.2 AU.

EXAMPLE 4

PH and Temperature Optima

Figure 4:
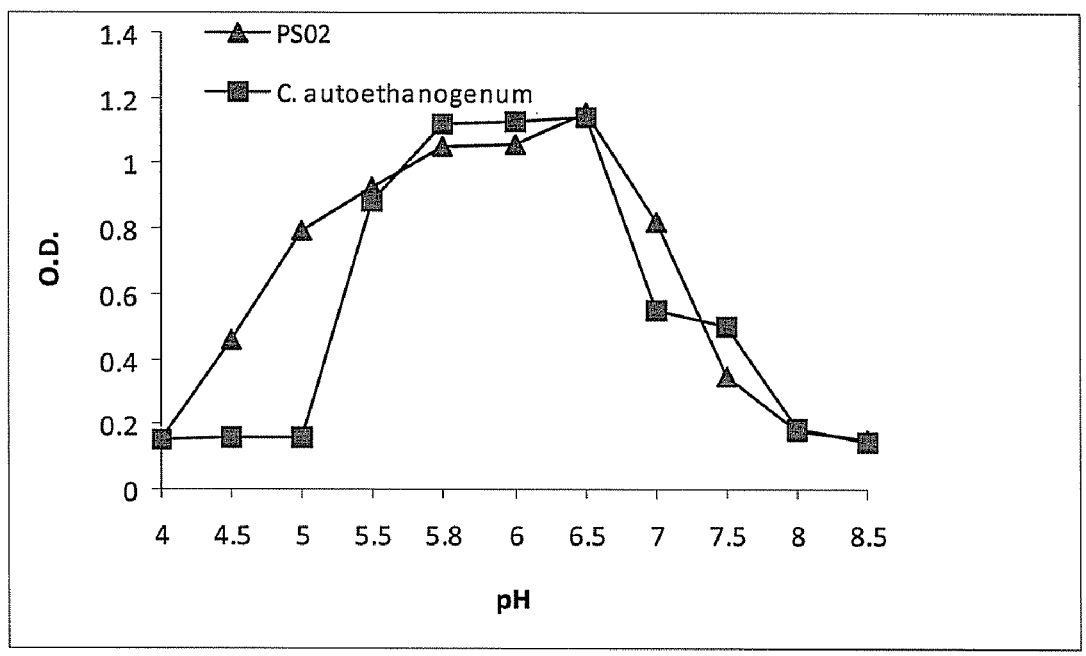
FIG. 4 illustrates the pH growth optimum based on optical density for a batch culture of *Clostridium coskatii* (PS02) compared to *Clostridium autoethanogenum*.

*Clostridium coskatii* (PS02) grew optimally at an initial pH between 5.8 and 6.5; growth occurred at initial pH values between 4.0 and 8.0 (FIG. 13a). When cultured in unbuffered media with an initial pH of 6.0, a final pH of 4.5 was measured. Cell growth was significantly inhibited by undissociated acetic acid when the concentration exceeded 50 mM. *Clostridium coskatii* showed better growth characteristics between pH 4.5 and 5.5 when compared to *Clostridium autoethanogenum* (FIG. 4); this trait might be particularly useful for an industrial process.

Figure 5:
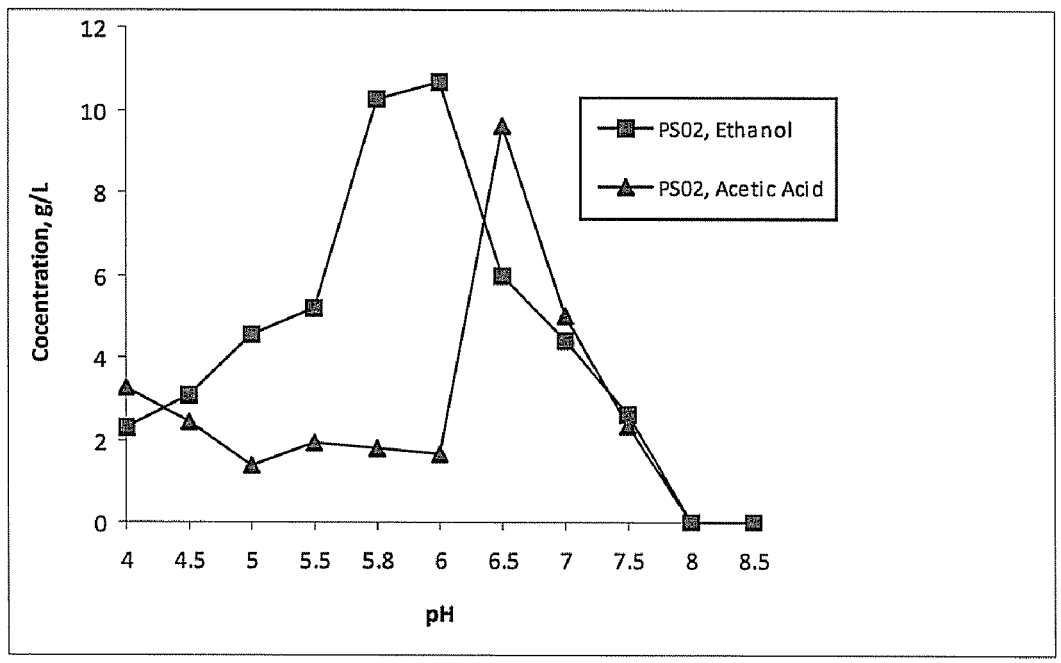
FIG. 5 illustrates the pH growth optimum for a batch culture of *Clostridium coskatii* (PS02) based on volumetric concentration of the end products, ethanol and acetate.

In addition to the collection of cell density measurements at various pH points, final fermentation products (acetate and ethanol) were also measured for batch fermentations using buffered fermentation media in a pH range from 4.0 to 8.5. Optimal pH conditions for production of acetate were at a pH of 5.85, at which a volumetric concentration of 11.0 g/L of acetate was produced in 120 hours. The optimum of ethanol production was in a pH range from 6.0 to 6.5, at which a volumetric concentration of 9.9 g/L of ethanol was produced in 120 hours (FIG. 5).

Figure 6:
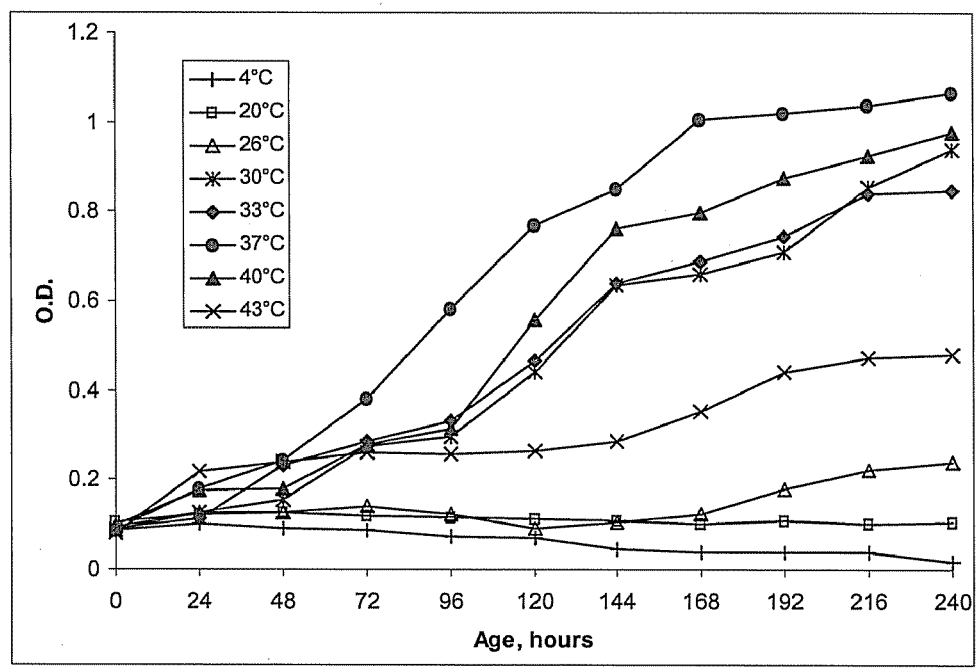
FIG. 6 illustrates the temperature growth optimum of *Clostridium coskatii* (PS2) based on optical density.

The optimal temperature for growth of *Clostridium coskatii* was 37° C. and the temperature range in which *Clostridium coskatii* (PS02) grew was 26-43° C. (FIG. 6).

Fermentation broth was analyzed for ammonia, orthophosphate, sodium, potassium, lactate, and osmolality using a Nova Bioprofile 300A biochemistry analyzer (Waltham, Mass.). Organic acid and alcohol analysis was conducted using an Agilent 1200 liquid chromatograph equipped with a Hi-Plex H analytical HPLC column (300×7.7 mm; PL1170-6830; Polymer Labs, Palo Alto, Calif.) equilibrated in aqueous 5 mM $H_2SO_4$ at a flow rate of 1 mL/min. Identification and confirmation of organic acids and alcohols in the broth fraction were performed on an Agilent 6890N gas chromatograph (GC) equipped with a 5975B electron-impact mass spectrometer (MS) and DB FFAP capillary column (15 m×250 µm×0.25 µm film, #122-3212, Agilent Technologies, Santa Clara, Calif.). Gas chromatography conditions were: Inlet=230° C.; oven programming=35-180° C. at 37°/min., MS interface=240° C., helium flow=1.7 mL/min.

EXAMPLE 5

Fatty Acid Methyl Ester Analysis

Figure 7A:
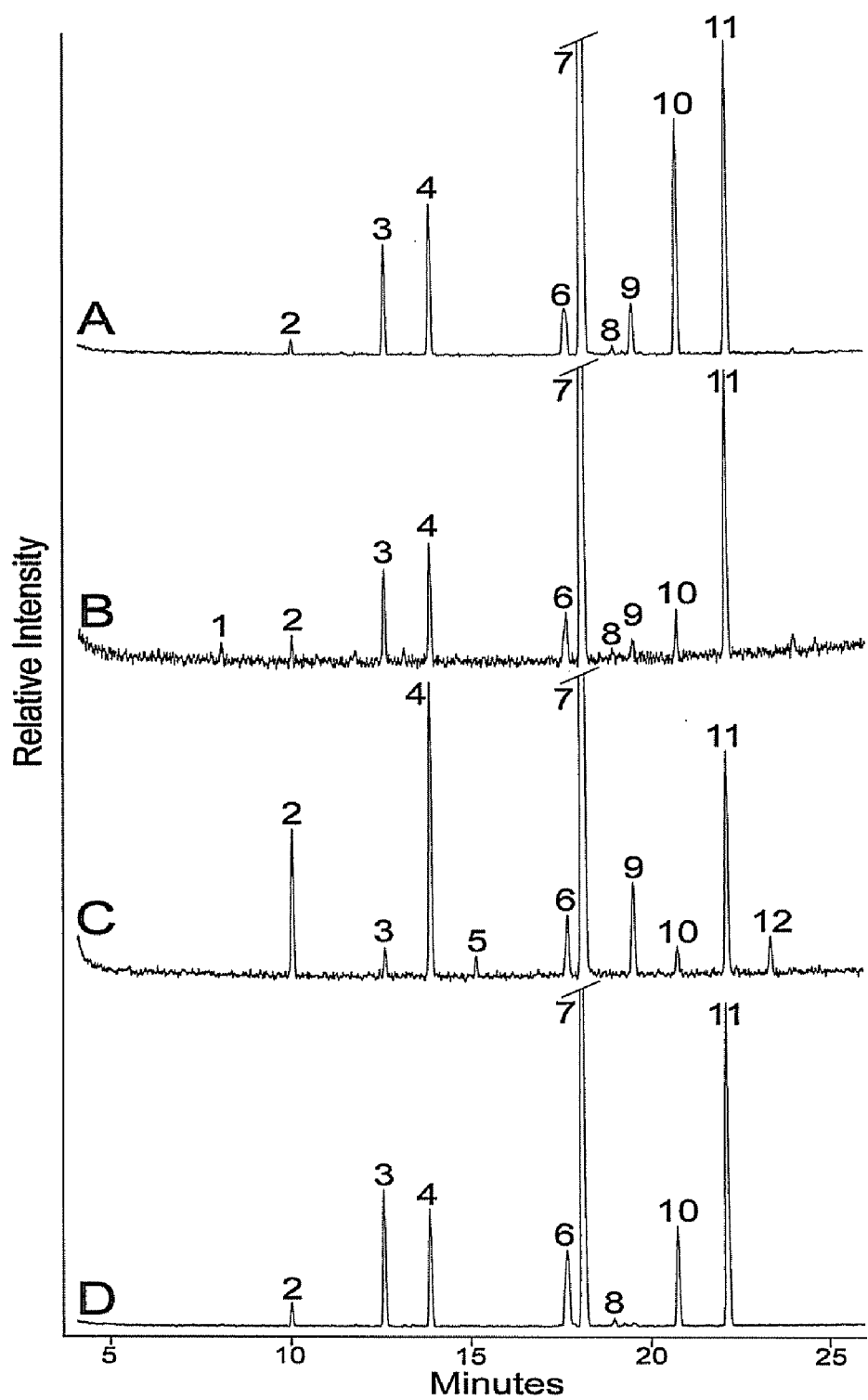
FIG. 7a illustrates a comparison of fatty acid methyl ester profiles for ethanologenic clostridia: (A) *C. ljungdahlii* PETC; (B) *C. autoethanogenum*; (C) *C. ragsdalei*; (D) *C. coskatii* (PS02). Compounds and corresponding peaks: (1) Methyl dodecanoate (8.161 minutes); (2) tetradecanal (10.046 minutes); (3) methyl tetradecanoate (12.61 minutes); (4) 1,1-dimethoxy-dodecane (13.881 minutes); (5) 1-methyl dodecylamine (15.176 minutes); (6) (Z)-13-octadecenal, (17.638 minutes); (7) methyl hexadecanoic acid, (18.138 minutes); (8) methyl-6,6-dimethoxy-octanoic acid (18.973 minutes); (9) 1,1-dimethoxy-tetradecane, (19.506 minutes); (10) cyclopropaneoctanoic acid, 2-hexyl-, methyl ester (20.735 minutes); (11) 1,1-dimethoxy-hexadecane (22.113 minutes); (12) 2-Oxo-3-methyl-cis-per hydro-, 1,3-benzoxazine (23.363 minutes).
Figures 7B, 7C:
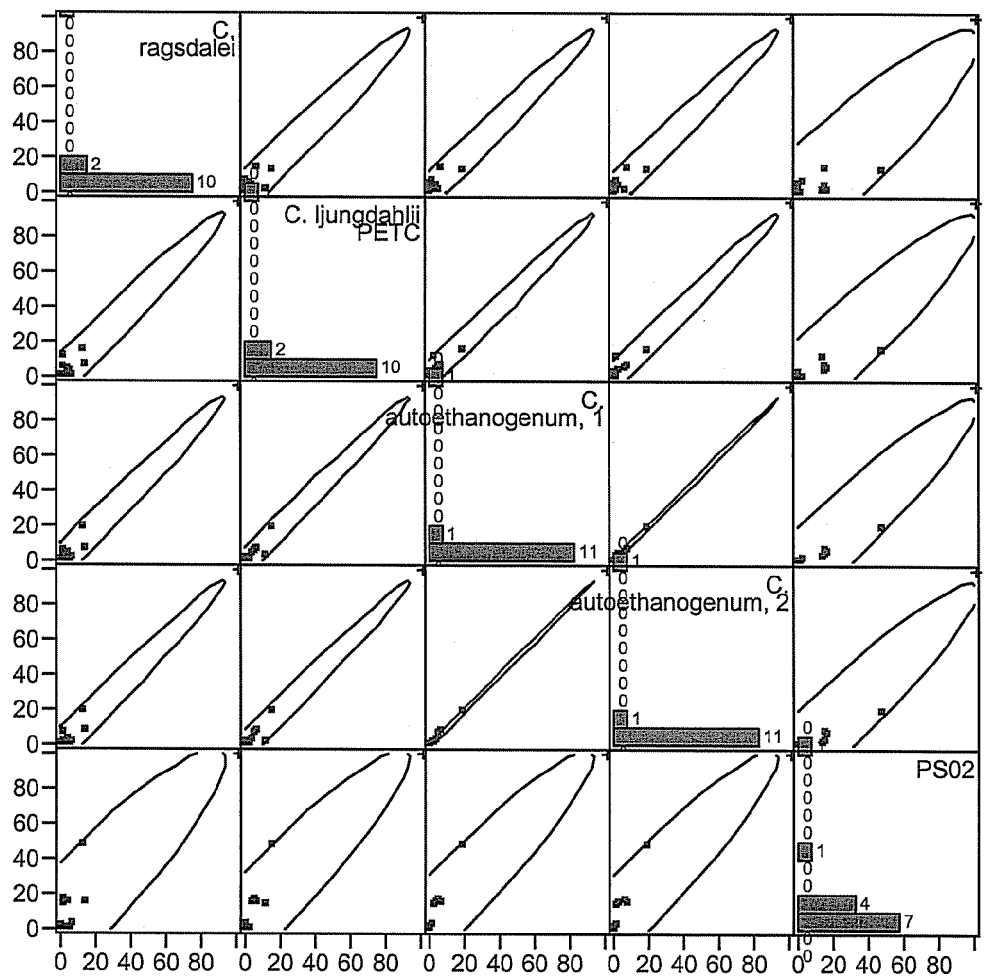

The fatty acid methyl ester composition of cellular biomass was determined for *Clostridium coskatii* (PS02), *Clostidium ragsdalei*, *Clostridium autoethanogenum*, and *Clostridium ljungdahlii*. Correlation coefficients for pair-wise comparisons showed that *Clostridium coskatii* (PS02) diverged in a range from 5% to 7% from other ethanologenic clostridia based on the cell membrane lipid composition. Divergence was driven by the concentration of 5 lipid components: 1,1-dimethoxy-hexadecane; 2-hexyl-cyclopropaneoctanoic acid, methyl ester; (Z)-13-Octadecenal; 1,1-dimethoxy-dodecane; and methyl tetradecanoate. Independent measurements of *C. autoethanogenum* are reported to demonstrate method reproducibility. (FIGS. 7a, 7b, and 7c)

Fatty acid methyl ester analysis was performed on an Agilent 6890N GC equipped with a 5975B electron-impact mass spectrometer (MS) and Ultra 2 capillary column according to the MIDI method of Shutter and Dick (2000). Peak identity was confirmed with a bacterial fatty acid methyl ester standard (47080U, Supelco, Bellefonte, Pa.).

EXAMPLE 6

16S rRNA Sequences

Figure 8B:
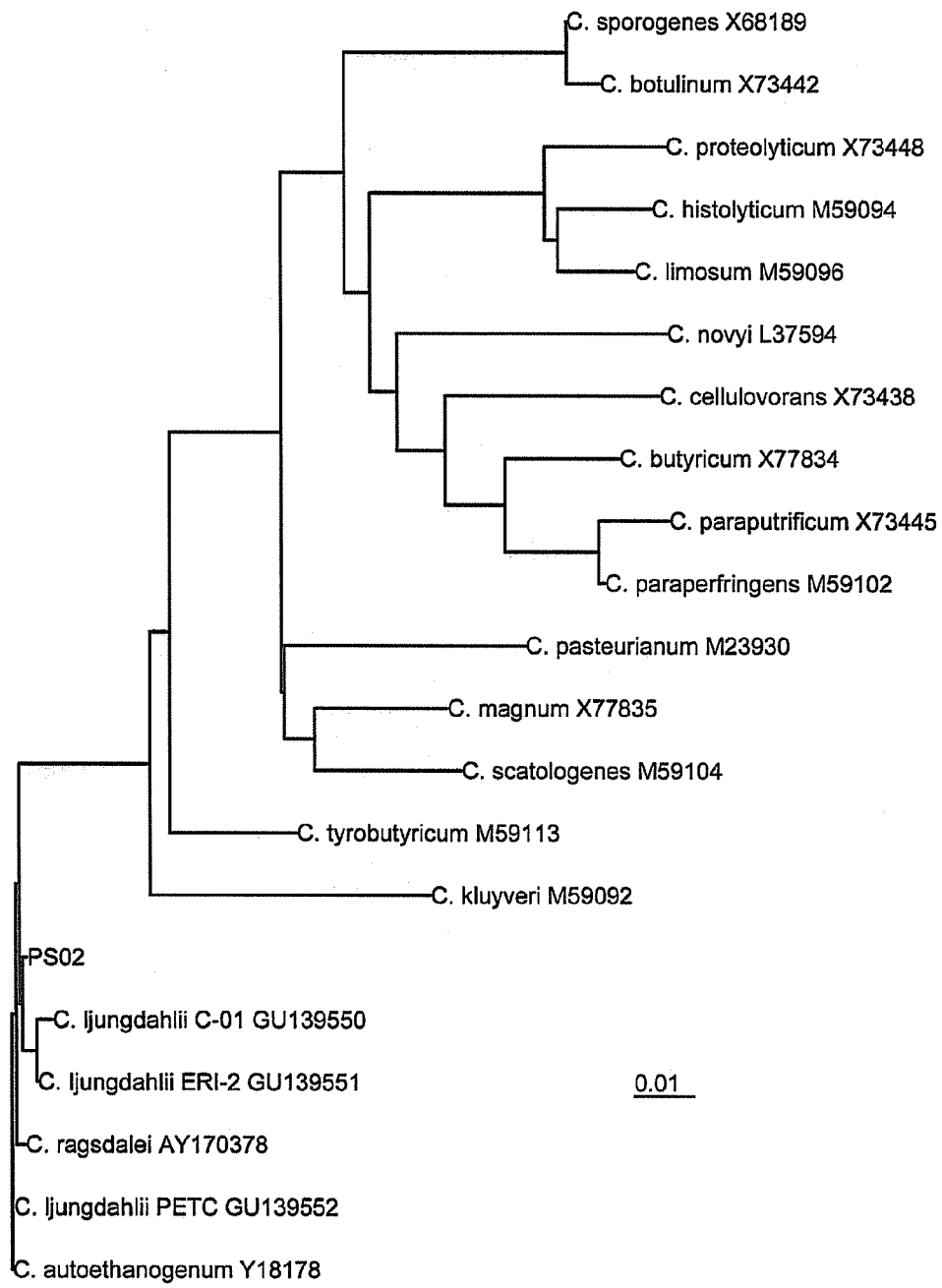
FIG. 8b illustrates a 16S rDNA parsimony tree of clostridial species. Bar corresponds to 1 nucleotide substitution per 100 sequence positions. The distance of the ethanologenic clostridial cluster (*C. coskatii* PS02) to other selected *clostridium* cluster I representatives is: *C. tyrobutyricum:* 95.18%; *C. magnum:* 93.01%; *C. kluyveri:* 92.96%; *C. scatologenes:* 92.52%.

Phylogenetic analysis of the 16S rDNA gene sequence (SEQ ID NO 3; FIG. 8a) of *Clostridium coskatii* (PS02) indicated that the organism belonged within clostridial rDNA homology group 1 (Collins et. al., 1994; Johnson & Francis 1975). There was a high overall level of conservation in the 16S rDNA sequences for representatives of the ethanologenic clostridia cluster. Pairwise analyses of 16S rRNA sequences for representatives of the ethanologenic clostridia cluster exceeded 99.27% similarity for all comparisons. In this cluster, *Clostridium coskatii* (PS02) was located within a group of five other clostridia; *C. ljungdahlii* C-01 (Gen Bank Accession No. GU139550), *C. ljungdahii* ERI-2 (GU129551), *C. ragsdalei* (AY170378), *C. ljungdahlii* PETC (GU139552) and *C. autoethanogenum* (Y18178) (FIG. 8b). Based on this analysis, *Clostridium coskatii* (PS02) is closely related to other ethanologenic acetogens in clostridial rDNA homology group 1, and is most closely related (99.86%) to *C. ljungdahlii* ERI-2 based on the Neighbor-Joining/UPGMA method (FIG. 9).

Figure 10:
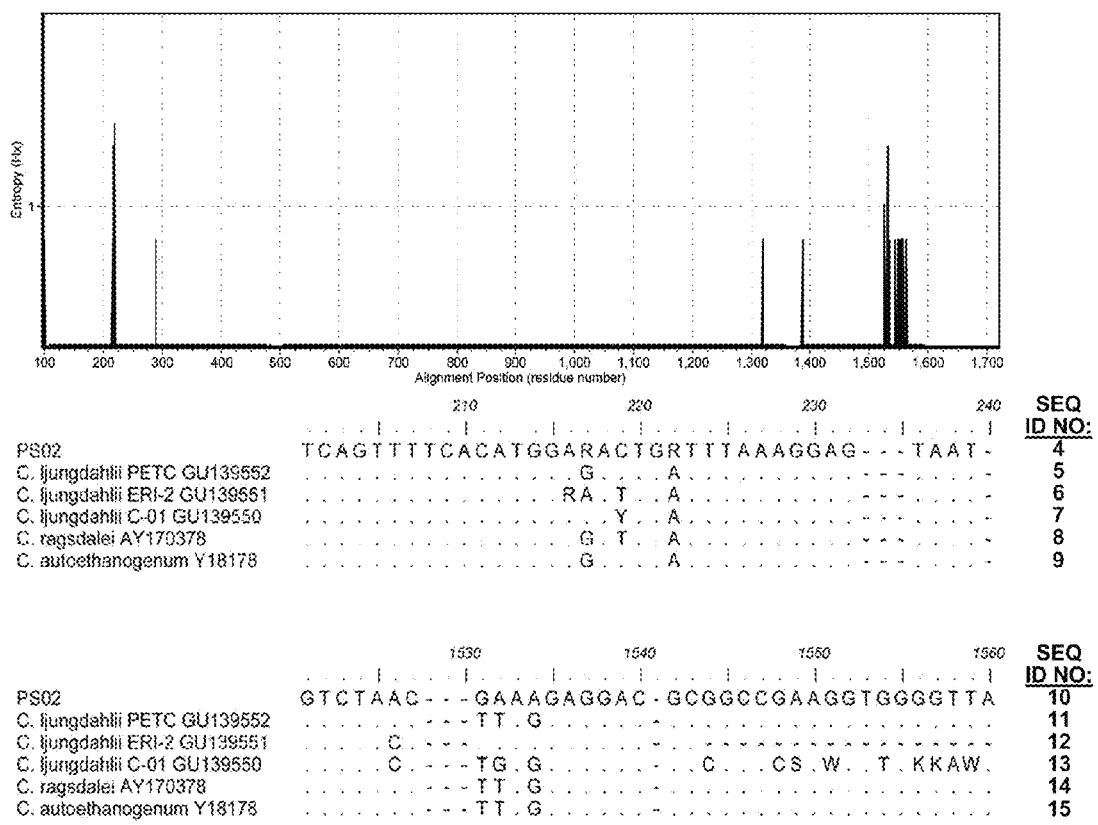
FIG. 10 illustrates an entropy plot showing the frequency of hypervariable regions in the 16S rDNA sequences for the six ethanologenic acetogens and the sequence alignment of those hypervariable regions.

The primary structure of the 16S rDNA gene is highly conserved, and species having 70% or greater genomic DNA similarity usually have more than 97% sequence identity for the 16S rDNA gene (Stackebrandt and Goebel, 1994). As with other organisms, these differences were not randomly scattered through the 16S rDNA sequence, but were concentrated in certain hypervariable regions. These hypervariable regions are known to be taxon specific and can only be determined by sequence analysis. Two regions of entropy in the 16S rDNA alignments provided identifying sequence features for each of the six ethanologenic acetogens. *Clostridium coskatii* (PS02) could be uniquely identified by the presence of key differentiating DNA bases within the hypervariable region of the 16S rDNA sequence (See Table H and FIG. 10). These unique sequence attributes are an indentifying feature of this organism.

TABLE H 16S rDNA base positions that distinguish Clostridium coskatii (PS02) from other ethanologenic acetogens.

| SEQ ID NO. | Starting Base Position | Sequence |
| --- | --- | --- |
| SEQ ID NO. 1 | 215 | GARACTGRTTT |
| SEQ ID NO. 2 | 1525 | AACGAAAGAGGACGCGCCCGAA |

The 16S rRNA analysis of the six clostridial ethanologens presented in this work shows that these bacteria are closely related on a phylogenetic level, and are well above the 97% sequence identity threshold requirement for determining individual species. The utility of 16S rRNA gene sequence for establishing new species for organisms that differ by <97% is well established. Scores of >97% are not clear, and require the use of methods with higher resolution such as DNA-DNA reassociation, or DNA fingerprinting (Janda and Abbot, 2007; Konstantinos and Tiedje, 2005).

Genomic DNA was isolated from ethanologenic clostridia using the ChargeSwitch® gDNA Mini Bacterial Kit using directions supplied by the manufacturer (#CS11301, Invitrogen, Carlsbad, Calif.). The full 16s rDNA sequence was performed according to the procedures described by Chandler et al. (1997). The universal primers used corresponded to positions 0005F and 1513R for the 1500 base pair (bp) sequence. Cycle sequencing of the 16S amplification products was carried out using DNA polymerase and dye terminator chemistry. The samples were electrophoresed on an ABI 3100 AVANT Genetic Analyzer. Sequence alignments and analyses were completed using BioEdit software version 7.0 (Hall, 1999). For reported sequences, G,A,T,C represent Guanine, Adenine, Thiamine, and Cytosine, respectively. The codes used for ambiguous bases is as follows: R (A or G), Y (C or T), W (A or T), S(C or G), K (G or T). The reproducibility of sequencing results was confirmed by comparing three independent sequencing runs for each organism. Three 16S rDNA sequences were deposited with GenBank since they resolved sequencing gaps associated with previously deposited sequences, or in the case of *C. ljungdahlii* C-01, the sequence did not previously exist in GenBank. These sequences were deposited under the following acquisition numbers: *C. ljungdahlii* C-01 (Gen Bank Accession No. GU139550), *C. ljungdahii* ERI-2 (GU129551), and *C. ljungdahlii* PETC (GU139552).

EXAMPLE 7

PCR-Based DNA Fingerprinting

One method for comparing closely related organisms is DNA fingerprinting by REP-PCR. This method makes use of DNA primers complementary to naturally-occurring, highly conserved repetitive DNA sequences that are present in multiple copies in most bacteria. The length and concentration of the amplicons that result from PCR provides a highly specific DNA fingerprint that can differentiate closely related species, or may be used to establish organisms that are genetically identical.

Three REP-PCR methods were used for DNA fingerprinting of ethanologenic acetogens, which included repetitive extragenic palindromic elements (REP-PCR), conserved repetitive DNA elements (BOX-PCR) and entrobacterial repetitive PCR intergenic consensus sequences (ERIC-PCR).

Figure 11:
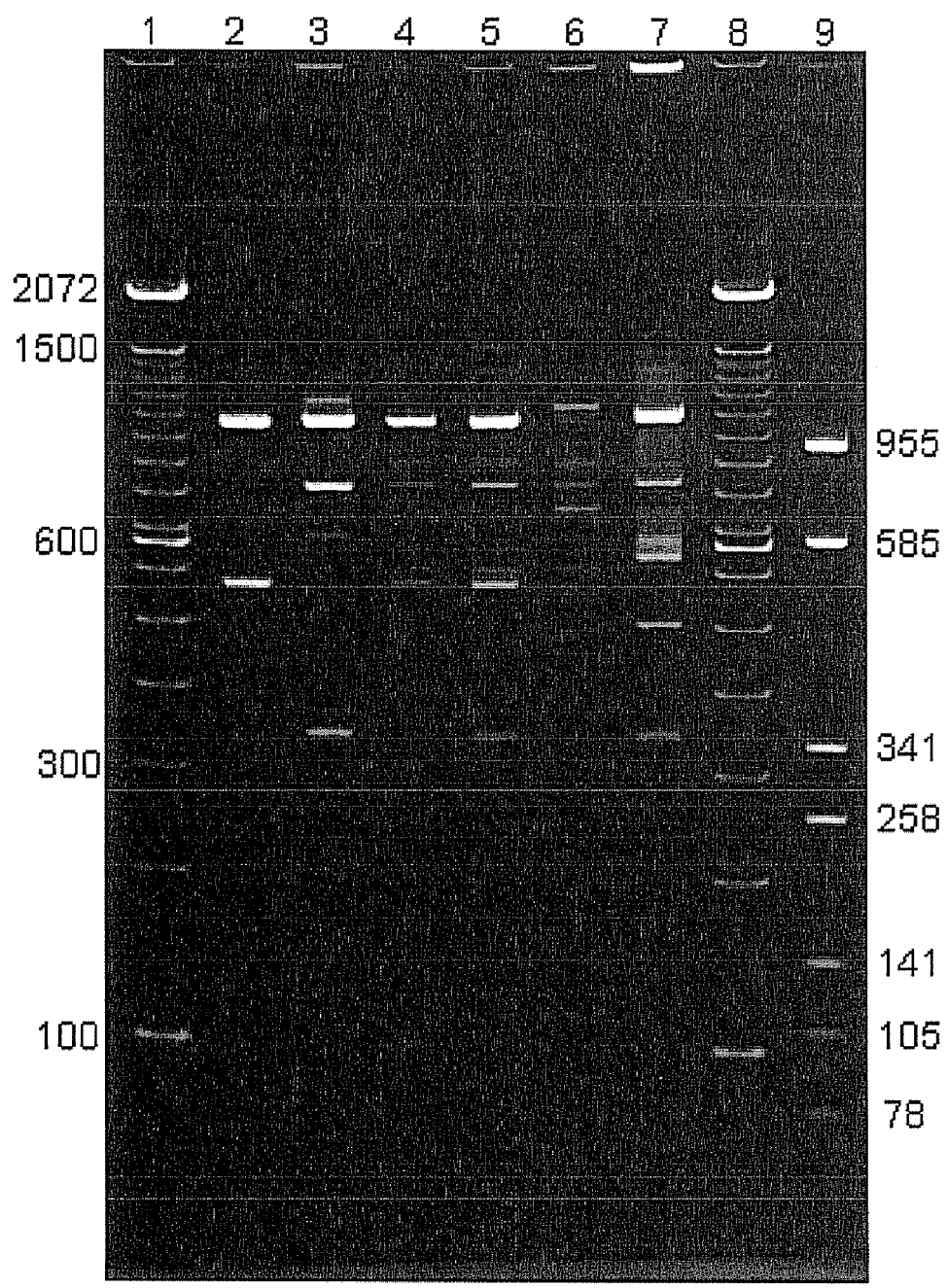
FIG. 11 illustrates a BOX-PCR comparison of ethanologenic clostridial species. Lane assignments are: (1) 100 bp ladder; (2) *C. coskatii* (PS02); (3) *C. ragsdalei* ATCC BAA-622; (4) *C. autoethanogenum* DSMZ 10061; (5) *C. ljungdahlii* PETC DSMZ 13528; (6) *C. ljungdahlii* C-01

For BOX-PCR, the PCR products from the six ethanologenic clostridia were generated and compared (FIG. 11). All organisms had bands of approximately 1122, 587, and 323 bp in common. *Clostridium coskatii* (PS02) was missing bands of approximately 868, 714, 362 and 301 bp. Statistical analysis by Pearson UPGMA correlation of PCR amplicons showed that *Clostridium coskatii* (PS02) was most closely related to *Clostridium autoethanogenum* (76.1%), and *Clostridium ljungdahlii* PETC (75.7%; FIG. 12). The magnitude of differences between amplicons that were generated by BOX-PCR appeared to be least informative due to the low number of amplicons generated, and the similarity in their masses. This result suggests that there are a low number of target BOX palindromic elements present in these genomes, and these elements are more highly conserved than those generated by REP-PCR and ERIC-PCR. Regardless, all ethanologenic clostridia were still readily shown by BOX-PCR to be different, and varied in a range between 24% and 90.1% similar.

The REP-PCR products from the six ethanologenic clostridia were generated and compared (FIG. 13). Seven major PCR amplicons were generated from *Clostridium coskatii* (PS02) using the REP-PCR method: They were 1884, 1436, 1139, 860, 785, 284, and 185 bp. The 284 bp amplicon was common with all ethanologenic clostridia, but varied in intensity among the six organisms. Additionally, the amplicon at 185 bp in *Clostridium coskatii* (PS02) was also present in *Clostridium ljungdahlii* PETC and ERI-2, but at a much lower intensity. The remaining PCR products for *Clostridium coskatii* (PS02) were unique to this organism. Statistical analysis by Pearson UPGMA correlation of PCR amplicons showed that *Clostridium coskatii* (PS02) was most closely related to *Clostridium ragsdalei* at 40.9% similarity. The range for REP-PCR similarity scores varied between 2.6% and 40.9% similar (FIG. 14). The REP-PCR method provided the greatest level of differentiation between *Clostridium coskatii* (PS02) and other ethanologenic clostridia, and would be the preferred DNA fingerprinting method for future bacterial typing studies.

The ERIC-PCR products from the six ethanologenic clostridia were generated and compared (FIG. 15). More than seventeen major PCR amplicons were generated from *Clostridium coskatii* (PS02) using the REP-PCR method. Under optimized conditions, the ERIC-PCR method provided a higher background of PCR products, apparently due to the lack of probe specificity. Nevertheless, statistical analysis of the amplicon patterns by Pearson UPGMA correlation showed that *Clostridium coskatii* (PS02) was most closely related to *Clostridium ljungdahlii* PETC at 73.5% similarity (FIG. 16). The range for REP-PCR similarity scores (42.7 to 73.5%) was much narrower than other methods, and indicated that REP-PCR may be less desirable than the REP-PCR method for bacterial typing of ethanologenic acetogens.

Genomic DNA was isolated from ethanologenic clostridia using the ChargeSwitch® gDNA Mini Bacterial Kit using directions supplied by the manufacturer (#CS11301, Invitrogen, Carlsbad, Calif.). Three REP-PCR methods were used to generate amplicons from genomic DNA: These were (a) repetitive DNA elements (BOX-PCR), repetitive extragenic palindromic elements (REP-PCR), and enterobacterial repetitive intergenic consensus sequences (ERIC-PCR). REP-PCR for the three methods was carried out as described by Rahmati et al., (2005) with modifications proposed by MacCannel et al., (2006). Primers were synthesized by Invitrogen Corporation using the sequences provided by Rahmati et al., (2005). Molecular typing and statistical analysis of amplicon patterns was completed using BioNumerics 4.01 software (Applied Maths, Ft. Worth, Tex.). Two molecular weight markers were loaded on the gels at a concentration of approximately 0.1 to 0.3 μg (100 bp DNA ladder, 10488-058, Invitrogen; and pUC19/Sau3A 1 digest, AM7760, Invitrogen); however, molecular weight assignments were based on the AM7760 standard.

EXAMPLE 8

Comparison of G+C Content of DNA

The mol % G+C of the DNA from *Clostridium coskatii* (PS02) was 32.5%±0.5% G+C (n=5), which was 3 to 10% higher than other known ethanologenic clostridia. The G+C content of these bacteria fall within the expect range of low G+C gram positive bacteria (Drake, et al., 2002; and Drake et al., 2006). G+C content for *Clostridium coskatii* (PS02) and the three most closely related ethanologenic clostridia (according to DNA fingerprinting) is provided in Table I.

TABLE I

G + C content for clostridial species

| Species | G + C Content |
| --- | --- |
| *Clostridium autoethanogenum* DSMZ 10061 | 25.9 ± 0.6% G + C |
| *Clostridium ljungdahlii* PETC DSMZ 13528 | 22.5 ± 0.5% G + C |
| *Clostridium ragsdalei* ATCC BAA-622 | 29.5 ± 0.5% G + C |
| *Clostridium coskatii* PS02 | 32.5 ± 0.5% G + C |

Bacterial cells were disrupted with french pressure cell and the DNA was purified on hydroxyapatite according to the procedure of Cashion et al. (1977). Next, the DNA was hydrolyzed with P1 nuclease and the nucleotides were dephosphorylized with bovine alkaline phosphatase (Mesbah et al. 1989). The resulting deoxyribonucleosides were analyzed by HPLC. The HPLC System (Shimadzu Corp., Japan) consisted of the following modules: LC-20AD solvent delivery module, DGU-3A online degasser, CTO-10AC column oven, SIL-20A automatic sample injector, and a SPD-6A UV spectrophotometric detector. Chromatograms were analyzed using the CLARITY (Version 2.4.1.93) software package (DataApex Ltd., Czech Republic). The analytical column was a VYDAC 201SP54, $C_{18}$, 5 μm (250×4.6 mm) equipped with a guard column 201GD54H (Vydac, Hesperia, Calif. 92345, USA). The liquid chromatography conditions were: Temperature 45° C., 10 μl sample, solvent 0.3 M ($NH_4$)$H_2PO_4$/acetonitrile, 40:1 (v/v), pH 4.4, 1.3 ml/min (adapted from Tamaoka & Komagata, 1984). The reference DNA used for system calibration included: Non-methylated Lambda-DNA (Sigma), GC-content 49.858 mol % (Mesbah et al., 1989) and 3 DNAs for which complete genome sequences were published (http://ergo.integratedgenomics.com/GOLD/): *Bacillus subtilis* DSMZ 402 (43.518 mol % G+C); *Xanthomonas campestris* pv. *campestris* DSMZ 3586$^T$ (65.069 mol % G+C); and *Streptomyces violaceoruber* DSMZ 40783 (72.119 mol % G+C). The G+C value was calculated from the ratio of deoxyguanosine (dG) and thymidine (dT) according to the method of Mesbah et al. (1989).

EXAMPLE 9

DNA-DNA Hybridization

DNA fingerprinting studies indicated that *Clostridium coskatii* (PS02) was most closely related to *Clostridium autoethanogenum, Clostridium ljungdahlii* PETC, and *Clostridium ragsdalei*. Based on these results, a DNA-DNA hybridization study was performed with these organisms to determine similarity of the genomic DNA. DNA-DNA hybridization is unequivocally the preferred method for proposed new species and for the definitive assignment of an organism with ambiguous properties to the correct taxonomic unit (Stackebrandt et al., 2002). The phylogenetic definition of a species includes that (a) the purified DNA molecules show 70% or greater DNA-DNA relatedness, (b) have a 5° C. or less ΔTm for the stability of heteroduplex molecules, and (c) the phenotypic characteristics should agree with this definition (Wayne et al, 1987; Stackebrandt and Goebel, 1994).

All pairings for *Clostridium coskatii* met species requirements when a threshold value of 70% DNA-DNA similarity was used (Table J). This result indicated that *Clostridium coskatii* (PS02) represented a new bacterial species. All other pairings were below the 70% threshold value except for *Clostridium ljungdahlii* and *Clostridium autoethanogenum*, for which the confidence interval overlapped at the 70% threshold value.

TABLE J

DNA-DNA hybridization results

|  | PS02 | *Clostridium autoethanogenum* DSMZ 10061 | *Clostridium ljungdahlii* PETC DSMZ 13528 |
| --- | --- | --- | --- |
| *Clostridium autoethanogenum* DSMZ 10061 | 66.5 ± 4.0 | X | X |
| *Clostridium ljungdahlii* PETC DSMZ 13528 | 68.9 ± 1.0 | 76.7 ± 7.0 | X |
| *Clostridium ragsdalei* ATCC BAA-622 | 64.3 ± 4.1 | 58.7 ± 3.6 | 62.6 ± 6.1 |

Genomic DNA was sheared and released from bacterial cells using a French pressure cell (Thermo Spectronic) and was purified by chromatography on hydroxyapatite as described by Cashion et al. (1977). DNA-DNA hybridization was carried out as described by De Ley et al. (1970) under consideration of the modifications described by Huss et al. (1983) using a model Cary 100 Bio UV/VIS-spectrophotometer equipped with a Peltier-thermostatted 6×6 multicell changer and a temperature controller with in-situ temperature probe (Varian). Results are reported as the average from two independent analyses, which differed by less than 10%. Similarity values were reproducible in a range of approximately 10% of the reported value.

EXAMPLE 10

Ethanol and Acetate Productivity

Long-term (>1,000 hours) Continuous Stirred Tank Reactors (CSTR) experiments were performed to determine ethanol and acetate productivity of *Clostridium coskatii* (PS02) under steady-state fermentation conditions. A fermentation balance for this organism was determined while growing in CSTR mode on a simple inexpensive chemically-defined medium and using synthesis gas as the electron and carbon source. During steady-state conditions, the utilization of trace metals was measured to investigate nutrient deficiencies with the chemically-defined medium.

A Sartorious Biostat B CSTR was operated at 37° C. utilizing Acetogen C5 media, which was prepared using the strict anaerobic technique described by Balch and Wolfe (1976). This media was essentially the same as Acetogen C3 medium, except that sodium sulfide, yeast extract, and the MES buffer were omitted, and an antifoam agent, such as Antifoam A (Sigma Chemical, St. Louis, Mo.) was added to the medium at a final concentration of 20 mg/L. The pH of the fermentation was controlled throughout the duration of the process at 5.20±0.1 using 5M sodium hydroxide.

Semi-continuous (20 minute intervals) analysis of inlet and outlet gas concentrations of CO, $H_2$, $CO_2$, $N_2$, $CH_4$, and ethanol was performed using a ThermoElectron Prima δB process gas mass spectrometer. Reactor operation was divided into two major processes: Reactor startup, which was completed under batch conditions, and CSTR ethanol production phase. After inoculation of the reactor with a 10% inoculum, the reactor was operated in batch mode until the cell density increased to 0.2 g dry cell weight per liter of broth (g DCW/L). At that time, a continuous feed consisting of Acetogen C5 media was started using a dilution rate (D) of 0.2 $day^{-1}$. During start-up and throughout the ethanol production phase, a synthesis or waste gas consisting of CO, $H_2$ and $CO_2$ in a composition of 37% CO, 21.68% $CO_2$, 35.1% $H_2$ and 6.22% $N_2$ was continuously introduced into the bioreactor. Gas flow and agitation were raised at a rate to maintain hydrogen uptake in excess of 70%. Finally, the feed media rate was increased to a final value of D=0.5 $day^{-1}$ over a time period of 48 hours after the cell density exceeded 0.60 g DCW/L.

The maximum doubling time for pre-steady state chemostat cultures during early exponential growth phase for *Clostridium coskatii* (PS02) when using Acetogen C5 media was 0.064 $hr^{-1}$. During ethanol production phase, and steady-state chemostat growth, the growh rate decrease by 75 to 100-fold, and remained stable for up to 1,150 hours of CSTR operation (FIG. 17).

The elemental profile of biomass collected from a CSTR fermentation of *C. coskatii* (PS02) was compared to published results for *C. ljungdahlii* PETC (Tanner et al., 1993). When compared to *C. ljungdahlii* PETC, the sample of *C. coskatii* biomass contained significantly more phosphorus and sulfur, but a similar level of potassium and oxygen (FIG. 18). This result indicated that there were significant differences in the cellular composition of elements for these two types of ethanologenic clostridia.

Gas uptake, biomass production, and product formation by *Clostridium coskatii* (PS02) was measured for a CSTR over a period of 1,150 hours (FIGS. 19 and 20). During this period, *Clostridium coskatii* was grown on Acetogen C5 media with 0.1 g cysteine free base per liter, under 37% CO, 21.68% $CO_2$, 35.1% $H_2$ and 6.22% $N_2$. By approximately 200 hours, the gas flow, agitation, dilution rate, and cell density reached their final steady-state values of 0.27 vvm, 900 rpm, 0.5 $day^{-1}$, and 1.733 g DCW/L, respectively. After 10 days of CSTR operation, and a dilution rate of 0.5 $day^{-1}$, a steady-state condition was achieved for the reactor (at 440 hours). Both LC and GC-MS analyses of the broth showed two major products were produced from the fermentation; they were acetate, and ethanol (FIG. 21). There were also trace amounts of ethyl acetate and formic acid, ethyl ester, which were acid-catalyzed chemical reaction products of metabolic intermediates (formate) or final end products (acetate and ethanol) (FIG. 21).

After reaching a steady state condition, a mass balance was completed on the fermentation to confirm that *Clostridium coskatii* was using the Acetyl CoA pathway. The mean and standard deviation for the uptake of CO, and $H_2$, and the emission of $CO_2$ and ethanol vapor were calculated for a 470 hour time-period that started at 440 hours and ended at 910 hours. In addition to measuring gaseous compounds, the amount of biomass, ethanol, acetate, and the fermentation volume were measured in the broth fraction during this period (FIGS. 22a and 22b). The mean values for this mass balance were:

Ethanol production: 5.365 mmol/L/hr
Acetic acid production: 3.745 mmol/L/hr
Ethanol vented: 0.144 mmol/L/hr
Biomass production: 0.0533 mmol/L/hr
CO uptake: 28.27 mmol/L/hr
$H_2$ uptake: 20.58 mmol/L/hr
$CO_2$ uptake: −8.52 mmol/L/hr (negative uptake)

TABLE K

Electron balance under steady-state CSTR conditions for *Clostridium coskatii* (PS02).

| Component | Concentration, mmol | Electron equivalents |
|---|---|---|
| CO (in) | 28.27 | 56.54 |
| $H_2$ (in) | 20.58 | 41.16 |
| $CO_2$ | 8.52 | n/a |
| Biomass | 0.0533 | n/a |
| Ethanol (out) | 5.509 | 66.11 |
| Acetate (out) | 3.745 | 29.96 |
| Electrons in | | 97.700 |
| Electrons out | | 96.068 |
| Balance | | 1.017 |
| Error, % | | 1.04% |

The electron balance in Table K shows excellent agreement between the concentration of electron donors feeding into the process and the concentration of electron acceptors (acetate and ethanol) that are produced from the bacterium. Closure of the electron balance to 1.04% provides a confirmation that no other major products were present in the fermentation broth (Table K).

The carbon balance for clostridial ethanologens, such as *Clostridium coskatii* (PS02) is complicated by the fact that there are both consuming, and producing reactions for $CO_2$ when a mixture of CO and $H_2$ is co-metabolized (see reactions on p. 5). Oxidation of CO by the carbon monoxide dehydrogenase is the main reaction for producing $CO_2$ under minimal media conditions, and the acetyl Co-A pathway, with electrons derived through the oxidation of $H_2$ by the hydrogenase is the main consuming pathway for uptake of $CO_2$. For a biochemical system that is producing a mole ratio of roughly 1:1 ethanol to acetate, every mole of $H_2$ that is oxidized results in 0.41666 moles of $CO_2$ are fixed to acetyl CoA (this value is calculated from the average $H_2$ to $CO_2$ ratio for acetate [2:1] and ethanol [3:1] production). For the example below, the amount of $CO_2$ consumed through electrons acquired from the hydrogenase can be estimated by dividing the total mmoles of hydrogen utilized by 2.40.

The carbon balance for this CSTR fermentation is shown in Table L. The carbon balance shows that the metabolism of *Clostridium coskatii* (PS02) fits the acetogenic model. Furthermore, the measured error for the experiment is less than 1%, which again confirms that all reactants and products have been accurately measured, and that there are no other major products that are being produced in this syngas fermentation.

TABLE L

Carbon balance under steady-state CSTR conditions for *Clostridium coskatii* (PS02). Non-carbon containing compounds ($H_2$) are included in the table for calculation of the fixed $CO_2$ value, but they are not directly used in the carbon balance.

| CO | $H_2$ | $CO_2$ | → | $CO_2$ | Ethanol | Acetate | Biomass |
|---|---|---|---|---|---|---|---|
| mmoles of reactants or products: | | | | | | | |
| 5.16 | 1.72 | 0.716 | | 3.29 | 1.00 | 0.26 | 0.014 |
| mmoles of carbon equivalents: | | | | | | | |
| 5.16 | | 0.716 | → | 3.29 | 2.00 | 0.52 | 0.014 |
| Total carbon equivalents: | | | | | | | |
| | | 5.876 | → | 5.824 | | | |
| | | | Error, % | | | | |
| | | | 0.9% | | | | |

EXAMPLE 11

Effect of an Organic Carbon Source on Ethanol and Acetate Productivity—Validation of a Chemically-Defined Minimal Medium The effect of the organic carbon source, yeast extract was evaluated in long-term (>700 hours) Continuous Stirred Tank Reactors (CSTR) containing *Clostridium coskatii* under steady-state fermentation conditions. Through these studies, it was shown that *Clostridium coskatii* grew well in the absence of complex organic carbon sources. This trait had not been previously demonstrated for other known clostridial ethanologens, and therefore, was unique to *Clostridium coskatii*. CSTR studies were completed with a chemically-defined minimal medium, and a medium supplemented with 0.1 g/L yeast extract to further characterize the effect of complex organic carbon sources on ethanol and acetate production by *Clostridium coskatii*.

A Sartorious Biostat B CSTR was operated at 37° C. utilizing Acetogen C5 media, as previously described in Example 10. Reactor conditions and operating procedures were identical to those described previously in Example 10.

The effect of yeast extract on ethanol and acetate production by *Clostridium coskatii* (PS02) was measured for the two CSTRs over a period of 720 hours (FIG. 23). During reactor startup and before establishment of steady-state conditions, acetate and ethanol production was similar for the control reactor, which contained no yeast extract in the feed medium, and the reactor feed supplemented with 0.1 g/L yeast extract. Similarity in product trends during reactor startup was due to the carry over of nutrients from the inoculum; these carry over nutrients were depleted by more than 60% of their original concentration at 192 hours based on the dilution rate of 0.2 day$^{-1}$, and differences in the acetate and ethanol trends became significant at this time. When the dilution rate was increased to 0.5 day$^{-1}$ at 200 hours, the differences in acetate and ethanol production became more pronounced, in that the ethanol concentration increased to a steady-state condition of 24 g/L in the control reactor, but dropped to less than 1 g/L in the reactor supplemented with 0.1 g/L yeast extract. These changes in ethanol production were linked with a 2-fold increase (23 g/L) in acetate production for the reactor supplemented with 0.1 g/L yeast extract, while the acetate levels in the control reactor remained at a constant, steady-state level of approximately 12 g/L throughout the duration of the experiment. These data show that a chemically-defined minimal media, equivalent to Acetogen C5 media is optimal for production of biofuels via synthesis gas fermentation using *Clostridium coskatii*.

While the present invention has been described in terms of its preferred embodiments, those skilled in the art will recognize that the *Clostridium coskatii* bacterium of the invention can be utilized in a variety of ways within the spirit and scope of the appended claims. Accordingly, the present invention should not be limited to the specific embodiments described above.

We claim:

1. An isolated biologically pure culture of the microorganism *Clostridium coskatii* having the genotypic characteristics of ATCC No. PTA-10522.

2. An isolated biologically pure culture of the microorganism *Clostridium coskatii*, ATCC No. PTA-10522 having the ability, under anaerobic conditions, to produce ethanol from gaseous substrates selected from the group consisting of carbon monoxide, carbon dioxide and hydrogen or combinations thereof.

3. The isolated biologically pure culture of claim 2 wherein the gaseous substrates are provided by syngas.

4. An isolated biologically pure culture of the microorganism *Clostridium coskatii*, ATCC No. PTA-10522 having the ability, under anaerobic conditions, to produce acetate from gaseous substrates selected from the group consisting of carbon monoxide, carbon dioxide and hydrogen or combinations thereof.

5. The isolated biologically pure culture of claim 4 wherein the gaseous substrates are provided by syngas.

6. An isolated biologically pure culture of the microorganism *Clostridium coskatii*, ATCC No. PTA-10522 having the ability to produce ethanol from an anaerobic aqueous nutrient medium comprising sources of carbon.

7. The isolated biologically pure culture of claim 6 where the source of carbon is not an organic complex carbon source.

8. The isolated biologically pure culture of claim 6 where the source of carbon is not yeast extract.

9. An isolated pure culture of the microorganism *Clostridium coskatii*, ATCC No. PTA-10522 having the ability to biosynthesize acetate from an anaerobic aqueous nutrient medium composed of an organic carbon source.

10. An isolated pure culture of the microorganism *Clostridium coskatii* having 16S rDNA sequences as set forth in SEQ ID NO. 1, SEQ ID NO. 2, and SEQ ID NO. 3.

* * * * *

UNITED STATES PATENT AND TRADEMARK OFFICE
CERTIFICATE OF CORRECTION

| | | |
|---|---|---|
| PATENT NO. | : 8,143,037 B2 | |
| APPLICATION NO. | : 12/727320 | |
| DATED | : March 27, 2012 | |
| INVENTOR(S) | : James A. Zahn and Jyotisna Saxena | |

It is certified that error appears in the above-identified patent and that said Letters Patent is hereby corrected as shown below:

Delete the title page and substitute therefore the attached title page consisting of corrected number of drawing sheets in patent.

Delete Drawing Sheets 1-26 and substitute therefore the attached Drawing Sheets 1-27. Fig. 8A has been replaced.

Col. 4, lines 8-9: delete "[ phase" and insert --Clostridium coskatii (PS02) in early exponential growth-- so that the lines recite "FIG. 1 is a transmission electron micrograph of a negative stained Clostridium coskatii (PS02) in early exponential growth, 25,000X magnification. Bar = 1.0 µm."

Signed and Sealed this
Twenty-ninth Day of May, 2012

David J. Kappos
*Director of the United States Patent and Trademark Office*

(12) United States Patent
Zahn et al.

(10) Patent No.: US 8,143,037 B2
(45) Date of Patent: Mar. 27, 2012

(54) **ETHANOLOGENIC *CLOSTRIDIUM* SPECIES, *CLOSTRIDIUM COSKATII***

(75) Inventors: James A. Zahn, Campton Hills, IL (US); Jyotisna Saxena, Naperville, IL (US)

(73) Assignee: Coskata, Inc., Warrenville, IL (US)

( * ) Notice: Subject to any disclaimer, the term of this patent is extended or adjusted under 35 U.S.C. 154(b) by 0 days.

(21) Appl. No.: 12/727,320

(22) Filed: Mar. 19, 2010

(65) Prior Publication Data
US 2011/0229947 A1 Sep. 22, 2011

(51) Int. Cl.
*C12P 7/06* (2006.01)
*C12N 1/20* (2006.01)
(52) U.S. Cl. ............................ 435/161; 435/252.7
(58) Field of Classification Search .................. None
See application file for complete search history.

(56) References Cited

U.S. PATENT DOCUMENTS

| | | | |
|---|---|---|---|
| 5,173,429 | A | 12/1992 | Gaddy et al. |
| 5,192,673 | A | 3/1993 | Jain et al. |
| 5,593,886 | A | 1/1997 | Gaddy |
| 5,807,722 | A | 9/1998 | Gaddy |
| 6,136,577 | A | 10/2000 | Gaddy |
| 6,753,170 | B2 | 6/2004 | Gaddy et al. |
| 7,285,402 | B2 | 10/2007 | Gaddy et al. |
| 2007/0275447 | A1 | 11/2007 | Lewis et al. |
| 2008/0057554 | A1 | 3/2008 | Huhnke et al. |
| 2008/0305539 | A1 | 12/2008 | Hickey et al. |
| 2009/0017512 | A1 | 1/2009 | May et al. |

FOREIGN PATENT DOCUMENTS

WO 2008/028055 A2 3/2008

OTHER PUBLICATIONS

Abrini, et al., "*Clostridium autoethanogenum*, sp. nov., an anaerobic bacterium that produces ethanol from carbon monoxide", Arch. Microbiol., vol. 161: pp. 345-351, 1994.
Arora et al., "Production of Ethanol From Refinery Waste Gases", Phase II — Technology Development Annual Report, Jul. 1995.
Balch, et al., "Methanogens: reevaluation of a unique biological group", Microbiol. Rev., vol. 43(2): pp. 260-296, Jun. 1979.
Balch, et al., "New approach to the cultivation of methanogenic bacteria: 2-mercaptoethanesulfonic acid (HS-CoM)-dependent growth of Methanobacterium ruminantium in a pressureized atmosphere", Appl. Environ. Microbiol.; vol. 32(6): pp. 781-791, Dec. 1976.
Barik, et al., "Biological Production of Alcohols from Coal Through Indirect Liquefaction", Appl. Biochem. Biotechnol. vol. 18: pp. 363-378, 1988.
Barik et al., Wise, D.L. (editor), "Bioprocessing and Biotreatment of Coal", New York: Marcel Dekker, Inc.; pp. 131-154, 1990.
Bryant, et al., "Commentary on the Hungate technique for culture of anaerobic bacteria", Am Journal Clinical Nutrition vol. 25: pp. 1324-1328, Dec. 1972.
Cashion, et al., "A rapid method for base ratio determination of bacterial DNA", Analytical Biochemistry vol. 1: pp. 461-466, 1977.
Collins, "The phylogeny of the genus *Clostridium*: Proposal of Five New Genera and Eleven New Species Combinations", International Journal of Systematic Bacteriology, vol. 44 (4): pp. 812-826, 1994.
De Ley, et al., "The Quantitative Measurement of DNA Hybridization from Renaturation Rates", Eur. J. Biochem. vol. 12: pp. 133-142, 1970.
Drake, et al., "Acetogenic Prokaryotes", Prokaryotes, Chapter 1.13, vol. 2: pp. 354-420, 2006.
Grethlein et al., "Continuous Production of Miexed Alcohols and Acids from Carbon Monoxide", Applied biochemistry & Biotechnology, vol. 24/25, pp. 875-884, 1990.
Huss, V. A. R., Festl, H. & Schleifer, K. H. 1983. Studies on the Spectrophotometric determination of DNA hybridization from renaturation rates. Syst Appl Microbiol. 4, 184-192.
Inokuma, et al., "Characterization of enzymes involved in the ethanol production of *Moorella* sp HUC22-1", Archives of Microbiol. vol. 188(1): pp. 37-45, 2007.
Johnson, "Taxonomy of the Clostridia: Ribosomal Ribonucleic Acid Homologies among the Species", J Gen Microbiol, vol. 88: pp. 229-244, 1975.
Liou et al., 2005, Int. J. Syst. Envol. Microbiol. 55: 2085-2091.
Skerman, V. B. D., McGowan, V. & Sneath, P. H. A. (editors), "Approved Lists of Bacterial Names"—(amended edition). Washington, DC: American Society for Microbiology; pp. 40-59, 1989.
Tanner, et al., "*Clostridium ijungdahlii* sp. nov., an acetogenic species in clostridial rRNA homology group I", Int J Syst Bacteriol; Apr. 1993; 43(2), pp. 232-236.
International Search Report of International Application No. PCT/US2011/028711, dated Nov. 28, 2011.

*Primary Examiner* — Tekchand Saidha
*Assistant Examiner* — MD. Younus Meah
(74) *Attorney, Agent, or Firm* — McDonnell Boehnen Hulbert & Berghoff LLP

(57) ABSTRACT

An isolated clostridia bacterial species (*Clostridium coskatii* ATCC No. PTA-10522, "PS02") is provided. Under anaerobic conditions *C. coskatii* can convert CO and/or $H_2$ and/or $CO_2$ to ethanol or acetate. Thus, this bacterium is capable of transforming waste gases (e.g. syngas and refinery wastes) into useful products.

10 Claims, 27 Drawing Sheets

FIG. 8a.

```
              10           20           30           40
    .....|....|....|....|....|....|....|....|....|
  1 ---------TGGAGAGTTTGATCCTGGCTCAGGACGAACGCT 50           60           70           80
         .|....|....|....|....|....|....|....|....|
 34 GGCGGCGTGCTTAACACATGCAAGTCGAGCGATGAA----

90          100          110          120
         .|....|....|....|....|....|....|....|....|
 69 ----G-CTCCTTCGG---GAG--------TGGATTAGCGGC 130          140          150          160
         .|....|....|....|....|....|....|....|....|
 95 GGACGGGTGAGTAACACGTGGGTAACCTACCTCAAAGAGG 170          180          190          200
         .|....|....|....|....|....|....|....|....|
135 GGGATAGCCTCCCGAAAGGGAGATTAATACCGCATAATAA 210          220          230          240
         .|....|....|....|....|....|....|....|....|
175 TCAGTTTTCACATGGARACTGRTTTAAAGGAG---TAAT- 250          260          270          280
         .|....|....|....|....|....|....|....|....|
210 --CCGCTTTGAGATGGACCCGCGGCGCATTAGCTAGTTGG 290          300          310          320
         .|....|....|....|....|....|....|....|....|
249 TAGGGTAACGGCCTACCAAGGCGACGATGCGTAGCCGACC 330          340          350          360
         .|....|....|....|....|....|....|....|....|
289 TGAGAGGGTGATCGGCCACATTGGAACTGAGAGACGGTCC 370          380          390          400
         .|....|....|....|....|....|....|....|....|
329 AGACTCCTACGGGAGGCAGCAGTGGGAATATTGCACAAT 410          420          430          440
         .|....|....|....|....|....|....|....|....|
369 GGGCGAAAGCCTGATGCAGCAACGCCGCGTGAGTGAAGAA 450          460          470          480
         .|....|....|....|....|....|....|....|....|
409 GGTTTTCGGATTGTAAAGCTCTGTCTTTCGGGACGA----
```

Fig. 8a continued

```
             490           500           510           520
             |             |             |             |
444  -TAA----------------------TGACGGTACC-CAAGGA 530           540           550           560
             |             |             |             |
464  GGAAGCCACGGCTAACTACGTGCCAGCAGCCGCGGTAATA 570           580           590           600
             |             |             |             |
504  CGTAGGTGGCGAGCGTTGTCCGGAATTACTGGG-CGTAA- 610           620           630           640
             |             |             |             |
541  ---AGAGTGCGTAGGCGGATATTTAAGTGAGATGTGAAAT 650           660           670           680
             |             |             |             |
579  ACCCG-GGCTTAACCCGGC-ACTGCATTTC-AAACTGGA 690           700           710           720
             |             |             |             |
616  TATCTAGAGTGCGGGAGAGGAGAATGGAATTCCTAGTGTA 730           740           750           760
             |             |             |             |
656  GCGGTGAAATGCGTAGAGATTAGGAAGAACACCAGTGGCG 770           780           790           800
             |             |             |             |
696  AAGGCGATTCTCTGGACCGTAACTGACGCTGAGGCACGAA 810           820           830           840
             |             |             |             |
736  AGCGTGGGTAGC-AAACAGGATTAGATACCCTGGTAGTCC 850           860           870           880
             |             |             |             |
775  ACGCCGTAAACGATGAGTACTAGGTGTAGGAGG-TATCGA 890           900           910           920
             |             |             |             |
814  CCCCTTCTGTGCCGCA-GTAAACACAATAAGTACTCCGCC 930           940           950           960
             |             |             |             |
853  TGGGAAGTACGATCGCAAGATTAAAACTCAAAGGAATTGA
```

Fig. 8a continued

```
                 970          980          990         1000
                  |            |            |            |
 893   CGGGGCCCGCACAAGCAGCGGAGCATGTGGTTTAATTCG 1010         1020         1030         1040
                  |            |            |            |
 933   AAGCAACGCGAAGAACCTTACCTGGACTTGACATACCCTG 1050         1060         1070         1080
                  |            |            |            |
 973   AATATCTTAGAGATAAGAAG----CCCTTCGGG---C 1090         1100         1110         1120
                  |            |            |            |
1006   AGGGATACAGGTGGTGCATGGTTGTCGTCAGCTCGTGTCG 1130         1140         1150         1160
                  |            |            |            |
1046   TGAGATGTTAGGTT-AAGTCCTGCAACGAGCGCAACCCCT 1170         1180         1190         1200
                  |            |            |            |
1085   GTTGTTAGTTGCTAACA--TTTAGTTGAGCACTCTAGCAA 1210         1220         1230         1240
                  |            |            |            |
1123   GACTGCCGCGGTTAACGCGG-AGGAAGGTGGGAT-GACG 1250         1260         1270         1280
                  |            |            |            |
1161   TCAAATCATCAT-GCCCTTATG-TCCAGGGCAACACACG 1290         1300         1310         1320
                  |            |            |            |
1199   TGCTACAATGGGCAG-TACA-GAGAGAAGCAAGAYC-GCA 1330         1340         1350         1360
                  |            |            |            |
1235   -AGGTGGAGCAAACCTCA-AAAACT-GCCCCAGTTCGG- 1370         1380         1390         1400
                  |            |            |            |
1271   ---------------------ATTGCAGGCTGAAACTC 1410         1420         1430         1440
                  |            |            |            |
1289   GCCTACATGAAGTTGGAGTTGCTAGTAATCGCGAATCAGA
```

Fig. 8a continued

```
              1450            1460            1470            1480
               |               |               |               |
1329  A T G T C G C G G T G A A T A C G T T C C C G G G C C T T G - T A C A C A C C G 1490            1500            1510            1520
               |               |               |               |
1368  C C C G T C A C A C C A T G A G A G C T G G C A A C A - C C C G A A G T C C G T 1530            1540            1550            1560
               |               |               |               |
1407  A G T C T A A C - - - G A A A G A G G A C - G C G G C C G A A G G T G G G G T T 1570            1580            1590            1600
               |               |               |               |
1443  A G T A A T T G G G G T G A A - G T C G T A A C A A G G T A - - - - - - - - - -

1610            1620
               |               |
1471  - - - - - - - - - - - - - - - - - - - - - - - - - - -   [SEQ ID NO: 3]
```

FIG. 8b

- C. sporogenes X68189
- C. botulinum X73442
- C. proteolyticum X73448
- C. histolyticum M59094
- C. limosum M59096
- C. novyi L37594
- C. cellulovorans X73438
- C. butyricum X77834
- C. paraputrificum X73445
- C. paraperfringens M59102
- C. pasteurianum M23930
- C. magnum X77835
- C. scatologenes M59104
- C. tyrobutyricum M59113
- C. kluyveri M59092
- PS02
- C. ljungdahlii C-01 GU139550
- C. ljungdahlii ERI-2 GU139551
- C. ragsdalei AY170378
- C. ljungdahlii PETC GU139552
- C. autoethanogenum Y18178

0.01

FIG. 9

|  | PS02 | C. ljungdahlii ERI-2 GU139551 | C. ljungdahlii C-01 GU139550 | C. ragsdalei AY170378 | C. ljungdahlii PETC GU139552 | C. autoethanogenum Y18178 |
|---|---|---|---|---|---|---|
| PS02 | ID | | | | | |
| C. ljungdahlii ERI-2 | 99.86 | ID | | | | |
| C. ljungdahlii C-01 | 99.31 | 99.79 | ID | | | |
| C. ragsdalei AY170378 | 99.57 | 99.48 | 99.28 | ID | | |
| C. ljungdahlii PETC | 99.79 | 99.58 | 99.45 | 99.79 | ID | |
| C. autoethanogenum | 99.79 | 99.57 | 99.45 | 99.79 | 100.0 | ID |

| Similarity Matrix Scores | C. ljungdahlii PETC | C. ljungdahlii ERI-2 | C. autoethanogenum | C. ragsdalei | C. ljungdahlii C-01 | C. species PS02 |
|---|---|---|---|---|---|---|
| C. ljungdahlii PETC DSMZ 13528 | 100 | | | | | |
| C. ljungdahlii ERI-2 ATCC 55380 | 77.2 | 100 | | | | |
| C. autoethanogenum DSMZ 10061 | 70.5 | 58.2 | 100 | | | |
| C. ragsdalei ATCC BAA-622 | 64.8 | 37.6 | 39.7 | 100 | | |
| C. ljungdahlii C-01 ATCC 55988 | 35.7 | 28.2 | 29.7 | 25.4 | 100 | |
| C. species PS02 | 26.0 | 13.7 | 8.8 | 40.9 | 2.6 | 100 |

| Similarity Matrix Scores | C. ljungdahlii PETC | C. autoethanogenum | C. ljungdahlii ERI-2 | C. species PS02 | C. ragsdalei | C. ljungdahlii C-01 |
|---|---|---|---|---|---|---|
| C. ljungdahlii PETC DSMZ 13528 | 100 | | | | | |
| C. autoethanogenum DSMZ 10061 | 80.6 | 100 | | | | |
| C. ljungdahlii ERI-2 ATCC 55380 | 75.9 | 67.9 | 100 | | | |
| C. species PS02 | 73.5 | 69.8 | 71.3 | 100 | | |
| C. ragsdalei ATCC BAA-622 | 74.2 | 66.8 | 63.4 | 68.4 | 100 | |
| C. ljungdahlii C-01 ATCC 55988 | 24.2 | 27.6 | 36.8 | 42.7 | 21.4 | 100 |